(12) United States Patent
Slusarewicz et al.

(10) Patent No.: US 7,420,037 B2
(45) Date of Patent: Sep. 2, 2008

(54) HEAT SHOCK PROTEIN-BASED VACCINES AND IMMUNOTHERAPIES

(75) Inventors: Paul Slusarewicz, San Antonio, TX (US); Sunil Mehta, Durham, NC (US)

(73) Assignee: Antigenics Inc., New York, NY (US)

( * ) Notice: Subject to any disclaimer, the term of this patent is extended or adjusted under 35 U.S.C. 154(b) by 0 days.

(21) Appl. No.: 10/776,521

(22) Filed: Feb. 12, 2004

(65) Prior Publication Data

US 2005/0202033 A1 Sep. 15, 2005

Related U.S. Application Data

(60) Provisional application No. 60/447,142, filed on Feb. 13, 2003, provisional application No. 60/462,469, filed on Apr. 11, 2003, provisional application No. 60/463,746, filed on Apr. 18, 2003, provisional application No. 60/503,417, filed on Sep. 16, 2003.

(51) Int. Cl.
C07K 14/00 (2006.01)
C07K 4/00 (2006.01)
A61K 39/00 (2006.01)
A61K 45/00 (2006.01)
A61K 39/385 (2006.01)

(52) U.S. Cl. .............. 530/350; 424/278.1; 424/277.1; 530/300

(58) Field of Classification Search .............. None
See application file for complete search history.

(56) References Cited

U.S. PATENT DOCUMENTS

| | | |
|---|---|---|
| 5,348,945 A | 9/1994 | Berberian et al. |
| 5,498,538 A | 3/1996 | Kay et al. |
| 5,541,109 A | 7/1996 | Searfoss |
| 5,679,352 A | 10/1997 | Chong et al. |
| 5,750,119 A | 5/1998 | Srivastava |
| 5,837,251 A | 11/1998 | Srivastava |
| 5,935,576 A | 8/1999 | Srivastava |
| 5,961,979 A | 10/1999 | Srivastava |
| 5,962,262 A | 10/1999 | Hillman et al. |
| 5,985,270 A | 11/1999 | Srivastava |
| 5,997,873 A | 12/1999 | Srivastava |
| 6,017,540 A | 1/2000 | Srivastava et al. |
| 6,030,618 A | 2/2000 | Srivastava |
| 6,048,530 A | 4/2000 | Srivastava |
| 6,127,393 A | 10/2000 | Fernandex-Pol |
| 6,258,782 B1 | 7/2001 | Barney et al. |
| 6,663,868 B1 | 12/2003 | Rothman et al. |
| 2003/0166530 A1 | 9/2003 | Rothman et al. |
| 2004/0043419 A1 | 3/2004 | Rothman et al. |
| 2004/0071656 A1 | 4/2004 | Weiland et al. |
| 2005/0214312 A1 | 9/2005 | Fletchner et al. |

FOREIGN PATENT DOCUMENTS

| | | |
|---|---|---|
| EP | 0 538 952 | 4/1993 |
| WO | WO 89/04871 | 6/1989 |
| WO | WO 93/17712 | 9/1993 |
| WO | WO 94/11513 | 5/1994 |
| WO | WO 94/29459 | 12/1994 |
| WO | WO 95/24923 | 9/1995 |
| WO | WO 96/10411 | 4/1996 |
| WO | WO 97/06685 | 2/1997 |
| WO | WO 97/06821 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | WO 98/23735 | 6/1998 |
| WO | WO 98/35705 | 8/1998 |
| WO | WO 99/22761 | 5/1999 |
| WO | WO 99/42121 | 8/1999 |
| WO | WO 03/062262 | 7/2003 |

OTHER PUBLICATIONS

Arnold et al., 1995, "Cross-priming of Minor Histocompatibility Antigen-specific Cytotoxic T Cells upon Immunization with the Heat Shock Protein gp96." J. Exp. Med. 182:885-9.

Auger et al., 1996, "HLA-DR4 and HLA-DR10 motifs that carry susceptibility to rheumatoid arthritis bind 70-kD heat shock proteins." Nature Medicine 2:306-310.

Barrios et al., 1992, "Mycobacterial heat-shock proteins as carrier molecules. II: The use of the 70-kDa mycobacterial heat-shock protein as carrier for conjugated vaccines can circumvent the need for adjuvants and Bacillus Calmete Guerin priming." Euro. J. Immunol. 22:1365-1372.

Barrios et al., 1994, "Specificity of antibodies induced after immunization of mice with the mycobacterial heat shock protein of 65 kD." Clin. Exp. Immunol. 98:224-228.

Barrios et al., 1994, "Heat shock proteins as carrier molecules: in vivo helper effect mediated by *Escherichia coli* GroEL and DnaK proteins requires cross-linking with antigen." Clin. Exp. Immunol. 98:229-233.

Bauer et al., 1995, "Identification of H-2Kb binding and immunogenic peptides from human papilloma virus tumour antigens E6 and E7." Scand. J. Immunol. 42:317-323.

Blachere & Srivastava, 1995, "Heat shock protein-based cancer vaccines and related thoughts on immunogenicity of human tumors." Seminars in Cancer Biology 6:349-355.

Blachere et al., 1993, "Heat shock protein vaccines against cancer.", J. Immunother. 14(4):352-356.

(Continued)

Primary Examiner—Bruce Campbell
Assistant Examiner—Benjamin P Blumel
(74) Attorney, Agent, or Firm—Jones Day

(57) ABSTRACT

Hybrid antigens comprising an antigenic domain and improved heat shock protein binding domains are described which are useful for the induction of an immune response to the antigenic domain and thus can be used to treat infectious diseases and cancers that express an antigen of the antigenic domain.

45 Claims, 5 Drawing Sheets

OTHER PUBLICATIONS

Blachere et al., 1997, "Heat shock protein-peptide complexes, reconstituted in vitro, elicit peptide-specific cytotoxic T lymphocyte response and tumor immunity." J. Exp. Med. 186:1315-1322.
Blond-Elguindi et al., Affinity Panning of a Library of Peptides Displayed on Bacteriophages Reveals the Binding Specificity of BiP. Cell 75:717-728 (1993).
Borras-Cuesta et al., 1987, "Engineering of immunogenic peptides by co-linear synthesis of determinants recognized by B and T cells." Eur. J. Immunol. 17:1213-1215.
Castelli et al., 2001, "Human heat shock protein 70 peptide complexes specifically activate antimelanoma T cells." Cancer Res. 61(1):222-227.
Chen et al., 2000, "Enhancement of DNA vaccine potency by linkage of antigen gene to an HSP70 gene." Cancer Res. 60(4):1035-1042.
Cox et al., 1988, "Orientation of epitopes influences the immunogenicity of synthetic peptide dimers." Eur. J. Immunol. 18:2015-2019.
Czar et al., 1997, "Geldanamycin, a heat shock protein 90-binding benzoquinone ansamycin, inhibits steroid-dependent translocation of the glucocorticoid receptor from the cytoplasm to the nucleus." Biochemistry 36:7776-7785.
Davidoff et al., 1992, "Immune response to p53 is dependent upon p53/HSP70 complexes in breast cancers." Proc. Natl. Acad. Sci. USA 89:3439-3442.
Del Guidice, 1994, "Hsp70: a carrier molecule with built-in adjuvanticity." Experientia 50:1061-1066.
DeNagel & Pierce et al., 1993, "Heat shock proteins in immune responses." Critical Reviews In Immunology 13:71:81.
Dillman et al., 1995, "Heat Shock Proteins and Ischemic Injury." J. Cell. Biochem., Suppl. 19B, p. 190.
Edgington, 1995, "Therapeutic applications of heat shock proteins." Biotechnol. 13:1442-1444.
Fedoseyeva et al., 2001, "CD4+ T cell responses to self- and mutated p53 determinants during tumorigenesis in mice." J. Immunol. 164(11):5641-5651.
Feldweg & Srivastava, 1995, "Molecular heterogeneity of tumor rejection antigen/heat shock protein GP96." Int. J. Cancer 63:310-314.
Flajnik et al., 1991, "Which came first, MHC Class 1 or Class II?" Immunogenetics 33:295-300.
Flynn et al., 1989, "Peptide-dependent stimulation of the ATPase activity of the molecular chaperone BiP is the result of conversion of oligomers to active monomers." Science 245:385-390.
Francis et al., 1987, "Non-responsiveness to a foot-and-mouth disease virus peptide overcome by addition of foreign helper T-cell determinants." Nature 330:168-170.
Galigniana et al., 1998, "Heat shock protein 90-dependent (geldanamycin-inhibited) movement of the glucocorticoid receptor through the cytoplasm to the nucleus requires intact cytoskeleton." Mol. Endo. 12:1903-1913.
Gething, et al., 1995, "Binding Sites for Hsp70 Molecular Chaperones in Natural Proteins." Cold Spring Harb. Symp. Quant. Biol. 60:417-28.
Giboa, 1996, "Immunotherapy of cancer with genetically modified tumor vaccines." Seminars in Oncology 23:101-107.
Gragerov et al., 1994, "Different peptide binding specificities of hsp70 family members." J. Mol. Biol. 235:133-135.
Gragerov et al., 1994, "Specificity of DnaK-peptide binding." J. Mol. Biol. 235:848-854.
Greene et al., 1995, "Effect of nucleotide on the binding of peptides to 70-kDa heat shock protein." J. Biol. Chem. 270(7):2967-2978.
Heike et al., 1996, "Heat shock protein-peptide complexes for use in vaccines." J. Leukoc. Biol. 60(2):153-158.
Heikema et al., 1997, "Generation of heat shock protein-based vaccines by intracellular loading of gp96 with antigenic peptides." Immunol. Lett. 57(1-3):69-74.
Hinds et al., 1987, "Immunological evidence for the association of p53 with a heat shock protein, hsc70, in p53-plus-ras-transformed cell lines." Mol Cell Biol. 7(8):2863-2869.
Hohfeld et al., 1995, "Hip, a novel cochaperone involved in the eukaryotic Hsc70/Hsp40 reaction cycle." Cell 83:589-598.

Huang et al., 2000, "In Vivo Cytotoxic T Lymphocytes Elicitation by Mycobacterial Heat Shock Protein 70 Fusion Proteins Maps to a Discrete Domain and Is CD4.sup.30 T Cell Independent." J. Exp. Med. 191:403-408.
Jaattela, 1995, "Over-expression of hsp70 confers tumorigenicity to mouse fibrosarcoma cells." Int. J. Cancer, 60 (5), pp. 689-693.
Jakob et al., 1996, "Assessment of the ATP binding properties of Hsp90." J. Biol. Chem. 271:10035-10041.
Jindal, S., 1996, "Heat shock proteins: applications in health and disease." Trends Biotechnol. 14:17-20.
Konen-Waisman et al., 1999, "Self heat-shock protein (hsp60) peptide serves in a conjugate vaccine against a lethal pneumococcal infection." J. Infect. Dis. 179(2):403-413.
Lewis et al., 1999, "Pilot study of vaccination with autologous tumor-derived gp96 heat shock protein-peptide complex(HSPPC-96) in patients with resected pancreatic adenocarcinoma." Meeting Abstract, Proceedings of the Annual Meeting of the American Society of Clinical Oncology, 18:A1687.
Li, Z. et al., 1993, "Tumor rejection antigen gp96/grp94 is an ATPase: implications for protein folding and antigen presentation." EMBO J. 12:3143-51.
Little, et al., 1994, "The glucose-regulated proteins (GRP78 and GRP94): functions, gene regulation, and applications." Critical Reviews in Eukaryotic Gene Expression, 1994 4(1) pp. 1-18.
Lopez-Guerrero et al., 1993, "Modulation of adjuvant arthritis in Lewis rats by recombinant vaccinia virus expressing the human 60-kilodalton heat shock protein." Infect. Immun. 61(10):4225-4231.
Lovett et al., 1993, "Rubella virus-specific cytotoxic T-lymphocyte responses: identification of the capsid as a target of major histocompatibility complex class I-restricted lysis and definition of two epitopes." J. Virol. 67(10):5849-5858.
Lowrie et al., 1994, "Towards a DNA vaccine against tuberculosis." Vaccine 12:1537-1540.
Lowrie et al., 1995, "*Mycobacterium Leprae* HSP65 Vaccinates mice against Tuberculosis when Expressed from the Cloned Gene in Transplanted Bone Marrow Cells." J. Cell. Biochem. Suppl. 0(19b):220.
Lukacs et al., 1993, "Tumor cells transfected with a bacterial heat-shock gene lose tumorigenicity and induce protection against tumors." J. Exp. Med. 178:343-348.
Lukacs et al., 1994, "Protection against tumours by mycobacterial heat shock protein gene." Cancer Gene Therapy, 1:217.
Lussow et al., 1991, "Mycobacterial heat-shock proteins as carrier molecules." J. Eur. Immunol. 21:2297-2302.
Mastrangelo et al., 1996, "Gene therapy for human cancer: an essay for clinicians." Seminars in Oncology, 23:4-21.
McCarty et al., 1995, "The role of ATP in the functional cycle of the DnaK chaperone system." J. Mol. Biol. 249:126-137.
Melcher et al., 1998, "Tumor Immonogenicity is Determined by the Mechanism of Cell Death Via Induction of Heat Shock Protein Expression." Nature Medicine 4:581-587.
Melnick, et al., 1992, "The endoplasmic reticulum stress protein GRP94 in addition to BiP, associates with unassembled immunoglobulin chains." J. of Biochem. 267:21303-21306.
Meng et al., 1999, "Tumor suppressor gene as targets for cancer therapy." Gene Therapy of Cancer, Lattime and Gerson, Eds., Academic Press, Chap. 1, pp. 3-20.
Minami et al., 1996, "Regulation of the heat-shock protein 70 reaction cycle by the mammalian DnaJ homolog, Hsp40." J. Biol. Chem. 271:19617-19624.
Moroi, 2000, "Induction of cellular immunity by immunization with novel hybrid peptides complexed to heat shock protein 70." Proc Natl Acad Sci U S A 97(7):3485-90.
Multhoff et al., 1995, "A stress-inducible 72-kDa heat-shock protein (HSP72) is expressed on the surface of human tumor cells, but not on normal cells." Int. J. Cancer 61:272-279.
Munro and Pelham, 1987, "A C-terminal signal prevents secretion of luminal ER proteins." Cell, 480:899-907.
Mustafa et al., 1993, "Human T cells recognize mycobacterial heat shock proteins in the context of multiple HLA-DR molecules: studies with healthy subjects vaccinated with *Mycobacterium bovis* BCG and *Mycobacterium leprae*." Infection and Immunity 61:5294-5301.

Nadeau et al., 1992, "83-kilodalton heat shock proteins of trypanosomes are potent peptide-stimulated ATPases." Protein Science 1:970-979.

Nadeau et al., 1992, "Hsp90 chaperonins possess ATPase activity and bind heat shock transcription factors and peptidyl prolyl isomerases." J. Biol. Chem. 268:1479-1487.

Ngo et al., 1994, "Computational Complexity Protein Structure Prediction and the Levinthal Paradox." Birkhauser Boston, vol. 14, pp. 491-495.

Nieland et al., 1996, "Isolation of an immunodominant viral peptide that is endogenously bound to the stress protein GP96/GRP94." Proc. Natl. Acad. Sci. USA 93:6135-6139.

Nilsson et al., 1992, "Fusion proteins in biotechnology and structural biology." Curr. Opin. Struct. Biol. 2:569-575.

Nygren et al., 1994, "Engineering proteins to facilitate bioprocessing." Trends Biotechnol. 12(5):184-188.

Omura et al., 1979, "Herbimycin, a new antibiotic produced by a strain of Streptomyces." J. Antibiotics 32:255-261.

Palleros et al., 1993, "ATP-induced protein-Hsp70 complex dissociation requires K+ but not ATP hydrolysis." Nature 365:664-666.

Pardoll, 1993, "New strategies for enhancing the immunogenicity of tumors." Current Opinion in Immunology 5:719-725.

Partidos et al., 1991, "Immune responses in mice following immunization with chimeric synthetic peptides representing B and T cell epitopes of measles virus proteins." J. Gen. Virol. 72:1293-1299.

Pelham, 1988, "Evidence that luminal ER proteins are sorted from secreted proteins in a post-ER compartment." EMBO J. 7:913-918.

Perraut, 1993, "Successful primate immunization with peptides conjugated to purified protein derivative or mycobacterial heat shock proteins in the absence of adjuvants." Clin. Exp. Immunol. 93:382-386.

Pidoux et al., 1992, "Analysis of the BiP gene and identification of an ER retention signal in *Schizosaccharomyces pombe*." EMBO J. 11:1583-1591.

Plumier et al., 1995, "Transgenic mice expressing the human heat shock protein 70 have improved post-ischemic myocardial recovery." J. Clin. Invest. 95 (4), pp. 1854-1860.

Porgador et al., 1994, "Immunotherapy of tumor metastasis via gene therapy." Nat. Immun. 13:113-130.

Retzlaff et al., 1994, "Bacterial heat shock proteins directly induce cytokine mRNA and interleukin-1 secretion in macrophage cultures." Infect. Immun. 62:5689-5693.

Riddell et al., 1996, "T-cell mediated rejection of gene-modified HIV-specific cytotoxic T lymphocytes in HIV-infected patients." Nature Medicine 2:216-223.

Rosenberg et al., 1996, "T7 Select Phage Display System: A powerful new protein display system based on Bacteriophage T7." inNovations (newsletter of Novagen, Inc.) No. 6, pp. 1-6.

Sato et al., 1994, "70 kDA heat shock protein as a tumor antigen and a target for the host's anti-tumor resistance by cytotoxic T lymphocytes." Proc. Annu. Meet. Am. Assoc. Cancer Res. 35:A2959.

Scheerlinck et al., 1993, Redistribution of a murine humoral immune response following removal of an immunodominant B cell epitope from a recombinant fusion protein. Mol. Immunol. 30:733-739.

Schmid et al., 1994, "Kinetics of molecular chaperone action." Science 263:971-973.

Silva and Lowrie, 1994, "A single mycobacterial protein (hsp 65) expressed by a transgenic antigen-presenting cell vaccinates mice against tuberculosis." Immunology 82:244-248.

Srivastava & Maki, 1991, "Stress-induced proteins in immune response to cancer." Current Topics in Microbiology and Immunology 167:109-123.

Srivastava and Udono, 1994, "Heat shock protein-peptide complexes in cancer immunotherapy." Curr. Opin. Immunol. 6(5):728-732.

Srivastava et al., 1986, "Tumor rejection antigens of chemically induced sarcomas of inbred mice." Proc. Natl. Acad. Sci. USA 83:3407-3411.

Srivastava, 1993, "Peptide-binding heat shock proteins in the endoplasmic reticulum: role in immune response to cancer and in antigen presentation." Adv. Cancer Res. 62:153-177.

Srivastava, 1994, "Heat shock proteins in immune response to cancer: the Fourth Paradigm." Experentia 50:1054-1060.

Srivastava, 2002, "Interaction of Heat Shock Proteins with Peptides and Antigen Presenting Cells: Chaperoning of the Innate and Adaptive Immune Response." Ann. Rev. Immunol. 20:395-425.

Srivatava et al., 1987, "5'-structural analysis of genes encoding polymorphic antigens of chemically induced tumors." Proc. Natl. Acad. Sci. USA 84:3807-3811.

Suto, et al., 1995, "A Mechanism for the Specific Immunogenicity of Heat Shock Protein-Chaperoned Peptides." Science 269:1585-7.

Suzue, et al., 1996, "Adjuvant-Free hsp Fusion Protein System Elicits Humoral and Cellular Immune Responses to HIV-1 p24.sup.1." J. Immunol. 156:873-9.

Suzuki et al., 1991, "Regulating the retention of T-cell receptor alpha chain variants within the endoplasmic reticulum: Ca(2+)-dependent association with BiP." J. Cell Biol. 114:189-205.

Tamura et al., 1997, "Immunotherapy of tumors with autologous tumor-derived heat shock protein preparations." Science 278:117-120.

Tarpey, I. et al., 1994, "Human cytotoxic T lymphocytes stimulated by endogenously processed human papillomavirus type 11 E7 recognize a peptide containing a HLA-A2 (A*0201) motif." Immunology 81:222-7.

Tavaria et al., 1996, "Cell Stress and Chaperones 1:23-28." Cell Stress and Chaperones 1:23-28.

Theobald et al., 1995, "Targeting p53 as a general tumor antigen." Proc. Natl. Acad. Sci. USA 92(26):11993-11997.

Thomson et al., 1995, "Minimal epitopes expressed in a recombinant polyepitope protein are processed and presented to CD8+ cytotoxic T cells: implications for vaccine design." Proc. Natl. Acad. Sci. USA 92(13):5845-5849.

Thomson et al., 1996, "Recombinant polyepitope vaccines for the delivery of multiple CD8 cytotoxic T cell epitopes." J. Immunol. 157(2):822-6.

Todryk et al., 1999, "Heat Shock Protein 70 Induced During Tumor Cell Killing Induces Th1 Cytokines and Targets Immature Dendritic Cell Precursors to Enhance Antigen Uptake." J. Immunol. 163:1398-1408.

Udono et al., 1994, "Comparison of tumor-specific immunogenicities of stress-induced proteins gp96, hsp90, and hsp70." J. Immun. 152, pp. 5398-5403.

Udono, et al., 1993, "Heat shock protein 70-associated peptides elicit specific cancer immunity." J. Exp. Med. 178:1391-6.

Udono, et al., 1994, "Cellular requirements for tumor-specific immunity elicited by heat shock proteins: Tumor rejection antigen gp96 primes CD8+ T Cells in vivo." Pro. Natl. Acad. Sci. 91:3077-81.

Ullrich et al., 1986, "A mouse tumor-specific transplantation antigen is a heat shock-related protein." Proc. Natl. Acad. Sci. USA 83:3121-3125.

Verma et al., 1997, "Gene therapy—promises, problems and prospects." Nature 389(6648):239-242.

Von Heijne, 1985, "Signal sequences. The limits of variation." J. Mol. Biol. 184:99-105.

Wearsch et al., 1997, "Interaction of endoplasmic reticulum chaperone GRP94 with peptide substrates is adenine nucleotide-independent." J. Biol. Chem. 272:5152-5156.

Wells et al., 1998, "Hsp72-mediated Augmentation of MHC Class I Surface Expression and Endogenous Antigen Presentation." Int. Immunol 10:609-617.

Whitesell, et al., 1994, "Inhibition of heat shock protein HSP90-pp60v-src heteroprotein complex formation by benzoquinone ansamycins: essential role for stress proteins in oncogenic transformation." Proc. Natl. Acad. Sci. USA 91:8324-8328.

Yamamoto et al., 1993, "Listeria monocytogenes-induced gamma interferon secretion by intestinal intraepithelial gamma/delta T lymphocytes." Infection and Immunity 61:2154-2161.

Yamazaki et al., 1999, "Cutting Edge: Tumor Secreted Heat Shock-Fusion Protein Elicits CD8 Cells for Rejection." J. Immunol. 163:5178-5182.

Zhu et al., 1995, "Both immunization with protein and recombinant vaccinia virus can stimulate CTL specific for the E7 protein of human papilloma virus 16 in H-2d mice." Scand. J. Immunol. 42:557-563.

Zhu et al., 1996, "Structural analysis of substrate binding by the molecular chaperone DnaK." Science 272:1606-1614.

Anderson, 1998, "Human gene therapy", Nature 392(6679 Suppl):25-30.

U.S. Appl. No. 10/170,738, filed Jun. 13, 2002, Rothman et al.

Fourie et al., Common and divergent peptide binding specificities of hsp70 molecular chaperones. J Biol Chem. Dec. 2, 1994;269(48):30470-30478.

McCarty et al., Regulatory region C of the *E. coli* heat shock transcription factor, sigma32, constitutes a DnaK binding site and is conserved among eubacteria. J Mol Biol. Mar. 15, 1996;256(5):829-837.

[S] = concentration of hybrid peptide

Y = fraction of labeled reporter peptide bound

*In Vitro* Macrophage-T cell Activation Assay

*In Vivo* Responses to HSP70:Hybrid Peptide complexes

Blocking of *In Vivo* Responses to HSP70:SIINFEKLGSGHWDFAWDW complexes with the addition of higher affinity NLLRLTGW

HEAT SHOCK PROTEIN-BASED VACCINES AND IMMUNOTHERAPIES

CROSS-REFERENCE TO RELATED APPLICATIONS

This application claims priority under 35 U.S.C. § 119(e) to provisional applications 60/447,142, filed Feb. 13, 2003; 60/462,469, filed Apr. 11, 2003; 60/463,746, filed Apr. 18, 2003; and 60/503,417, filed Sep. 16, 2003, all four of which are incorporated herein by reference in their entireties.

INTRODUCTION

The present invention relates to methods and compositions for inducing an immune response in a subject, wherein the subject is administered an effective amount of at least one or more defined hybrid antigens optionally in combination with one or more heat shock proteins. These methods and compositions may be used in the treatment of infectious diseases and cancers.

BACKGROUND OF THE INVENTION

Heat shock proteins were originally observed to be expressed in increased amounts in mammalian cells which were exposed to sudden elevations of temperature, while the expression of most cellular proteins is significantly reduced. It has since been determined that such proteins are produced in response to various types of stress, including glucose deprivation. As used herein, the term "heat shock protein" will be used to encompass both proteins that are expressly labeled as such as well as other stress proteins, including homologues of such proteins that are expressed constitutively (i.e., in the absence of stressful conditions). Examples of heat shock proteins include BiP (also referred to as grp78), hsp70, hsc70, gp96 (grp94), hsp60, hsp40 and hsp90.

Heat shock proteins have the ability to bind other proteins in their non-native states, and in particular to bind nascent peptides emerging from ribosomes or extruded into the endoplasmic reticulum. Hendrick and Hartl, *Ann. Rev. Biochem.* 62:349-384 (1993); Hartl, *Nature* 381:571-580 (1996). Further, heat shock proteins have been shown to play an important role in the proper folding and assembly of proteins in the cytosol, endoplasmic reticulum and mitochondria; in view of this function, they are referred to as "molecular chaperones." Frydman et al., *Nature* 370:111-117 (1994); Hendrick and Hartl, *Ann. Rev. Biochem.* 62:349-384 (1993); Hartl, *Nature* 381:571-580 (1996).

For example, the protein BiP, a member of a class of heat shock proteins referred to as the hsp70 family, has been found to bind to newly synthesized, unfolded µ immunoglobulin heavy chain prior to its assembly with light chain in the endoplasmic reticulum. Hendershot et al., *J. Cell Biol.* 104: 761-767 (1987). Another heat shock protein, gp96, is a member of the hsp90 family of stress proteins which localizes in the endoplasmic reticulum. Li and Srivastava, *EMBO J.* 12:3143-3151 (1993); Mazzarella and Green, *J. Biol. Chem.* 262:8875-8883 (1987). It has been proposed that gp96 may assist in the assembly of multi-subunit proteins in the endoplasmic reticulum. Wiech et al., *Nature* 358:169-170 (1992).

It has been observed that heat shock proteins prepared from tumors in experimental animals were able to induce immune responses in a tumor-specific manner; that is to say, heat shock protein purified from a particular tumor could induce an immune response in an experimental animal which would inhibit the growth of the same tumor, but not other tumors. Srivastava and Maki, *Curr. Topics Microbiol.* 167:109-123 (1991). Genes encoding heat shock proteins have not been found to exhibit tumor-specific DNA polymorphism. Srivastava and Udono, *Curr. Opin. Immunol.* 6:728-732 (1994). High resolution gel electrophoresis has indicated that gp96 may be heterogeneous at the molecular level. Feldweg and Srivastava, *Int. J. Cancer* 63: 310-314 (1995). Evidence suggests that the source of heterogeneity may be populations of small peptides adherent to the heat shock protein, which may number in the hundreds. Id. It has been proposed that a wide diversity of peptides adherent to tumor-synthesized heat shock proteins may render such proteins capable of eliciting an immune response in subjects having diverse HLA phenotypes, in contrast to more traditional immunogens which may be somewhat HLA-restricted in their efficacy. Id.

Recently, Nieland et al. (*Proc. Natl. Acad. Sci. U.S.A.* 93:6135-6139 (1996)) identified an antigenic peptide containing a cytotoxic T lymphocyte (CTL) vesicular stomatitis virus (VSV) epitope bound to gp96 produced by VSV-infected cells. Neiland's methods precluded the identification of any additional peptides or other compounds which may also have bound to gp96, and were therefore unable to further characterize higher molecular weight material which was bound to gp96 and detected by high pressure liquid chromatography.

It has been reported that a synthetic peptide comprising multiple iterations of NANP (Asn Ala Asn Pro) (SEQ ID NO:1) malarial antigen, chemically cross-linked to glutaraldehyde-fixed mycobacterial hsp65 or hsp70, was capable of inducing antibody formation (i.e., a humoral response) in mice in the absence of any added adjuvant; a similar effect was observed using heat shock protein from the bacterium *Escherichia coli*. Del Guidice, *Experientia* 50:1061-1066 (1994); Barrios et al., *Clin. Exp. Immunol.* 98:224-228 (1994); Barrios et al., *Eur. J. Immunol.* 22:1365-1372 (1992). Cross-linking of synthetic peptide to heat shock protein and possibly glutaraldehyde fixation was required for antibody induction. Barrios et al., *Clin. Exp. Immunol.* 98:229-233.

PCT/US96/13363 describes hybrid antigens comprising an antigenic domain and a heat shock protein binding domain that, in a complex with a heat shock protein, induces immunological responses to antigens and are thus useful for treatment of cancer and infectious diseases. PCT/US98/22335 describes additional heat shock protein binding domains for similar uses. It has now been discovered that improvements in the heat shock protein binding domains leads to an increase in biological activity, and thus an increase in inducing an immune response against the antigenic portion of the hybrid antigen, as well as prevention and treatment of diseases associated with the antigenic domains. It is towards these improved heat shock protein binding domains that the present application is directed.

SUMMARY OF THE INVENTION

The present invention relates to methods and compositions for inducing an immune response in a subject, wherein at least one defined hybrid antigen optionally in a complex with a heat shock protein is administered to the subject. The hybrid antigen comprises an antigenic domain and a heat shock protein binding domain. Induction of an immune response to an antigen associated with a disease such as an infectious disease or tumor is useful for treatment of the disease. The antigenic or immunogenic domain of the hybrid antigen may be an entire protein or peptide antigen, or may be only a portion of the selected antigen, for example a selected epitope of the antigen. In specific, non-limiting embodiments of the invention, the heat shock protein binding domain comprises a peptide having the sequence:
Asn Leu Leu Arg Leu Thr Gly Trp (SEQ ID NO:417),
Phe Tyr Gln Leu Ala Leu Tyr Trp (SEQ ID NO:418), or
Arg Lys Leu Phe Phe Asn Leu Arg Trp (SEQ ID NO:419).

In alternate embodiments, the heat shock protein binding domain comprises a peptide have a sequence among SEQ ID NOs:132-185 and 193-356.

The present invention provides for methods of administering such hybrid antigens alone, as well as heat shock protein/hybrid antigen compositions, the latter comprising (i) combining one or more heat shock protein with one or more hybrid antigens in vitro, under conditions wherein binding of hybrid antigen to heat shock protein occurs to form a hybrid antigen/heat shock protein complex; and (ii) administering the hybrid antigen, bound to heat shock protein, in an effective amount to a subject in need of such treatment.

Alternatively, hybrid antigens optionally in combination with heat shock protein may be introduced into a subject by administering to the subject a nucleic acid encoding the hybrid antigen, optionally with nucleic acid encoding the heat shock protein.

Thus, in a first aspect, the invention is directed to a hybrid antigen consisting essentially of an antigenic domain of an infectious agent or tumor antigen, a binding domain that non-covalently binds to a heat shock protein, and a peptide linker separating the antigenic domain and the binding domain, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356.

In a second aspect, the invention is directed to a hybrid antigen consisting essentially of a plurality of antigenic domains of an infectious agent or tumor antigen, a binding domain that non-covalently binds to a heat shock protein, and peptide linkers separating the antigenic domains and the binding domain, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In a particular embodiment, at least one of the antigenic domains in the aforementioned hybrid antigen is a T helper epitope.

In a third aspect, the invention is directed to a hybrid antigen comprising an antigenic domain of an infectious agent or tumor antigen and a binding domain that non-covalently binds to a heat shock protein, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In a particular embodiment, the aforementioned hybrid antigen has a peptide linker separating the antigenic domain and the binding domain.

In a fourth aspect, the invention is directed to a hybrid antigen comprising a plurality of antigenic domains of an infectious agent or tumor antigen and a binding domain that non-covalently binds to a heat shock protein, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In a particular embodiment, peptide linkers separate the antigenic domains and the binding domain. In yet another embodiment, at least one of the antigenic domains is a T helper epitope.

In a fifth aspect, the invention is directed to a composition for inducing an immune response to an infectious agent or tumor antigen comprising at least one hybrid antigen, the hybrid antigen comprising an antigenic domain of the infectious agent or tumor antigen and a binding domain that non-covalently binds to a heat shock protein, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, a peptide linker separates the antigenic domain and the binding domain. In another embodiment, the composition comprises a plurality of hybrid antigens, and one of the hybrid antigens can comprise a T helper epitope.

In a sixth aspect, the invention is directed to a composition for inducing an immune response to an infectious agent or tumor antigen comprising at least one hybrid antigen, the hybrid antigen comprising a plurality of antigenic domains at least one of which is from the infectious agent or tumor antigen, and a binding domain that non-covalently binds to a heat shock protein, wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, peptide linkers separate the antigenic domains from the binding domain. In another embodiment, at least one of the antigenic domains comprises a T helper epitope.

In a seventh aspect, the invention is directed to a composition for inducing an immune response to an infectious agent or tumor antigen comprising at least one hybrid antigen, the hybrid antigen consisting essentially of an antigenic domain of an infectious agent or tumor antigen, a binding domain that non-covalently binds to a heat shock protein, and a peptide linker separating the antigenic domain and the binding domain, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the aforementioned composition comprises a plurality of hybrid antigens. In another aspect, at least one of the plurality of hybrid antigens comprises a T helper epitope.

In an eighth aspect, the invention is directed to a composition for inducing an immune response to an infectious agent or tumor antigen comprising at least one hybrid antigen, the hybrid antigen consisting essentially of a plurality of antigenic domains at least one of which is from an infectious agent or tumor antigen, a binding domain that non-covalently binds to a heat shock protein, and a peptide linker separating the antigenic domain and the binding domain, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, at least one of the antigenic domains comprises a T helper epitope.

In a ninth aspect, the invention is directed to a method for inducing an immune response to an infectious agent or tumor antigen comprising administering to a subject a complex of:
(a) a hybrid antigen comprising at least one antigenic domain of the infectious agent or tumor antigen, and a binding domain comprising a peptide that non-covalently binds to a heat shock protein; and
(b) a heat shock protein;
wherein the hybrid antigen and the heat shock protein are non-covalently bound, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the complex comprises a plurality of hybrid antigens. In an embodiment, at least one of the hybrid antigens is a T helper epitope. In another embodiment, the hybrid antigen comprises a plurality of antigenic domains, and at least one of the antigenic domains can be a T helper epitope. In yet another embodiment wherein the complex comprises a plurality of hybrid antigens, at least one of the hybrid antigens comprises a plurality of antigenic domains. In an embodiment of this aspect of the invention, a peptide linker separates the antigenic domain and the binding domain. In another embodiment of this aspect of the invention, the heat shock protein is a hsp70.

In a tenth aspect, the invention is directed to a method for inducing an immune response to an infectious agent or tumor antigen comprising administering to a subject a complex of a heat shock protein and a hybrid antigen, the hybrid antigen consisting essentially of at least one antigenic domain of an infectious agent or tumor antigen, a binding domain that non-covalently binds to a heat shock protein, and a peptide linker separating the antigenic domain and the binding domain, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the complex comprises a plurality of hybrid antigens. In another embodiment, at least one of the hybrid antigens is a T helper epitope. In a further embodiment, the hybrid antigen comprises a plurality of antigenic domains. In yet a further embodiment, at least one of the antigenic domains is a T helper epitope. In still yet another embodiment, the complex comprises a plurality of hybrid antigens, at least one of the hybrid antigens comprising a plurality of antigenic domains. In a preferred embodiment of this aspect, the heat shock protein is a hsp70.

In an eleventh aspect, the invention is directed to a method for inducing an immune response to an infectious agent or tumor antigen comprising administering to a subject at least one hybrid antigen comprising at least one antigenic domain of the infectious agent or tumor antigen, and a binding domain comprising a peptide that non-covalently binds to a heat shock protein, wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the complex comprises a plurality of hybrid antigens. In another embodiment, at least one of the hybrid antigens is a T helper epitope. In another embodiment, the hybrid antigen comprises a plurality of antigenic domains. In a further embodiment, at least one of the antigenic domains is a T helper epitope. In yet a further embodiment, the complex comprises a plurality of hybrid antigens, at least one of the hybrid antigens comprising a plurality of antigenic domains. In another embodiment of this aspect of the invention, a peptide linker separates the antigenic domain and the binding domain.

In a twelfth embodiment, the invention is directed to a method for inducing an immune response to an infectious agent or tumor antigen comprising administering to a subject at least one hybrid antigen, the hybrid antigen consisting essentially of at least one antigenic domain of an infectious agent or tumor antigen, a binding domain that non-covalently binds to a heat shock protein, and a peptide linker separating the antigenic domain and the binding domain, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the complex comprises a plurality of hybrid antigens. In a further embodiment, at least one of the hybrid antigens is a T helper epitope. In another embodiment, the hybrid antigen comprises a plurality of antigenic domains. In yet another embodiment, at least one of the antigenic domains is a T helper epitope. In yet still a further embodiment, the complex comprises a plurality of hybrid antigens, at least one of the hybrid antigens comprising a plurality of antigenic domains.

In a thirteenth aspect, the invention is directed to a method for treating an infectious disease or cancer comprising administering to a subject a complex of:
  (a) a hybrid antigen comprising at least one antigenic domain of an infectious agent or tumor antigen associated with the infectious disease or cancer, and a binding domain comprising a peptide that non-covalently binds to a heat shock protein; and
  (b) a heat shock protein;
wherein the hybrid antigen and the heat shock protein are non-covalently bound, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the complex comprises a plurality of hybrid antigens. In another embodiment, at least one of the hybrid antigens is a T helper epitope. In yet another embodiment, the hybrid antigen comprises a plurality of antigenic domains. In still another embodiment, at least one of the antigenic domains is a T helper epitope. In yet still a further embodiment, the complex comprises a plurality of hybrid antigens, at least one of the hybrid antigens comprising a plurality of antigenic domains. In an embodiment of this aspect of the invention, a peptide linker separates the antigenic domain and the binding domain. In a preferred embodiment of this aspect of the invention, the heat shock protein is a hsp70.

In a fourteenth aspect, the invention is directed to a method for treating an infectious disease or cancer comprising administering to a subject a complex of a heat shock protein and a hybrid antigen, the hybrid antigen consisting essentially of at least one antigenic domain of an infectious agent or tumor antigen associated with the infectious disease or cancer, a binding domain that non-covalently binds to a heat shock protein, and a peptide linker separating the antigenic domain and the binding domain, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the complex comprises a plurality of hybrid antigens. In another aspect, at least one of the hybrid antigens is a T helper epitope. In yet another aspect, the hybrid antigen comprises a plurality of antigenic domains. In yet another aspect, at least one of the antigenic domains is a T helper epitope. In a further aspect, the complex comprises a plurality of hybrid antigens, at least one of the hybrid antigens comprising a plurality of antigenic domains. In a preferred embodiment, the heat shock protein is a hsp70.

In a fifteen aspect, the invention is directed to a method for treating an infectious disease or cancer comprising administering to a subject at least one hybrid antigen comprising at least one antigenic domain of an infectious agent or tumor antigen associated with the infectious disease or cancer, and a binding domain comprising a peptide that non-covalently binds to a heat shock protein, wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the complex comprises a plurality of hybrid antigens. In another aspect, at least one of the hybrid antigens is a T helper epitope. In yet another aspect, the hybrid antigen comprises a plurality of antigenic domains. In still a further aspect, at least one of the antigenic domains is a T helper epitope. In still yet another aspect, the complex comprises a plurality of hybrid antigens, at least one of the hybrid antigens comprising a plurality of antigenic domains. In one embodiment of this aspect of the invention, a peptide linker separates the antigenic domain and the binding domain.

In a sixteenth aspect, the invention is directed to a method for treating an infectious disease or cancer comprising administering to a subject at least one hybrid antigen, the hybrid antigen consisting essentially of at least one antigenic domain of an infectious agent or tumor antigen associated with an infectious disease or cancer, a binding domain that non-covalently binds to a heat shock protein, and a peptide linker separating the antigenic domain and the binding domain, and wherein the binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In one embodiment, the complex comprises a plurality of hybrid antigens. In another embodiment, at least one of the hybrid antigens is a T helper epitope. In yet another embodiment, the hybrid antigen comprises a plurality of antigenic domains. In still yet another embodiment, at least one of the antigenic domains is a T helper epitope. In another embodiment, the complex comprises a plurality of hybrid antigens, at least one of the hybrid antigens comprising a plurality of antigenic domains.

In a seventeenth aspect, the invention is directed to a peptide comprising Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356.

In an eighteenth aspect, the invention is directed to an immunogenic polypeptide comprising a plurality of antigenic domains, and a binding domain comprises Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356.

In a nineteenth aspect, the invention is directed to the peptides Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356.

In a twentieth aspect, the invention is directed to a polynucleotide encoding any of the aforementioned hybrid antigens.

In a twenty-first aspect, the invention is directed to a method of inducing an immune response to an infectious disease or cancer comprising administering to a subject a polynucleotide encoding a hybrid antigen comprising an antigenic domain of an infectious agent or tumor antigen and a heat shock protein binding domain.

In a twenty-second aspect, the invention is directed a method of inducing an immune response to an infectious disease or cancer comprising administering to a subject a polynucleotide encoding a hybrid antigen as mentioned above, and a polynucleotide encoding a heat shock protein. In a preferred embodiment, the encoded heat shock protein is a hsp70.

In a twenty-third aspect, the invention is directed to polynucleotides encoding Asn Leu Leu Arg Leu Thr Gly Trp (SEQ ID NO:417), Phe Tyr Gln Leu Ala Leu Tyr Trp (SEQ ID NO:418), Arg Lys Leu Phe Phe Asn Leu Arg Trp (SEQ ID NO:419), or any of SEQ ID NOs:132-185 and 193-356. In a further embodiment, the invention is directed to polynucleotides encoding hybrid antigens as described above. In another embodiment, the invention is directed to inducing an immune response to an infectious agent or cancer comprising administering to a subject a polynucleotide encoding a hybrid antigen as mentioned above, optionally together with a polynucleotide encoding a heat shock protein, preferably hsp70. In a further embodiment, the invention is directed to treating an infectious disease or cancer comprising administering to a subject a polynucleotide encoding a hybrid antigen as mentioned above, optionally together with a polynucleotide encoding a heat shock protein, preferably hsp70.

In any or all of the aforementioned aspects of the invention, the infectious disease antigen may be derived from an infectious agent such as a bacterium, virus, protozoan, mycoplasma, fungus, yeast, parasite, or prion, by way of non-limiting example. A cancer or tumor antigen associated with cancer may be derived from a sarcoma, a lymphoma, a leukemia, or a carcinoma, a melanoma, carcinoma of the breast, carcinoma of the prostate, ovarian carcinoma, carcinoma of the cervix, colon carcinoma, carcinoma of the lung, glioblastoma, or astrocytoma, by way of non-limiting examples. The antigenic domain of an infectious agent or cancer comprises an antigen derived from or associated with the infectious disease or tumor antigen, such that induction of an immune response to the antigen of the infectious agent or cancer antigen, respectively, is useful for treating the corresponding infectious disease or cancer.

This application claims priority under 35 U.S.C. § 119(e) to provisional applications 60/447,142, filed Feb. 13, 2003; 60/462,469, filed Apr. 11, 2003; 60/463,746, filed Apr. 18, 2003; and 60/503,417, filed Sep. 16, 2003, all four of which are incorporated herein by reference in their entireties.

DETAILED DESCRIPTION OF THE INVENTION

Figure 1:
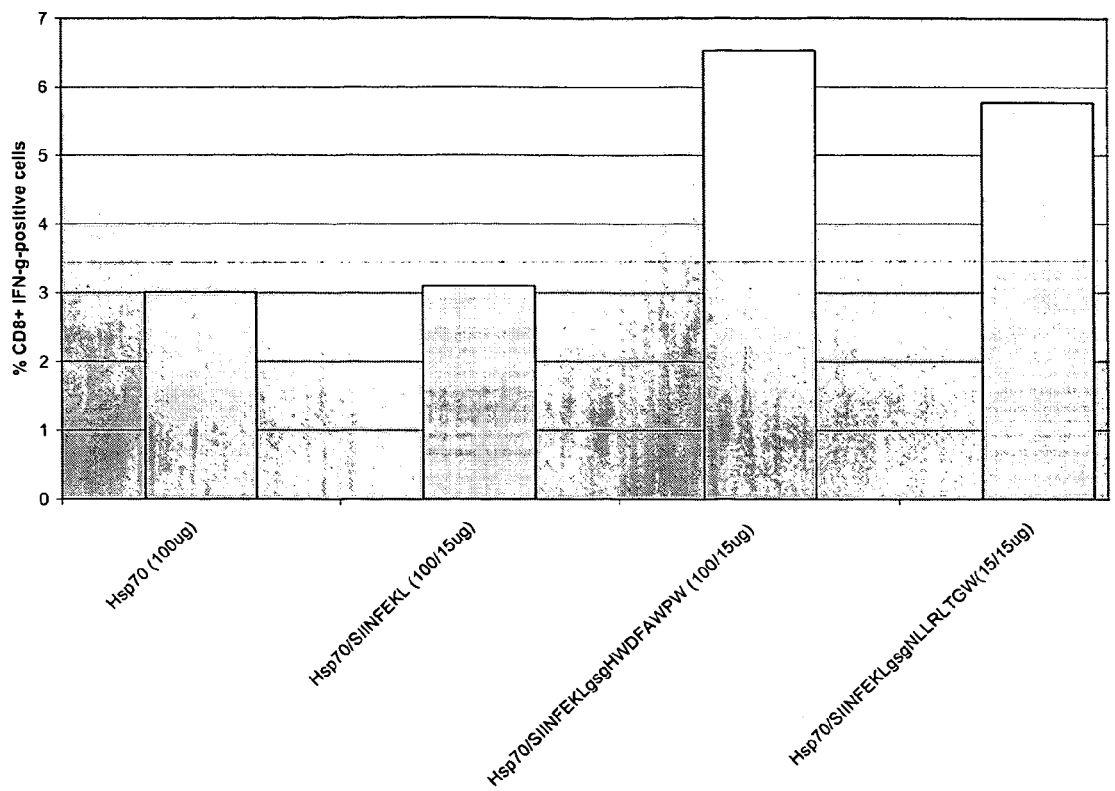
FIG. 1 shows the induction of an in-vivo immune response with several hybrid antigens of the invention in a complex with hsp70. CD8+ T cells isolated from mice immunized with hsp70 alone, hsp70 complexed to the epitope SIINFEKL (SEQ ID NO:357), hsp70 complexed to the hybrid antigen SIINFEKLGSGHWDFAWPW (SEQ ID NO:368), or hsp70 complexed to the hybrid antigen SIINFEKLGSGNLLRLTGW (SEQ ID NO:367) were assayed for IFN-γ secretion.

For purposes of clarity of description, and not by way of limitation, the detailed description is divided into the following subsections:
(i) hybrid antigens,
(ii) heat shock proteins; and
(iii) methods of administration.

Hybrid Antigens

A hybrid antigen, according to the invention comprises an immunogenic (antigenic) domain as well as a heat shock protein-binding domain. An optional linker, preferably a peptide linker, may be provided between these domains. Thus, the hybrid antigen serves at least two functions, namely (i) it contains an epitope capable of inducing the desired immune response; and (ii) it is capable of physically binding to a heat shock protein. As will be noted below, such binding may occur in vivo such that administration of the hybrid antigen alone will induce the desired immune response and provide the desired therapeutic effect.

The term "antigen" as used herein, refers to a compound which may be composed of amino acids, carbohydrates, nucleic acids or lipids individually or in any combination.

The term "hybrid antigen," as used herein, refers to a compound which binds to one or more heat shock proteins and which is representative of the immunogen toward which an immune response is desirably directed. For example, where the immunogen is an influenza virus, the hybrid antigen may comprise a peptide fragment of the matrix protein of the influenza virus. As used herein, the term "immunogen" is applied to the neoplastic cell, infected cell, pathogen, or component thereof, towards which an immune response is to be elicited, whereas the hybrid antigen comprises a portion of that immunogen which can provoke the desired response and which binds to one or more heat shock proteins. In particular, the antigenic domain of the hybrid antigen is selected to elicit an immune response to a particular disease or pathogen, including peptides obtained from MHC molecules, mutated DNA gene products, and direct DNA products such as those obtained from tumor cells.

While the invention may be applied to any type of immunogen, immunogens of particular interest are those associated with, derived from, or predicted to be associated with a neoplastic disease, including but not limited to a sarcoma, a lymphoma, a leukemia, or a carcinoma, and in particular, with melanoma, carcinoma of the breast, carcinoma of the prostate, ovarian carcinoma, carcinoma of the cervix, colon carcinoma, carcinoma of the lung, glioblastoma, astrocytoma, etc. Selections of melanoma antigens useful in hybrid antigens of the present invention may be found, by way of non-limiting example, in PCT/US01/12449 (WO0178655), incorporated herein by reference in its entirety. Further, mutations of tumor suppressor gene products such as p53, or oncogene products such as ras may also provide hybrid antigens to be used according to the invention.

In further embodiments, the immunogen may be associated with an infectious disease, and, as such, may be a bacterium, virus, protozoan, mycoplasma, fungus, yeast, parasite, or prion. For example, but not by way of limitation, the immunogen may be a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, *Trypanosoma cruzi*, etc.

Immunogens may be obtained by isolation directly from a neoplasm, an infected cell, a specimen from an infected subject, a cell culture, or an organism culture, or may be synthesized by chemical or recombinant techniques. Suitable antigenic peptides, particularly for use in a hybrid antigen, for use against viruses, bacteria and the like can be designed by searching through their sequences for MHC class I restricted peptide epitopes containing HLA binding sequences such as but not limited to HLA-A2 peptide binding sequences:
Xaa(Leu/Met)XaaXaaXaa(Val/Ile/Leu/Thr)XaaXaa(Val/Leu) (SEQ ID NO:2), for example, from viruses:
Ser Gly Pro Ser Asn Thr Pro Glu Ile (SEQ ID NO:10);
Ser Gly Val Glu Asn Pro Gly Tyr Cys Leu (SEQ ID NO:11);
Lys Ala Val Tyr Asn Phe Ala Thr Cys Gly (SEQ ID NO:12);
Arg Pro Gln Ala Ser Gly Val Tyr Met (SEQ ID NO:13);
Phe Gln Pro Gln Asn Gly Gln Phe Ile (SEQ ID NO:14);
Ile Glu Gly Gly Trp Thr Gly Met Ile (SEQ ID NO:15);
Thr Tyr Val Ser Val Ser Thr Ser Thr Leu (SEQ ID NO:16);
Phe Glu Ala Asn Gly Asn Leu Ile (SEQ ID NO:17);
Ile Tyr Ser Thr Val Ala Ser Ser Leu (SEQ ID NO:18);
Thr Tyr Gln Arg Thr Arg Ala Leu Val (SEQ ID NO:19);
Cys Thr Glu Leu Lys Leu Ser Asp Tyr (SEQ ID NO:20);
Ser Asp Tyr Glu Gly Arg Leu Ile (SEQ ID NO:21);
Glu Glu Gly Ala Ile Val Gly Glu Ile (SEQ ID NO:22);
Val Ser Asp Gly Gly Pro Asn Leu Tyr (SEQ ID NO:23);
Ala Ser Asn Glu Asn Met Glu Thr Met (SEQ ID NO:24);
Ala Ser Asn Glu Asn Met Asp Ala Met (SEQ ID NO:25);
Lys Leu Gly Glu Phe Tyr Asn Gln Met Met (SEQ ID NO:26);
Leu Tyr Gln Asn Val Gly Thr Tyr Val (SEQ ID NO:27);
Thr Tyr Val Ser Val Gly Thr Ser Thr Leu (SEQ ID NO:28);
Phe Glu Ser Thr Gly Asn Leu Ile (SEQ ID NO:29);
Val Tyr Gln Ile Leu Ala Ile Tyr Ala (SEQ ID NO:30);
Ile Tyr Ala Thr Val Ala Gly Ser Leu (SEQ ID NO:31);
Gly Ile Leu Gly Phe Val Phe Thr Leu (SEQ ID NO:32);
Ile Leu Gly Phe Val Phe Thr Leu Thr Val (SEQ ID NO:33);
Ile Leu Arg Gly Ser Val Ala His Lys (SEQ ID NO:34);
Glu Asp Leu Arg Val Leu Ser Phe Ile (SEQ ID NO:35);
Glu Leu Arg Ser Arg Tyr Ala Ile (SEQ ID NO:36);
Ser Arg Thr Trp Ala Ile Arg Thr Arg (SEQ ID NO:37);
Lys Thr Gly Gly Pro Ile Tyr Lys Arg (SEQ ID NO:38);
Phe Ala Pro Gly Asn Tyr Pro Ala Leu (SEQ ID NO:39);
Arg Arg Tyr Pro Asp Ala Val Tyr Leu (SEQ ID NO:40);
Asp Pro Val Ile Asp Arg Leu Tyr Leu (SEQ ID NO:41);
Ser Pro Gly Arg Ser Phe Ser Tyr Phe (SEQ ID NO:42);

Tyr Pro Ala Leu Gly Leu His Glu Phe (SEQ ID NO:43);
Thr Tyr Lys Asp Thr Val Gln Leu (SEQ ID NO:44);
Phe Tyr Asp Gly Phe Ser Lys Val Pro Leu (SEQ ID NO:45);
Phe Ile Ala Gly Asn Ser Ala Tyr Glu Tyr Val (SEQ ID NO:46);
Tyr Pro His Met Pro Thr Asn Leu (SEQ ID NO:47);
Ala Pro Thr Ala Gly Ala Phe Phe Phe (SEQ ID NO:48);
Ser Thr Leu Pro Glu Thr Thr Val Val Arg Arg (SEQ ID NO:49);
Phe Leu Pro Ser Asp Phe Phe Pro Ser Val (SEQ ID NO:50);
Trp Leu Ser Leu Leu Val Pro Phe Val (SEQ ID NO:51);
Gly Leu Ser Pro Thr Val Trp Leu Ser Val (SEQ ID NO:52);
Asp Leu Met Gly Tyr Ile Pro Leu Val (SEQ ID NO:53);
Leu Met Gly Tyr Ile Pro Leu Val Gly Ala (SEQ ID NO:54);
Ala Ser Arg Cys Trp Val Ala Met (SEQ ID NO:55);
Lys Leu Val Ala Leu Gly Ile Asn Ala Val (SEQ ID NO:56);
Phe Leu Arg Gly Arg Ala Tyr Gly Leu (SEQ ID NO:57);
Arg Arg Ile Tyr Asp Leu Ile Glu Leu (SEQ ID NO:58);
Ile Val Thr Asp Phe Ser Val Ile Lys (SEQ ID NO:59);
Arg Arg Arg Trp Arg Arg Leu Thr Val (SEQ ID NO:60);
Glu Glu Asn Leu Leu Asp Phe Val Arg Phe (SEQ ID NO:61);
Cys Leu Gly Gly Leu Leu Thr Met Val (SEQ ID NO:62);
Ser Ser Ile Glu Phe Ala Arg Leu (SEQ ID NO:63);
Leu Tyr Arg Thr Phe Ala Gly Asn Pro Arg Ala (SEQ ID NO:64);
Asp Tyr Ala Thr Leu Gly Val Gly Val (SEQ ID NO:65);
Leu Leu Leu Gly Thr Leu Asn Ile Val (SEQ ID NO:66);
Leu Leu Met Gly Thr Leu Gly Ile Val (SEQ ID NO:67);
Thr Leu Gln Asp Ile Val Leu His Leu (SEQ ID NO:68);
Gly Leu His Cys Tyr Glu Gln Leu Val (SEQ ID NO:69);
Pro Leu Lys Gln His Phe Gln Ile Val (SEQ ID NO:70);
Arg Leu Val Thr Leu Lys Asp Ile Val (SEQ ID NO:71);
Arg Ala His Tyr Asn Ile Val Thr Phe (SEQ ID NO:72);
Leu Leu Phe Gly Tyr Pro Val Tyr Val (SEQ ID NO:73);
Ser Ala Ile Asn Asn Tyr Ala Gln Lys Leu (SEQ ID NO:74);
His Gln Ala Ile Ser Pro Arg Thr Leu (SEQ ID NO:75);
Gln Met Val His Gln Ala Ile Ser Pro Arg Thr Leu (SEQ ID NO:76);
Cys Lys Gly Val Asn Lys Glu Tyr Leu (SEQ ID NO:77);
Gln Gly Ile Asn Asn Leu Asp Asn Leu (SEQ ID NO:78);
Asn Asn Leu Asp Asn Asn Leu Arg Asp Tyr (SEQ ID NO:79);
Ser Glu Phe Leu Leu Glu Lys Arg Ile (SEQ ID NO:80);
Ser Tyr Ile Gly Ser Ile Asn Asn Ile (SEQ ID NO:81);
Ile Leu Gly Asn Lys Ile Val Arg Met Tyr (SEQ ID NO:82);
Arg Leu Arg Pro Gly Gly Lys Lys Lys (SEQ ID NO:83);
Glu Ile Lys Asp Thr Lys Glu Ala Leu (SEQ ID NO:84);
Gly Glu Ile Tyr Lys Arg Trp Ile Ile (SEQ ID NO:85);
Glu Ile Tyr Lys Arg Trp Ile Ile Leu (SEQ ID NO:86);
Arg Tyr Leu Lys Asp Gln Gln Leu Leu (SEQ ID NO:87);
Arg Gly Pro Gly Arg Ala Phe Val Thr Ile (SEQ ID NO:88);
Ile Val Gly Leu Asn Lys Ile Val Arg (SEQ ID NO:89);
Thr Val Tyr Tyr Gly Val Pro Val Trp Lys (SEQ ID NO:90);
Arg Leu Arg Asp Leu Leu Leu Ile Thr Arg (SEQ ID NO:91);
Lys Arg Trp Ile Leu Gly Leu Asn Lys (SEQ ID NO:92);
Ser Phe Asn Cys Gly Gly Glu Phe Phe (SEQ ID NO:93);
Gly Arg Ala Phe Val Thr Ile Gly Lys (SEQ ID NO:94);
Thr Pro Gly Pro Gly Val Arg Tyr Pro Leu (SEQ ID NO:95);
Gln Val Pro Leu Arg Pro Met Thr Lys (SEQ ID NO:96);
Thr Glu Met Glu Lys Glu Gly Lys Ile (SEQ ID NO:97);
Ile Leu Lys Glu Pro Val His Gly Val (SEQ ID NO:98);
Val Glu Ala Glu Ile Ala His Gln Ile (SEQ ID NO:99);
Arg Gly Tyr Val Tyr Gln Gly Leu (SEQ ID NO:100);
Tyr Ser Gly Tyr Ile Phe Arg Asp Leu (SEQ ID NO:101);
Val Gly Pro Val Phe Pro Gly Met (SEQ ID NO:102);
Ile Ile Tyr Arg Phe Leu Leu Ile (SEQ ID NO:103);

from bacteria:

Lys Tyr Gly Val Ser Val Gln Asp Ile (SEQ ID NO:104);
Ile Gln Val Gly Asn Thr Arg Thr Ile (SEQ ID NO:105);
Thr Pro His Pro Ala Arg Ile Gly Leu (SEQ ID NO:106);

from parasites:
Ser Tyr Ile Pro Ser Ala Glu Lys Ile (SEQ ID NO:107);
Lys Pro Lys Asp Glu Leu Asp Tyr (SEQ ID NO:108);
Lys Ser Lys Asp Glu Leu Asp Tyr (SEQ ID NO:109);
Lys Pro Asn Asp Lys Ser Leu Tyr (SEQ ID NO:110);
Lys Tyr Leu Lys Lys Ile Lys Asn Ser Leu (SEQ ID NO:111);
Tyr Glu Asn Asp Ile Glu Lys Lys Ile (SEQ ID NO:112);
Asn Tyr Asp Asn Ala Gly Thr Asn Leu (SEQ ID NO:113);
Asp Glu Leu Asp Tyr Glu Asn Asp Ile (SEQ ID NO:114);
Ser Tyr Val Pro Ser Ala Glu Gln Ile (SEQ ID NO:115);

from cancers:
Phe Glu Gln Asn Thr Ala Gln Pro (SEQ ID NO:116);
Phe Glu Gln Asn Thr Ala Gln Ala (SEQ ID NO:117);
Glu Ala Asp Pro Thr Gly His Ser Tyr (SEQ ID NO:118);
Glu Val Asp Pro Ile Gly His Leu Tyr (SEQ ID NO:119);
Ala Ala Gly Ile Gly Ile Leu Thr Val (SEQ ID NO:120);
Tyr Leu Glu Pro Gly Pro Val Thr Ala (SEQ ID NO:121);
Ile Leu Asp Gly Thr Ala Thr Leu Arg Leu (SEQ ID NO:122);
Met Leu Leu Ala Leu Leu Tyr Cys Leu (SEQ ID NO:123);
Tyr Met Asn Gly Thr Met Ser Gln Val (SEQ ID NO:124);
Leu Pro Tyr Leu Gly Trp Leu Val Phe (SEQ ID NO:125);
Phe Gly Pro Tyr Lys Leu Asn Arg Leu (SEQ ID NO:126);
Lys Ser Pro Trp Phe Thr Thr Leu (SEQ ID NO:127);
Gly Pro Pro His Ser Asn Asn Phe Gly Tyr (SEQ ID NO:128); and
Ile Ser Thr Gln Asn His Arg Ala Leu (SEQ ID NO:129);

(Rammensee et al., *Immunogenetics* 41:178-223 (1995)),
Xaa(Leu/Met)XaaXaaXaaXaaXaaXaaVal (SEQ ID NO:3)

(Tarpey et al., *Immunology* 81:222-227 (1994)),
Xaa(Val/Gln)XaaXaaXaaXaaXaaXaaLeu (SEQ ID NO:4), for example, from virus:
Tyr Gly Ile Leu Gly Lys Val Phe Thr Leu (SEQ ID NO:130);
Ser Leu Tyr Asn Thr Val Ala Thr Leu (SEQ ID NO:131);

(Barouch et al., *J. Exp. Med.* 182:1847-1856 (1995)).

The foregoing epitopes are merely exemplary of selections available associated with various infectious diseases and cancer, and are provided without any intent whatsoever to be limiting.

It may also be desirable to consider the type of immune response which is desired. For example, under certain circumstances, a humoral immune response may be appropriate. In other cases, and indeed where an immune response directed toward neoplastic cells or infected cells is sought to be elicited, a cellular immune response is particularly desirable. Accordingly, particular epitopes associated with the activation of B cells, T helper cells, or cytotoxic T cells may be identified and selected for incorporation into the hybrid antigen.

It may also be desirable to utilize hybrid antigen associated with an autoimmune disease or allergy. Such a hybrid antigen may be administered, together with one or more heat shock proteins, in an amount sufficient to be tolerogenic or to inhibit a pre-existing immune response to the hybrid antigen in a subject. The amount of heat shock protein required to inhibit the immune response is expected to be substantially greater than the amount required for stimulation.

Although the size of hybrid antigen may vary depending upon the heat shock protein used, in non-limiting embodiments of the invention, the hybrid antigen may be the size of a peptide having between 10 and 500 amino acid residues, and preferably be the size of a peptide having between 14 and 100, most preferably 18 and 50 amino acid residues. As such, it may be desirable to produce a fragment of an immunogen to serve as a hybrid antigen, or, alternatively, to synthesize a hybrid antigen by chemical or recombinant DNA methods.

Based on the foregoing considerations, a hybrid antigen may be prepared, and then tested for its ability to bind to heat shock protein. In some instances, binding of hybrid antigen to a particular heat shock protein may be facilitated by the presence of at least one other protein, which may be a heat shock protein.

For example, binding of hybrid antigen to a heat shock protein may be evaluated by labeling the hybrid antigen with a detectable label, such as a radioactive, fluorescent, enzymatic or pigmented label, combining the hybrid antigen with heat shock protein under conditions which would be expected to permit binding to occur, and then isolating the heat shock protein while removing any unbound hybrid antigen, and determining whether any labeled hybrid antigen had adhered to the heat shock protein. As a specific example, and not by way of limitation, the ability of a hybrid antigen to bind to BiP heat shock protein may be evaluated by combining 2 µg BiP with up to about 1150 pmole of radioactively labeled hybrid antigen in buffer containing 50 mM Tris HCl (pH 7.5), 200 mM NaCl, and 1 mM Na$_2$EDTA, in a final volume of 50 µl, for 30 minutes at 37 degrees Centigrade. Unbound hybrid antigen may then be removed from bound BiP-hybrid antigen by centrifugation at 100 g by desalting through a 1 ml Sephadex-G column for 2 minutes. Penefsky, *J. Biol. Chem.* 252: 2891 (1977). To prevent binding to the resin, columns may first be treated with 100 µl of bovine serum albumin in the same buffer and centrifuged as above. Bound hybrid antigen may then be quantitated by liquid scintillation counting. See Flynn et al., *Science* 245:385-390 (1989).

Because ATP hydrolysis drives the release of peptides from many known heat shock proteins, the amount of ATPase activity may often be used to quantitate the amount of hybrid antigen binding to heat shock protein. An example of how such an assay may be performed is set forth in Flynn et al., *Science* 245:385-390 (1989).

The heat shock protein-binding domain is selected so that the hybrid antigen will bind in vitro or in vivo to a heat shock protein such as BiP, hsp70, gp96, or hsp90, or a member of the foregoing heat shock protein families, alone or in combination with accessory heat shock proteins such as hsp40, or hsp60. Peptides which fulfill this criterion may be identified initially by panning libraries of antigens known to bind well to one or more heat shock proteins as described in Blond-Elguindi et al., *Cell* 75:717-728 (1993). Using this technique, Blond-Elguindi have concluded that the heat shock protein BiP recognizes polypeptides that contain a heptameric region having the sequence Hy(Trp/X)HyXHyXhy (SEQ ID NO:7)

where Hy represents a hydrophobic amino acid residue, particularly tryptophan, leucine or phenylalanine (SEQ ID NO:8), and X is any amino acid.

Other heat shock protein binding motifs have also been identified. For example, Auger et al., *Nature Medicine* 2:306-310 (1996) have identified two pentapeptide binding motifs Gln Lys Arg Ala Ala (SEQ ID NO:5) and Arg Arg Arg Ala Ala (SEQ ID NO:6)

in HLA-DR types associated with rheumatoid arthritis which bind to heat shock proteins. Heat shock binding motifs have also been identified as consisting of seven to fifteen residue long peptides which are enriched in hydrophobic amino acids. (Gragerov et al., *J. Molec. Biol.* 235:848-854 (1994)).

It has been found that incorporation of a tryptophan residue (Trp, or single amino acid code W) at the C-terminus of the heat shock protein binding domains such as but not limited to those identified as described above, enhances binding to heat shock proteins. Increased binding to heat shock proteins has been found to increase the ability of hybrid antigens to induce an immune response to the antigenic domain of the hybrid antigen, whether administered in a complex with a heat shock protein or when administered alone. Increased immune response is correlated with increased efficacy of treating disease.

Moreover, the addition of a tryptophan residue to the heat shock protein binding domain renders unto such peptides the ability to be detected or be better detected using ultraviolet light absorbance, and the detectability permits facile evaluation of the binding of the peptides to heat shock proteins, by methods such as but not limited to those described herein. Other examples of methods for determining affinity are described in PCT/US96/13363 (WO9706821), which is incorporated herein by reference in its entirety.

Non-limiting examples of such heat shock protein binding domains with a terminal Trp residue useful for the various aspects of the present invention include:

Asn Leu Leu Arg Leu Thr Gly Trp (SEQ ID NO:417);
Phe Tyr Gln Leu Ala Leu Tyr Trp (SEQ ID NO:418);
Arg Lys Leu Phe Phe Asn Leu Arg Trp (SEQ ID NO:419);
Gly Lys Trp Val Tyr Ile Gly Trp (SEQ ID NO:132);
Ala Lys Arg Glu Thr Lys Gly Trp (SEQ ID NO:133);
Lys Trp Val His Leu Phe Gly Trp (SEQ ID NO:134);
Arg Leu Val Leu Val Leu Gly Trp (SEQ ID NO:135);
Trp Lys Trp Gly Ile Tyr Gly Trp (SEQ ID NO:136);
Ser Ser His Ala Ser Ala Gly Trp (SEQ ID NO:137);
Trp Gly Pro Trp Ser Phe Gly Trp (SEQ ID NO:138);
Ala Ile Pro Gly Lys Val Gly Trp (SEQ ID NO:139);
Arg Val His Asp Pro Ala Gly Trp (SEQ ID NO:140);
Arg Ser Val Ser Ser Phe Gly Trp (SEQ ID NO:141);
Leu Gly Thr Arg Lys Gly Gly Trp (SEQ ID NO:142);
Lys Asp Pro Leu Phe Asn Gly Trp (SEQ ID NO:143);
Leu Ser Gln His Thr Asn Gly Trp (SEQ ID NO:144);
Asn Arg Leu Leu Leu Thr Gly Trp (SEQ ID NO:145);
Tyr Pro Leu Trp Val Ile Gly Trp (SEQ ID NO:146);
Leu Leu Ile Ile Asp Arg Gly Trp (SEQ ID NO:147);
Arg Val Ile Ser Leu Gln Gly Trp (SEQ ID NO:148);
Glu Val Ser Arg Glu Asp Gly Trp (SEQ ID NO:149);
Ser Ile Leu Arg Ser Thr Gly Trp (SEQ ID NO:150);
Pro Gly Leu Val Trp Leu Gly Trp (SEQ ID NO:151);
Val Lys Lys Leu Tyr Ile Gly Trp (SEQ ID NO:152);
Asn Asn Arg Leu Leu Asp Gly Trp (SEQ ID NO:153);
Ser Lys Gly Arg Trp Gly Gly Trp (SEQ ID NO:154);
Ile Arg Pro Ser Gly Ile Gly Trp (SEQ ID NO:155);
Ala Ser Leu Cys Pro Thr Gly Trp (SEQ ID NO:156);
Asp Val Pro Gly Leu Arg Gly Trp (SEQ ID NO:157);
Arg His Arg Glu Val Gln Gly Trp (SEQ ID NO:158);
Leu Ala Arg Lys Arg Ser Gly Trp (SEQ ID NO:159);
Ser Val Leu Asp His Val Gly Trp (SEQ ID NO:160);
Asn Leu Leu Arg Arg Ala Gly Trp (SEQ ID NO:161);
Ser Gly Ile Ser Ala Trp Gly Trp (SEQ ID NO:162);
Phe Tyr Phe Trp Val Arg Gly Trp (SEQ ID NO:163);
Lys Leu Phe Leu Pro Leu Gly Trp (SEQ ID NO:164);
Thr Pro Thr Leu Ser Asp Gly Trp (SEQ ID NO:165);
Thr His Ser Leu Ile Leu Gly Trp (SEQ ID NO:166);
Leu Leu Leu Leu Ser Arg Gly Trp (SEQ ID NO:167);
Leu Leu Arg Val Arg Ser Gly Trp (SEQ ID NO:168);
Glu Arg Arg Ser Arg Gly Gly Trp (SEQ ID NO:169);
Arg Met Leu Gln Leu Ala Gly Trp (SEQ ID NO:170);
Arg Gly Trp Ala Asn Ser Gly Trp (SEQ ID NO:171);
Arg Pro Phe Tyr Ser Tyr Gly Trp (SEQ ID NO:172);

Ser Ser Ser Trp Asn Ala Gly Trp (SEQ ID NO:173);
Leu Gly His Leu Glu Glu Gly Trp (SEQ ID NO:174);
Ser Ala Val Thr Asn Thr Gly Trp (SEQ ID NO:175);
Leu Arg Arg Ala Ser Leu Trp (SEQ ID NO:176);
Leu Arg Arg Trp Ser Leu Trp (SEQ ID NO:177);
Lys Trp Val His Leu Phe Trp (SEQ ID NO:178);
Asn Arg Leu Leu Leu Thr Trp (SEQ ID NO:179);
Ala Arg Leu Leu Leu Thr Trp (SEQ ID NO:180);
Asn Ala Leu Leu Leu Thr Trp (SEQ ID NO:181);
Asn Arg Leu Ala Leu Thr Trp (SEQ ID NO:182);
Asn Leu Leu Arg Leu Thr Trp (SEQ ID NO:183);
Asn Arg Leu Trp Leu Thr Trp (SEQ ID NO:184); and
Asn Arg Leu Leu Leu Ala Trp (SEQ ID NO:185);

Other heat shock protein binding domains useful in the practice of the present invention include Phe Tyr Gln Leu Ala Leu Thr Trp (SEQ ID NO: 186), Phe Tyr Gln Leu Ala Leu Thr Trp (SEQ ID NO:187), Arg Lys Leu Phe Phe Asn Leu Arg Trp (SEQ ID NO:188), Arg Lys Leu Phe Phe Asn Leu Arg Trp (SEQ ID NO: 189), Lys Phe Glu Arg Gln Trp (SEQ ID NO:190), Asn Ile Val Arg Lys Lys Lys Trp (SEQ ID NO:191), and Arg Gly Tyr Val Tyr Gln Gly Leu Trp (SEQ ID NO:192).

Moreover, other heat shock protein binding domains include those described in WO9922761, and may have a terminal Trp residue added to achieve the purposes of the present invention. Xaa represents any amino acid.

Tyr Thr Leu Val Gln Pro Leu Trp (SEQ ID NO:193);
Thr Pro Asp Ile Thr Pro Lys Trp (SEQ ID NO:194);
Thr Tyr Pro Asp Leu Arg Tyr Trp (SEQ ID NO:195);
Asp Arg Thr His Ala Thr Ser Trp (SEQ ID NO:196);
Met Ser Thr Thr Phe Tyr Ser Trp (SEQ ID NO:197);
Tyr Gln His Ala Val Gln Thr Trp (SEQ ID NO:198);
Phe Pro Phe Ser Ala Ser Thr Trp (SEQ ID NO:199);
Ser Ser Phe Pro Pro Leu Asp Trp (SEQ ID NO:200);
Met Ala Pro Ser Pro Pro His Trp (SEQ ID NO:201);
Ser Ser Phe Pro Asp Leu Leu Trp (SEQ ID NO:202);
His Ser Tyr Asn Arg Leu Pro Trp (SEQ ID NO:203);
His Leu Thr His Ser Gln Arg Trp (SEQ ID NO:204);
Gln Ala Ala Gln Ser Arg Ser Trp (SEQ ID NO:205);
Phe Ala Thr His His Ile Gly Trp (SEQ ID NO:206);
Ser Met Pro Glu Pro Leu Ile Trp (SEQ ID NO:207);
Ile Pro Arg Tyr His Leu Ile Trp (SEQ ID NO:208);
Ser Ala Pro His Met Thr Ser Trp (SEQ ID NO:209);
Lys Ala Pro Val Trp Ala Ser Trp (SEQ ID NO:210);
Leu Pro His Trp Leu Leu Ile Trp (SEQ ID NO:211);
Ala Ser Ala Gly Tyr Gln Ile Trp (SEQ ID NO:212);
Val Thr Pro Lys Thr Gly Ser Trp (SEQ ID NO:213);
Glu His Pro Met Pro Val Leu Trp (SEQ ID NO:214);
Val Ser Ser Phe Val Thr Ser Trp (SEQ ID NO:215);
Ser Thr His Phe Thr Trp Pro Trp (SEQ ID NO:216);
Gly Gln Trp Trp Ser Pro Asp Trp (SEQ ID NO:217);
Gly Pro Pro His Gln Asp Ser Trp (SEQ ID NO:218);
Asn Thr Leu Pro Ser Thr Ile Trp (SEQ ID NO:219);
His Gln Pro Ser Arg Trp Val Trp (SEQ ID NO:220);
Tyr Gly Asn Pro Leu Gln Pro Trp (SEQ ID NO:221);
Phe His Trp Trp Trp Gln Pro Trp (SEQ ID NO:222);
Ile Thr Leu Lys Tyr Pro Leu Trp (SEQ ID NO:223);
Phe His Trp Pro Trp Leu Phe Trp (SEQ ID NO:224);
Thr Ala Gln Asp Ser Thr Gly Trp (SEQ ID NO:225);
Phe His Trp Trp Trp Gln Pro Trp (SEQ ID NO:226);
Phe His Trp Trp Asp Trp Trp Trp (SEQ ID NO:227);
Glu Pro Phe Phe Arg Met Gln Trp (SEQ ID NO:228);
Thr Trp Trp Leu Asn Tyr Arg Trp (SEQ ID NO:229);
Phe His Trp Trp Trp Gln Pro Trp (SEQ ID NO:230);
Gln Pro Ser His Leu Arg Trp (SEQ ID NO:231);
Ser Pro Ala Ser Pro Val Tyr Trp (SEQ ID NO:232);
Phe His Trp Trp Trp Gln Pro Trp (SEQ ID NO:233);
His Pro Ser Asn Gln Ala Ser Trp (SEQ ID NO:234);
Asn Ser Ala Pro Arg Pro Val Trp (SEQ ID NO:235);
Gln Leu Trp Ser Ile Tyr Pro Trp (SEQ ID NO:236);
Ser Trp Pro Phe Phe Asp Leu Trp (SEQ ID NO:237);
Asp Thr Thr Leu Pro Leu His Trp (SEQ ID NO:238);
Trp His Trp Gln Met Leu Trp Trp (SEQ ID NO:239);
Asp Ser Phe Arg Thr Pro Val Trp (SEQ ID NO:240);
Thr Ser Pro Leu Ser Leu Leu Trp (SEQ ID NO:241);
Ala Tyr Asn Tyr Val Ser Asp Trp (SEQ ID NO:242);
Arg Pro Leu His Asp Pro Met Trp (SEQ ID NO:243);
Trp Pro Ser Thr Thr Leu Phe Trp (SEQ ID NO:244);
Ala Thr Leu Glu Pro Val Arg Trp (SEQ ID NO:245);
Ser Met Thr Val Leu Arg Pro Trp (SEQ ID NO:246);
Gln Ile Gly Ala Pro Ser Trp Trp (SEQ ID NO:247);
Ala Pro Asp Leu Tyr Val Pro Trp (SEQ ID NO:248);
Arg Met Pro Pro Leu Leu Pro Trp (SEQ ID NO:249);
Ala Lys Ala Thr Pro Glu His Trp (SEQ ID NO:250);
Thr Pro Pro Leu Arg Ile Asn Trp (SEQ ID NO:251);
Leu Pro Ile His Ala Pro His Trp (SEQ ID NO:252);
Asp Leu Asn Ala Tyr Thr His Trp (SEQ ID NO:253);
Val Thr Leu Pro Asn Phe His Trp (SEQ ID NO:254);
Asn Ser Arg Leu Pro Thr Leu Trp (SEQ ID NO:255);
Tyr Pro His Pro Ser Arg Ser Trp (SEQ ID NO:256);
Gly Thr Ala His Phe Met Tyr Trp (SEQ ID NO:257);
Tyr Ser Leu Leu Pro Thr Arg Trp (SEQ ID NO:258);
Leu Pro Arg Arg Thr Leu Leu Trp (SEQ ID NO:259);
Thr Ser Thr Leu Leu Trp Lys Trp (SEQ ID NO:260);
Thr Ser Asp Met Lys Pro His Trp (SEQ ID NO:261);
Thr Ser Ser Tyr Leu Ala Leu Trp (SEQ ID NO:262);
Asn Leu Tyr Gly Pro His Asp Trp (SEQ ID NO:263);
Leu Glu Thr Tyr Thr Ala Ser Trp (SEQ ID NO:264);
Ala Tyr Lys Ser Leu Thr Gln Trp (SEQ ID NO:265);
Ser Thr Ser Val Thr Ser Ser Trp (SEQ ID NO:266);
Glu Gly Pro Leu Arg Ser Pro Trp (SEQ ID NO:267);
Thr Thr Tyr His Ala Leu Gly Trp (SEQ ID NO:268);
Val Ser Ile Gly His Pro Ser Trp (SEQ ID NO:269);
Thr His Ser His Arg Pro Ser Trp (SEQ ID NO:270);
Ile Thr Asn Pro Leu Thr Thr Trp (SEQ ID NO:271);
Ser Ile Gln Ala His His Ser Trp (SEQ ID NO:272);
Leu Asn Trp Pro Arg Val Leu Trp (SEQ ID NO:273);
Tyr Tyr Tyr Ala Pro Pro Pro Trp (SEQ ID NO:274);
Ser Leu Trp Thr Arg Leu Pro Trp (SEQ ID NO:275);
Asn Val Tyr His Ser Ser Leu Trp (SEQ ID NO:276);
Asn Ser Pro His Pro Thr Trp (SEQ ID NO:277);
Val Pro Ala Lys Pro Arg His Trp (SEQ ID NO:278);
His Asn Leu His Pro Asn Arg Trp (SEQ ID NO:279);
Tyr Thr Thr His Arg Trp Leu Trp (SEQ ID NO:280);
Ala Val Thr Ala Ala Ile Val Trp (SEQ ID NO:281);
Thr Leu Met His Asp Arg Val Trp (SEQ ID NO:282);
Thr Pro Leu Lys Val Pro Tyr Trp (SEQ ID NO:283);
Phe Thr Asn Gln GLn Tyr His Trp (SEQ ID NO:284);
Ser His Val Pro Ser Met Ala Trp (SEQ ID NO:285);
His Thr Thr Val Thr Gly Ala Trp (SEQ ID NO:286);
Thr Glu Thr Pro Tyr Pro Thr Trp (SEQ ID NO:287);
Leu Thr Thr Pro Phe Ser Ser Trp (SEQ ID NO:288);
Gly Val Pro Leu Thr Met Asp Trp (SEQ ID NO:289);
Lys Leu Pro Thr Val Leu Arg Trp (SEQ ID NO:290);
Cys Arg Phe His Gly Asn Arg Trp (SEQ ID NO:291);
Tyr Thr Arg Asp Phe Glu Ala Trp (SEQ ID NO:292);
Ser Ser Ala Ala Gly Pro Arg Trp (SEQ ID NO:293);
Ser Leu Ile Gln Tyr Ser Arg Trp (SEQ ID NO:294);
Asp Ala Leu Met Trp Pro XAA Trp (SEQ ID NO:295);
Ser Ser XAA Ser Leu Tyr Ile Trp (SEQ ID NO:296);
Phe Asn Thr Ser Thr Arg Thr Trp (SEQ ID NO:297);
Thr Val Gln His Val Ala Phe Trp (SEQ ID NO:298);
Asp Tyr Ser Phe Pro Pro Leu Trp (SEQ ID NO:299);
Val Gly Ser Met Glu Ser Leu Trp (SEQ ID NO:300);
Phe XAA Pro Met Ile XAA Ser Trp (SEQ ID NO:301);

Ala Pro Pro Arg Val Thr Met Trp (SEQ ID NO:302);
Ile Ala Thr Lys Thr Pro Lys Trp (SEQ ID NO:303);
Lys Pro Pro Leu Phe Gln Ile Trp (SEQ ID NO:304);
Tyr His Thr Ala His Asn Met Trp (SEQ ID NO:305);
Ser Tyr Ile Gln Ala Thr His Trp (SEQ ID NO:306);
Ser Ser Phe Ala Thr Phe Leu Trp (SEQ ID NO:307);
Thr Thr Pro Pro Asn Phe Ala Trp (SEQ ID NO:308);
Ile Ser Leu Asp Pro Arg Met Trp (SEQ ID NO:309);
Ser Leu Pro Leu Phe Gly Ala Trp (SEQ ID NO:310);
Asn Leu Leu Lys Thr Thr Leu Trp (SEQ ID NO:311);
Asp Gln Asn Leu Pro Arg Arg Trp (SEQ ID NO:312);
Ser His Phe Glu Gln Leu Leu Trp (SEQ ID NO:313);
Thr Pro Gln Leu His His Gly Trp (SEQ ID NO:314);
Ala Pro Leu Asp Arg Ile Thr Trp (SEQ ID NO:315);
Phe Ala Pro Leu Ile Ala His Trp (SEQ ID NO:316);
Ser Trp Ile Gln Thr Phe Met Trp (SEQ ID NO:317);
Asn Thr Trp Pro His Met Tyr Trp (SEQ ID NO:318);
Glu Pro Leu Pro Thr Thr Leu Trp (SEQ ID NO:319);
His Gly Pro His Leu Phe Asn Trp (SEQ ID NO:320);
Tyr Leu Asn Ser Thr Leu Ala Trp (SEQ ID NO:321);
His Leu His Ser Pro Ser Gly Trp (SEQ ID NO:322);
Thr Leu Pro His Arg Leu Asn Trp (SEQ ID NO:323);
Ser Ser Pro Arg Glu Val His Trp (SEQ ID NO:324);
Asn Gln Val Asp Thr Ala Arg Trp (SEQ ID NO:325);
Tyr Pro Thr Pro Leu Leu Thr Trp (SEQ ID NO:326);
His Pro Ala Ala Phe Pro Trp Trp (SEQ ID NO:327);
Leu Leu Pro His Ser Ser Ala Trp (SEQ ID NO:328);
Leu Glu Thr Tyr Thr Ala Ser Trp (SEQ ID NO:329);
Lys Tyr Val Pro Leu Pro Pro Trp (SEQ ID NO:330);
Ala Pro Leu Ala Leu His Ala Trp (SEQ ID NO:331);
Tyr Glu Ser Leu Leu Thr Lys Trp (SEQ ID NO:332);
Ser His Ala Ala Ser Gly Thr Trp (SEQ ID NO:333);
Gly Leu Ala Thr Val Lys Ser Trp (SEQ ID NO:334);
Gly Ala Thr Ser Phe Gly Leu Trp (SEQ ID NO:335);
Lys Pro Pro Gly Pro Val Ser Trp (SEQ ID NO:336);
Thr Leu Tyr Val Ser Gly Asn Trp (SEQ ID NO:337);
His Ala Pro Phe Lys Ser Gln Trp (SEQ ID NO:338);
Val Ala Phe Thr Arg Leu Pro Trp (SEQ ID NO:339);
Leu Pro Thr Arg Thr Pro Ala Trp (SEQ ID NO:340);
Ala Ser Phe Asp Leu Leu Ile Trp (SEQ ID NO:341);
Arg Met Asn Thr Glu Pro Pro Trp (SEQ ID NO:342);
Lys Met Thr Pro Leu Thr Thr Trp (SEQ ID NO:343);
Ala Asn Ala Thr Pro Leu Leu Trp (SEQ ID NO:344);
Thr Ile Trp Pro Pro Pro Val Trp (SEQ ID NO:345);
Gln Thr Lys Val Met Thr Thr Trp (SEQ ID NO:346);
Asn His Ala Val Phe Ala Ser Trp (SEQ ID NO:347);
Leu His Ala Ala Xaa Thr Ser Trp (SEQ ID NO:348);
Thr Trp Gln Pro Tyr Phe His Trp (SEQ ID NO:349);
Ala Pro Leu Ala Leu His Ala Trp (SEQ ID NO:350);
Thr Ala His Asp Leu Thr Val Trp (SEQ ID NO:351);
Asn Met Thr Asn Met Leu Thr Trp (SEQ ID NO:352);
Gly Ser Gly Leu Ser Gln Asp Trp (SEQ ID NO:353);
Thr Pro Ile Lys Thr Ile Tyr Trp (SEQ ID NO:354);
Ser His Leu Tyr Arg Ser Ser Trp (SEQ ID NO:355); and
His Gly Gln Ala Trp Gln Phe Trp (SEQ ID NO:356);

The aforementioned heat shock protein binding domains are merely exemplary of various peptides, among peptide and non-peptide heat shock protein binding molecules, that may be used in the practice of the present invention.

The hybrid antigen of the invention incorporates one immunogenic domain and one heat shock protein-binding domain, optionally separated by a peptide linker. The hybrid antigen of the invention may be synthesized using chemical peptide synthesis methods or it can be synthesized by expression of a nucleic acid construct containing linked sequences encoding the antigenic and heat shock protein binding domains. One suitable technique utilizes initial separate PCR amplification reactions to produce separate DNA segments encoding the two domains, each with a linker segment attached to one end, followed by fusion of the two amplified products in a further PCR step. This technique is referred to as linker tailing. Suitable restriction sites may also be engineered into regions of interest, after which restriction digestion and ligation is used to produce the desired hybrid antigen-encoding sequence.

As noted herein, the nucleic acid encoding a hybrid antigen of the invention is also suitable for therapeutic use by administration to the subject, where expression in vivo yields the hybrid antigen with the ability of inducing an immune response.

In addition to the studies on various heat shock protein binding domains and hybrid antigens containing them which are described above and in the Examples below, further comparative studies on heat shock protein binding domains, set forth using single-letter amino acid codes, HWDFAWPW (SEQ ID NO:358) and NLLRLTGW (SEQ ID NO:359) were performed in vitro and in vivo, using the model epitope SIINFEKL (SEQ ID NO:357) from ovalbumin. As mentioned above, antigenic peptides complexed to heat shock proteins (HSPs) are able to enter the endogenous antigen processing pathway and prime CD8+ cytotoxic T lymphocytes (CTLs). It was determined as mentioned above that the co-linear synthesis of a hybrid antigen containing a class I MHC binding epitope and an HSP70-binding sequence (HWDFAWPW) (SEQ ID NO:358) as well as other heat shock protein-binding sequences could render immunogenic otherwise poorly binding epitopes. This has been confirmed and extended by demonstrating that a higher-affinity HSP70-binding sequence (NLLRLTGW) (SEQ ID NO:359) can further enhance the immunogenicity of the bound class I epitope. A competition binding assay revealed a dissociation constant that was 15-fold lower for the H2-Kb ovalbumin SIINFEKL (SEQ ID NO:357) epitope in hybrid antigen SIINFEKLGSGNLLRLTGW (SEQ ID NO:367) compared to hybrid antigen SIINFEKLGSGHWDFAWPW (SEQ ID NO:368), indicating a higher affinity of NLLRLTGW (SEQ ID NO:359) for HSP70. After confirming the ability of the HSP70-bound SIINFEKLGSGNLLRLTGW (SEQ ID NO:367) peptide to be processed and presented by murine macrophages in vitro, in-vivo immunogenicity was assessed. The in-vivo comparative evaluation of HSP70: SIINFEKLGSGNLLRLTGW (SEQ ID NO:367) vs. HSP70: SIINFEKLGSGHWDFAWPW (SEQ ID NO:368) complexes was performed by immunizing normal C57BL/6 mice, and the SIINFEKLGSGNLLRLTGW (SEQ ID NO:367) complexes were found to induce better CD8+ T cell responses. In a related experiment, NLLRLTGW (SEQ ID NO:359) alone was found to prevent induction of an immune response by the otherwise-immunogenic HSP70: SIINFEKLGSGHWDFAWPW (SEQ ID NO:368) mixture, an indication that NLLRLTGW (SEQ ID NO:359) blocks complex formation by interacting with the same binding site on HSP70. It was hypothesized, for which Applicants have no duty to disclose nor are bound thereto, that the lower dissociation constant for epitopes containing NLLRLTGW (SEQ ID NO:359) would cause complexes made with HSP70 to be more efficient as immunizing agents. Indeed, it was found that animals immunized one time with a low dose of HSP70: SIINFEKLGSGNLLRLTGW (SEQ ID NO:367) complexes induced peptide specific CD8+ T cells to secrete substantial levels of IFN-gamma in an ex vivo ELISPOT assay. Taken together, these data establish a positive correlation between the HSP70 binding affinity of the heat shock protein-binding domain-epitope hybrid antigen and immune responses, demonstrating that smaller amounts of defined epitopes can be used with a higher affinity heat shock protein binding domain such as but not limited to NLLRLTGW (SEQ ID NO:359) to successfully immunize in vivo. Other heat shock protein binding domains terminated in a Trp residue were also found to have improved binding properties.

Heat Shock Proteins

The term "heat shock protein," as used herein, refers to any protein which exhibits increased expression in a cell when the cell is subjected to a stress. In preferred non-limiting embodiments, the heat shock protein is originally derived from a eukaryotic cell; in more preferred embodiments, the heat shock protein is originally derived from a mammalian cell. For example, but not by way of limitation, heat shock proteins which may be used according to the invention include BiP (also referred to as grp78), hsp70, hsc70, gp96 (grp94), hsp60, hsp40, and hsp90, and members of the families thereof. Especially preferred heat shock proteins are BiP, gp96, and hsp70, as exemplified below. Most preferred is a member of the hsp70 family. Naturally occurring or recombinantly derived mutants of heat shock proteins may also be used according to the invention. For example, but not by way of limitation, the present invention provides for the use of heat shock proteins mutated so as to facilitate their secretion from the cell (for example having mutation or deletion of an element which facilitates endoplasmic reticulum recapture, such as KDEL (SEQ ID NO:9) or its homologues; such mutants are described in PCT Application No. PCT/US96/13233 (WO 97/06685), which is incorporated herein by reference).

For embodiments of the invention wherein heat shock protein and hybrid antigen are directly administered to the subject in the form of a protein/peptide complex, the heat shock protein may be prepared, using standard techniques, from natural sources, for example as described in Flynn et al., *Science* 245:385-390 (1989), or using recombinant techniques such as expression of a heat shock encoding vector in a suitable host cell such as a bacterial, yeast or mammalian cell. If pre-loading of the heat shock protein with peptides from the host organism is a concern, the heat shock protein can be incubated with ATP and then repurified. Non-limiting examples of methods for preparing recombinant heat shock proteins are set forth below.

A nucleic acid encoding a heat shock protein may be operatively linked to elements necessary or desirable for expression and then used to express the desired heat shock protein as either a means to produce heat shock protein for use in a protein vaccine or, alternatively, in a nucleic acid vaccine. Elements necessary or desirable for expression include, but are not limited to, promoter/enhancer elements, transcriptional start and stop sequences, polyadenylation signals, translational start and stop sequences, ribosome binding sites, signal sequences and the like. For example, but not by way of limitation, genes for various heat shock proteins have been cloned and sequenced, including, but not limited to, gp96 (human: Genebank Accession No. X15187; Maki et al., *Proc. Natl. Acad. Sci. U.S.A.* 87:5658-5562 (1990); mouse: Genebank Accession No. M16370; Srivastava et al., *Proc. Natl. Acad. Sci. U.S.A.* 84:3807-3811 (1987)), BiP (mouse: Genebank Accession No. U16277; Haas et al., *Proc. Natl. Acad. Sci. U.S.A.* 85:2250-2254 (1988); human: Genebank Accession No. M19645; Ting et al., *DNA* 7:275-286 (1988)), hsp70 (mouse: Genebank Accession No. M35021; Hunt et al., *Gene* 87:199-204 (1990); human: Genebank Accession No. M24743; Hunt et al, *Proc. Natl. Acad. Sci. U.S.A.* 82:6455-6489 (1995)), and hsp40 (human: Genebank Accession No. D49547; Ohtsuka K., *Biochem. Biophys. Res. Commun.* 197: 235-240 (1993)).

Methods of Administration

The hybrid antigens of the invention or complexes of hybrid antigens and heat shock proteins may be administered to a subject using either a peptide-based, protein-based or nucleic acid vaccine, so as to produce, in the subject, an amount of complex which is effective in inducing a therapeutic immune response in the subject.

The subject may be a human or nonhuman subject.

The term "therapeutic immune response," as used herein, refers to an increase in humoral and/or cellular immunity, as measured by standard techniques, which is directed toward the hybrid antigen. Preferably, but not by way of limitation, the induced level of humoral immunity directed toward hybrid antigen is at least four-fold, and preferably at least 16-fold greater than the levels of the humoral immunity directed toward the antigen prior to the administration of the compositions of this invention to the subject. The immune response may also be measured qualitatively, by means of a suitable in vitro or in vivo assay, wherein an arrest in progression or a remission of neoplastic or infectious disease in the subject is considered to indicate the induction of a therapeutic immune response.

Specific amounts of heat shock protein/hybrid antigen administered may depend on numerous factors including the immunogenicity of the particular vaccine composition, the immunocompetence of the subject, the size of the subject and the route of administration. Determining a suitable amount of any given composition for administration is a matter of routine screening.

Furthermore, significant immunological efficacy was identified in studies in which the hybrid antigen was administered alone, i.e., without heat shock protein. While Applicants have no duty to disclose the theory by which the invention operates, and are not bound thereto, the results of these studies suggest that the hybrid antigens, upon injection into the subject, bind to endogenous heat shock proteins, and thus do not require the concomitant administration of heat shock protein for effectiveness. The present invention extends to such utilities of the hybrid antigens of the invention, and moreover, to concomitant therapies or treatments that increase endogenous heat shock protein levels systemically or at the intended site of administration of the hybrid antigens of the invention. Such concomitant therapies or treatments include but are not limited to local application of heat or local or systemic pharmaceutical agents that increase the expression of heat shock protein in the local tissue. Such agents and methods are known in the art.

Hybrid antigens that are administered in the absence of co-administration of a heat shock protein (i.e., administered not in a complex with a heat shock protein) that comprise at least one antigenic domain and at least one heat shock protein binding domain preferably comprise one of the heat shock protein binding domains described herein, and more preferably are hybrid antigens comprising the heat shock protein binding domains Asn Leu Leu Arg Leu Thr Gly Trp (SEQ ID NO:417), Phe Tyr Gln Leu Ala Leu Tyr Trp (SEQ ID NO:418), or Arg Lys Leu Phe Phe Asn Leu Arg Trp (SEQ ID NO:419). Other selections include those mentioned hereinabove.

In specific non-limiting embodiments of the invention, it may be desirable to include more than one species of heat shock protein, and/or more than one hybrid antigen, in order to optimize the immune response. Such an approach may be particularly advantageous in the treatment of cancer or in the treatment of infections characterized by the rapid development of mutations that result in evasion of the immune response. Moreover, a hybrid antigen of the invention may include more than one immunogenic domain or more than one epitope.

Compositions comprising hybrid antigen/heat shock protein or hybrid antigen alone as set forth above are referred to herein as "vaccines." The term vaccine is used to indicate that the compositions of the invention may be used to induce a therapeutic immune response. A vaccine of the invention may comprise a hybrid antigen with a single antigenic domain or epitope, or a hybrid antigen with a plurality of antigenic domains or epitopes. Further, a vaccine may comprise an admixture of hybrid antigens with single or pluralities of antigenic domains or epitopes, or any combination of the foregoing. As noted above, the hybrid antigens or admixtures thereof may be complexed with one or more heat shock proteins before administration, or may be administered without heat shock protein.

A vaccine composition comprising one or more hybrid antigens optionally complexed to one or more heat shock proteins in accordance with the invention may be administered cutaneously, subcutaneously, intradermally, intravenously, intramuscularly, parenterally, intrapulmonarily, intravaginally, intrarectally, nasally or topically. The vaccine composition may be delivered by injection, particle bombardment, orally or by aerosol.

Incubation of heat shock proteins in solution with the hybrid antigen is sufficient to achieve loading of the antigen onto the heat shock protein in most cases. It may be desirable in some cases, however, to add agents which can assist in the loading of the antigen.

Incubation with heating of the heat shock protein with the hybrid antigen will in general lead to loading of the antigen onto the heat shock protein. In some cases, however, it may be desirable to add additional agents to assist in the loading. For example, hsp40 can facilitate loading of peptides onto hsp70. Minami et al., *J. Biol. Chem.* 271:19617-19624 (1996). Denaturants such as guanidinium HCl or urea can be employed to partially and reversibly destabilize the heat shock protein to make the peptide binding pocket more accessible to the antigen.

Vaccine compositions in accordance with the invention may further include various additional materials, such as a pharmaceutically acceptable carrier. Suitable carriers include any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

In particular, a vaccine of the invention comprising a heat shock protein preferably also include adenosine diphosphate (ADP), to promote the association between the heat shock protein and the heat shock protein binding domain prior to the complex reaching its destination. Other compounds with similar capabilities may used, alone or in combination with ADP.

The vaccine composition of the invention may also include suitable diluents, preservatives, solubilizers, emulsifiers, adjuvants and/or carriers. Such compositions may be in the form of liquid or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g. glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexing with metal ions, or incorporation of the material into or onto particulate preparations of polymeric compounds such as polylactic acid, polyglycolic acid, hydrogels, etc. or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the vaccine. For example, a product derived from a membrane-bound form of a protein may require a formulation containing detergent. Controlled or sustained release compositions include formulation in lipophilic depots (e.g. fatty acids, waxes, oils). Also comprehended by the invention are particulate compositions coated with polymers (e.g. poloxamers or poloxamines) and coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including intramuscular, parenteral, pulmonary, nasal and oral.

As an alternative to direct administration of the hybrid antigen optionally complexed with heat shock protein, one or more polynucleotide constructs may be administered which encode the hybrid antigen, optionally with heat shock protein, in expressible form. The expressible polynucleotide constructs are introduced into cells in the subject using ex vivo or in vivo methods. Suitable methods include injection directly into tissue and tumors, transfecting using liposomes (Fraley et al., *Nature* 370:111-117 (1980)), receptor-mediated endocytosis (Zatloukal et al., *Ann. NY Acad. Sci.* 660:136-153 (1992)), particle bombardment-mediated gene transfer (Eisenbraun et al., *DNA & Cell Biol.* 12:792-797 (1993)) and transfection using peptide presenting bacteriophage (Barry et al, *Nature Medicine* 2:299-305 (1996). The polynucleotide vaccine may also be introduced into suitable cells in vitro which are then introduced into the subject.

To construct an expressible polynucleotide, a region encoding the heat shock protein and/or hybrid antigen is prepared as discussed above and inserted into a mammalian expression vector operatively linked to a suitable promoter such as the SV40 promoter, the cytomegalovirus (CMV) promoter or the Rous sarcoma virus (RSV) promoter. The resulting construct may then be used as a vaccine for genetic immunization. The nucleic acid polymer(s) could also be cloned into a viral vector. Suitable vectors include but are not limited to retroviral vectors, adenovirus vectors, vaccinia virus vectors, pox virus vectors and adenovirus-associated vectors. Specific vectors which are suitable for use in the present invention are pCDNA3 (InVitrogen), plasmid AH5 (which contains the SV40 origin and the adenovirus major late promoter), pRC/CMV (InVitrogen), pCMU II (Paabo et al., *EMBO J.* 5:1921-1927 (1986)), pZip-Neo SV (Cepko et al., *Cell* 37:1053-1062 (1984)) and pSRα (DNAX, Palo Alto, Calif.).

In the following examples, amino acids may be presented using their single-letter codes, as follows:
- A alanine
- C cysteine
- D aspartic acid
- E glutamic acid
- F phenylalanine
- G glycine
- H histidine
- I isoleucine
- K lysine
- L leucine
- M methionine
- N asparagine
- P proline
- Q glutamine
- R arginine
- S serine
- T threonine
- V valine
- W tryptophan
- Y tyrosine

EXAMPLE 1

A variety of hybrid antigens were prepared by solid-phase peptide synthesis, each comprising a heat shock protein binding domain and a cancer antigen epitope or the model epitope from ovalbumin, SIINFEKL (SEQ ID NO:357). The heat shock protein binding domains used in these experiments were among the following: HWDFAWPW (SEQ ID NO:358), NLLRLTGW (SEQ ID NO:359), FYQLALTW (SEQ ID NO:360) and RKLFFNLRW (SEQ ID NO:361).

The cancer and model epitopes were among the following:

| Source Protein | Source Tumor | Amino Acids | Trivial Name (Sequence) |
|---|---|---|---|
| Prostate Specific Membrane Antigen | Prostate cancer | 771-779 | PSMA P2 (ALFDIESKV) (SEQ ID NO:362) |
| Gp100 | Melanoma | 209-217 | IMD (T210M) (IMDQVPFSV) (SEQ ID NO:363) |
| Tyrosinase | Melanoma | 368-376 | YMD (370D) (YMDGTMSQV) (SEQ ID NO:364) |
| Human Papillomavirus (HPV) Strain 16 E7 | Cervical cancer | 86-93 | HPV16 E7 86-93 (TLGIVCPI) (SEQ ID NO:365) |
| HPV Strain 16 E7 | Cervical cancer | 11-20 | HPV 16 E7 11-20 (YMLDLQPETT) (SEQ ID NO:366) |
| Ovalbumin | Model Tumor Antigen | 257-264 | Ova (SIINFEKL) (SEQ ID NO:357) |

Using standard solid phase peptide synthesis using F-moc chemistry, hybrid antigens comprising a heat shock protein binding domain, a cancer epitope, and a gly-ser-gly linker therebetween, were synthesized, in various orientations. Thus, the following hybrid antigens were made:

| Antigenic epitope | Heat shock protein-binding domain | Hybrid antigen sequence |
|---|---|---|
| ALFDIESKV (SEQ ID NO:362) | HWDFAWPW (SEQ ID NO:358) | ALFDIESKVgsgHWDFAWPW (SEQ ID NO:369) |
| IMDQVPFSV (SEQ ID NO:363) | HWDFAWPW (SEQ ID NO:358) | IMDQVPFSVgsgHWDFAWPW (SEQ ID NO:371) |
| IMDQVPFSV (SEQ ID NO:363) | NLLRLTGW (SEQ ID NO:359) | IMDQVPFSVgsgNLLRLTGW (SEQ ID NO:372) |
| YMDGTMSQV (SEQ ID NO:364) | HWDFAWPW (SEQ ID NO:358) | YMDGTMSQVgsgHWDFAWPW (SEQ ID NO:373) |
| YMDGTMSQV (SEQ ID NO:364) | HWDFAWPW (SEQ ID NO:358) | HWDFAWPWgsgYMDGTMSQV (SEQ ID NO:374) |
| YMDGTMSQV (SEQ ID NO:364) | NLLRLTGW (SEQ ID NO:359) | YMDGTMSQVgsgNLLRLTGW (SEQ ID NO:375) |
| TLGIVCPI (SEQ ID NO:365) | HWDFAWPW (SEQ ID NO:358) | TLGIVCPIgsgHWDFAWPW (SEQ ID NO:376) |

-continued

| Antigenic epitope | Heat shock protein-binding domain | Hybrid antigen sequence |
|---|---|---|
| TLGIVCPI (SEQ ID NO:365) | NLLRLTGW (SEQ ID NO:359) | TLGIVCPIgsgNLLRLTGW (SEQ ID NO:377) |
| YMLDLQPETT (SEQ ID NO:366) | HWDFAWPW (SEQ ID NO:358) | YMLDLQPETTgsgHWDFAWPW (SEQ ID NO:378) |
| SIINFEKL (SEQ ID NO:357) | HWDFAWPW (SEQ ID NO:358) | SIINFEKLgsgHWDFAWPW (SEQ ID NO:368) |
| SIINFEKL (SEQ ID NO:357) | HWDFAWPW (SEQ ID NO:358) | HWDFAWPWgsgSIINFEKL (SEQ ID NO:379) |
| SIINFEKL (SEQ ID NO:357) | NLLRLTGW (SEQ ID NO:359) | SIINFEKLgsgNLLRLTGW (SEQ ID NO:380) |
| SIINFEKL (SEQ ID NO:357) | FYQLALTW (SEQ ID NO:360) | SIINFEKLgsgFYQLALTW (SEQ ID NO:381) |
| SIINFEKL (SEQ ID NO:357) | RKLFFNLRW (SEQ ID NO:361) | SIINFEKLgsgRKLFFNLRW (SEQ ID NO:382) |

EXAMPLE 2

Binding affinities between recombinant human or murine heat shock protein 70 (hsp70) and the various heat shock protein binding domains and antigenic peptides mentioned above, as well as between the hybrid antigens comprising an antigenic peptide and a heat shock protein binding domain described above, were determined by a binding inhibition assays (Hill plots) relative to the binding affinity of a reference, labeled hybrid antigen (tritiated ALFDIESKVGSGH-WDFAWPW) (SEQ ID NO:369) to hsp70 as determined by Scatchard analysis. Binding studies were performed in 39% PBS; 20 mM THAM, pH 8; 37 mM NaCl, 5 mM MgCl$_2$; and 1 mM ADP.

The affinities of hybrid antigens comprising the foregoing tumor antigenic peptides at the N-terminus (unless otherwise indicated), the indicated heat shock protein binding domain at the C-terminus, separated by a GSG linker, are set forth in the following table, values are expressed as Kd.

EXAMPLE 3

Non-covalent complexes of recombinant human heat shock protein 70 and hybrid antigens of the invention were evaluated for biological activity in vivo. To evaluate the induction of an antigen-specific immune response, mice were immunized on day 0 with one of the following: (1) 100 μg human hsp70; (2) a noncovalent complex of 100 μg hsp70 and 15 μg SIINFEKL (SEQ ID NO:357) (OVA peptide); (3) a noncovalent complex of 100 μg hsp70 and 15 μg SIINFEK-LGSGHWDFAWPW (SEQ ID NO:368) (N-terminal OVA peptide, C-terminal heat shock protein binding domain HWDFAWPW (SEQ ID NO:358), GSG linker in between); and (4) a noncovalent complex of 15 μg hsp70 and 15 μg SIINFEKLGSGNLLRLTGW (SEQ ID NO:367) (N-terminal OVA peptide, C-terminal heat shock protein binding domain NLLRLTGW (SEQ ID NO:359), GSG linker in between).

On day 7, splenocytes were obtained from the immunized animals and were restimulated with peptide (SIINFEKL)

| | | Heat shock protein-binding domain: | | | |
|---|---|---|---|---|---|
| Peptide (epitope) | None | HWDFAWPW (SEQ ID NO: 358) | NLLRLTGW (SEQ ID NO: 359) | FYQLALTW (SEQ ID NO: 360) | RKLFFNLRW (SEQ ID NO: 361) |
| None | | 120 μM | 1.85 μM | 5.9 μM | 15 μM |
| OVA | 279 μM | 40 μM | 1.2 μM | 1.43 μM | 7.0 μM |
| OVA (C-terminus) | 279 μM | 4.3 μM | | | |
| PSMA P1 | | 53 Mm | | | |
| PSMA P2 | 145 μM | 22 μM | 1.3 μM | | |
| Gp100 ("IMD") | 2565 μM | 155 μM | 3.1 μM | | |
| Tyrosinase ("YMD") | 204 μM | 24 μM | 2.65 μM | | |
| Tyrosinase ("YMD") (C-terminus) | 204 μM | 29 μM | | | |
| HPV16 E7 (86-93) | 187 μM | 9.1 μM | 5.2 μM | | |
| HPV16 E7 (11-20) | 91 μM | 27 μM | | | |

(SEQ ID NO:357) in vitro for 5 days, after which the percent of γ-interferon-secreting CD8+ cells was determined. The results are shown in FIG. 1.

Hsp70 alone showed a low level of response, which was not increased by the addition of OVA peptide alone (complex of hsp70 and SIINFEKL (SEQ ID NO:357)). However, the complex of hsp70 and the hybrid antigen SIINFEKLGSGHWD-FAWPW (SEQ ID NO:368) elicited an increased response. The complex comprising hsp70 and a hybrid antigen comprising OVA peptide and a higher affinity heat shock protein binding domain, NLLRLTGW (SEQ ID NO:359), gave about the same level of immune response, but this was achieved using a 6.7-fold lower amount of hsp70 (15 μg).

EXAMPLE 4

Non-covalent complexes of recombinant human heat shock protein 70 and hybrid antigens of the invention were evaluated for biological activity in in-vitro models. An in-vitro model system was established in which murine peritoneal exudes cells were exposed to a test compound of OVA peptide in the presence of B3Z cells, i.e., T-cell hybridomas that secrete IL-2 when presented with OVA peptide in the context of MHC Class I. Murine peritoneal macrophages were induced by an intraperitoneal injection of thioglycollate. Five days later, mice were sacrificed and peritoneal exudates cells were recovered by peritoneal lavage. Non-adherent cells were removed and then B3Z cells and test compounds were added. The following were tested: 1—Hybrid Antigen "A" (10 pmol) (SIINFEKL-GSG-HWD-FAWPW) (SEQ ID NO:368); 2—Noncovalent complex of Hsp70 (75 pmol) and Hybrid Antigen A (10 pmol); 3—Hybrid Antigen "B" (10 pmol) (SIINFEKL-GSG-NLLRLTGW) (SEQ ID NO:367); and 4—Noncovalent complex of Hsp70 (75 pmol) and Hybrid Antigen B (10 pmol).

Figure 2:
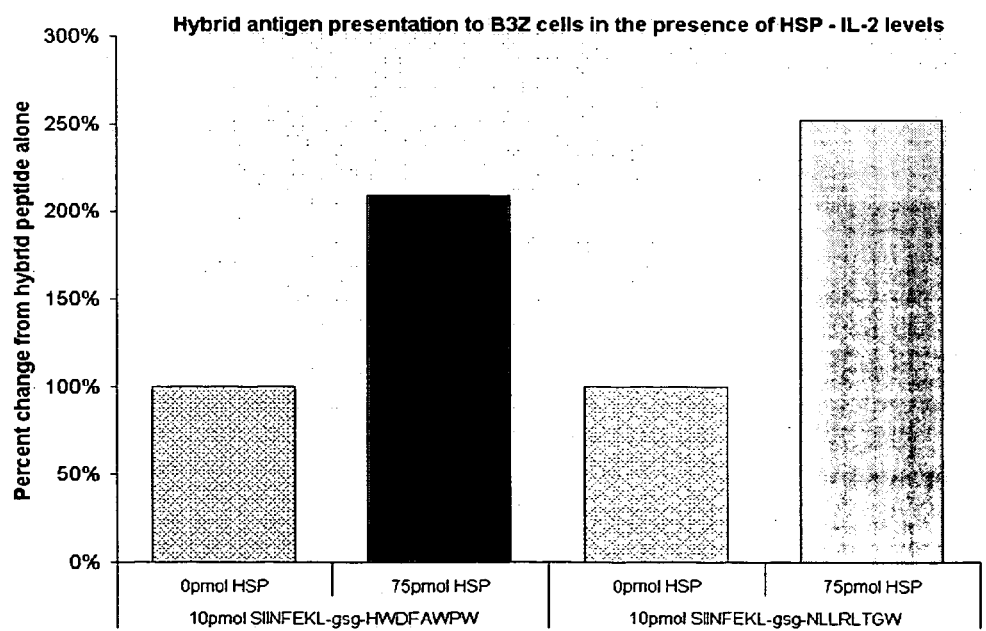
FIG. 2 shows the induction of an in-vitro immune response using various hybrid antigens of the invention in a complex with hsp70. In particular, hybrid antigens SIINFEKLGSGHWDFAWPW (SEQ ID NO:368) and SIINFEKLGSGNLLRLTGW (SEQ ID NO:367) were assayed.

Cell-free supernatants were harvested after 18 h and tested in capture ELISAs for levels of IL-2. Both hybrid antigens in complexes with hsp70 presented antigen to the OVA-specific T-cell hybridomas, the results of which are set forth in FIG. 2.

EXAMPLE 5

A Phase I/IIa clinical study in stage III and IV melanoma patients was conducted. Twenty-seven stage III/IV melanoma patients were divided into three groups and administered five doses of one of three formulations (low, medium and high dose) during a nineteen-week period. Nine patients received low doses, nine patients received medium doses, and nine patients received high doses. The components of the formulations include two hybrid antigens mentioned above, each having a tumor antigenic domain (epitope) and an hsp70 binding domain, complexed with recombinant human hsp70, as follows:

Hybrid Antigen "I"

YMDGTMSQV-GSG-HWDFAWPW (SEQ ID NO:373) (Amino acids 368-378 of the melanoma tumor-associated antigen tyrosinase (YMDGTMSQV) (SEQ ID NO:364), GSG linker, Hsp70 binding domain HWDFAWPW) (SEQ ID NO:358)

Hybrid Antigen "II"

IMDQVPFSV-GSG-HWDFAWPW (SEQ ID NO:371) (Amino acids 209-217 of the melanoma tumor-associated antigen gp100 (IMDQVPFSV) (SEQ ID NO:363), GSG linker, Hsp70 binding domain HWDFAWPW) (SEQ ID NO:358)

In the low, medium, and high dose groups, either 1, 10 or 100 micrograms, respectively, of both of the foregoing hybrid antigens were formulated with 200 micrograms of recombinant human hsp70, and administered to patients at weeks 0, 1, 2, 6, and 18. Bloods were drawn for immunological assays pre-immunization and at 8, 19 and 30 weeks. Fifteen patients' samples were evaluable for T-cell immunity, five patients in each dose group. A positive response was defined as a two-fold or greater increase in peptide-specific CD8+ T cells, measured by tetramer staining.

Overall, in 74% (20 of 27) of the patients, disease had not progressed at a median follow-up of 20 months. Of those 15 patients with evaluable blood samples, sixty percent (9 of 15) showed an increase in peptide-specific CD8+ T cells, and more positive T-cell responders were observed in the high-dose group. Only one (⅑) of these patients showed progression of disease. In contrast, disease progressed in three of the 6 patients who did not show a positive T-cell response.

EXAMPLE 6

Figure 3:
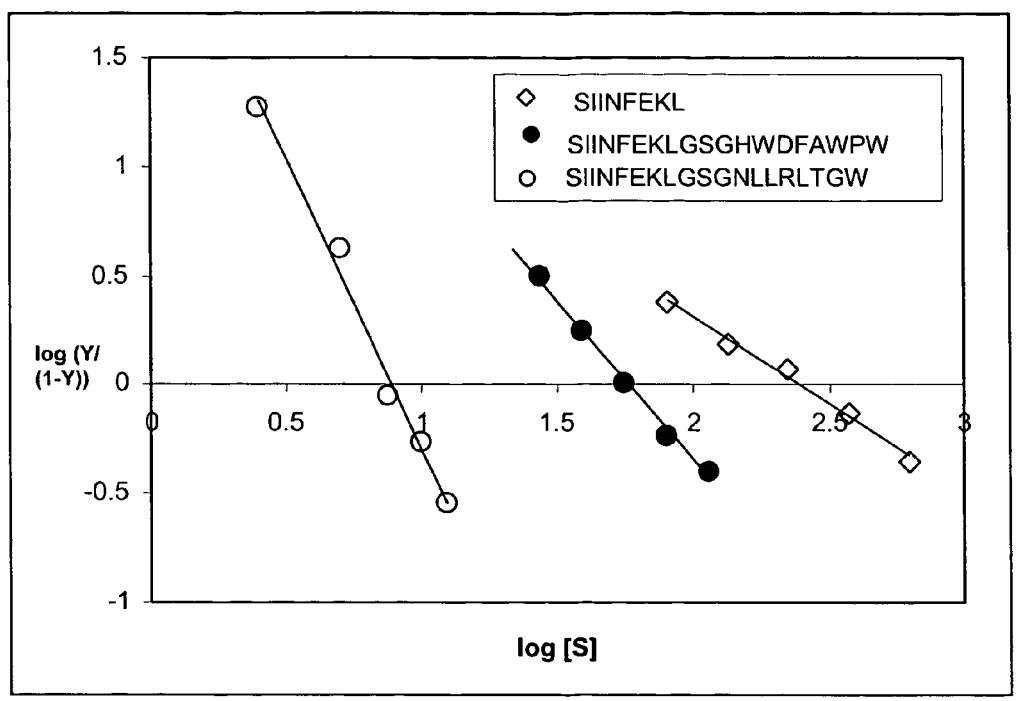
FIG. 3 shows Hill plots for determining the affinity of various peptides for hsp70. In particular, the epitope SIINFEKL (SEQ ID NO: 357) and the hybrid antigens SIINFEKLGSGHWDFAWPW (SEQ ID NO:368) and SIINFEKLGSGNLLRLTGW (SEQ ID NO:367) were assayed.

FIG. 3 shows various concentrations of SIINFEKL (SEQ ID NO:357) (Ova), SIINFEKLGSGHWDFAWPW (SEQ ID NO:368)or SIIFEKLGSGNLLRLTGW (SEQ ID NO:367) hybrid antigens titrated into binding reactions containing constant amounts of both HSP70 and a labeled reporter peptide of known affinity for HSP70. The abilities of these peptides to compete out the binding of the reporter were analyzed using a Hill plot and the IC50 of each determined as the point where the plot intersected the y-axis. The Kd of each peptide was then calculated from its experimentally determined IC50. There was a 15-fold increase in affinity of SIINFEKLGSGN-LLRLTGW (SEQ ID NO:367) over SIINFEKLGSGHWD-FAWPW (SEQ ID NO:368).

EXAMPLE 7

Figure 4A:
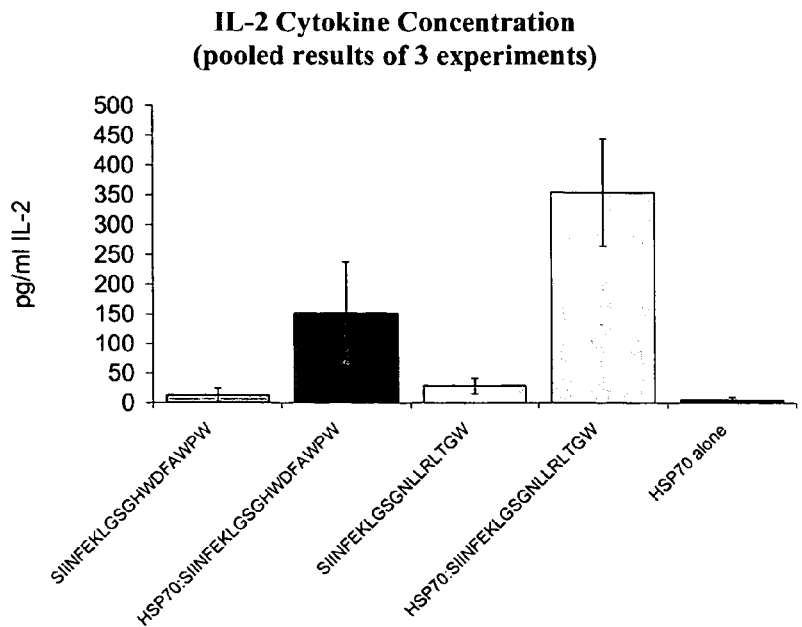
FIGS. 4a and 4b show the results of an in-vitro macrophage T-cell activation assay using various hybrid antigens of the invention alone or in a complex with hsp70. In particular, the hybrid antigens SIINFEKLGSGHWDFAWPW (SEQ ID NO:368) and SIINFEKLGSGNLLRLTGW (SEQ ID NO:367) were assayed.
Figure 4B:
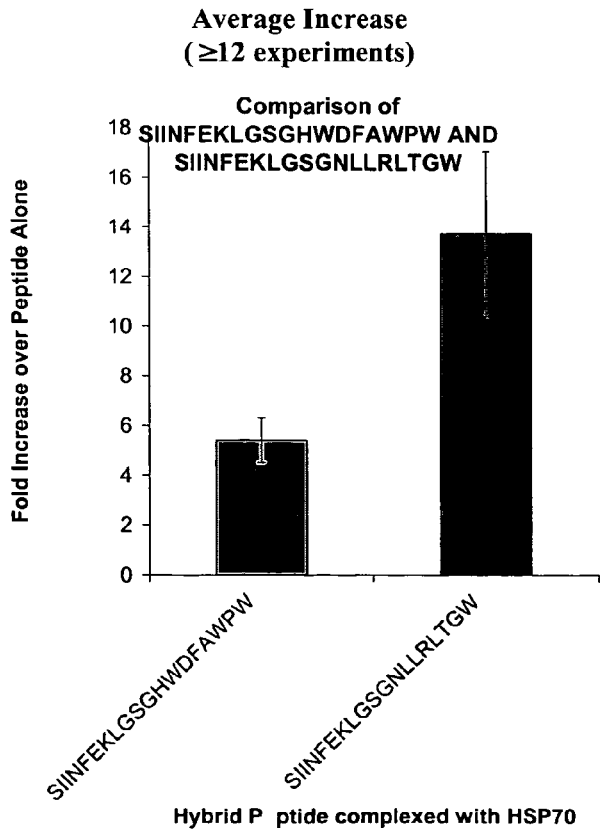

Peptides, alone or in a complex with HSP70, were added to adherent peritoneal exudate cells from thioglycollate induced mice. These cells were then cocultured with the B3Z T cell hybridoma, which produces IL-2 upon recognition of SIIN-FEKL (SEQ ID NO:357) in the context of H-2K$^b$. After an 18 h incubation in serum free medium, supernatants were harvested and tested by ELISA. Data are shown in FIG. 4a and 4b as the mean+/− S.D. FIG. 4a shows supernatant IL-2 quantities; FIG. 4b shows fold-induction of IL-2 over hybrid antigen alone.

EXAMPLE 8

Figure 5:
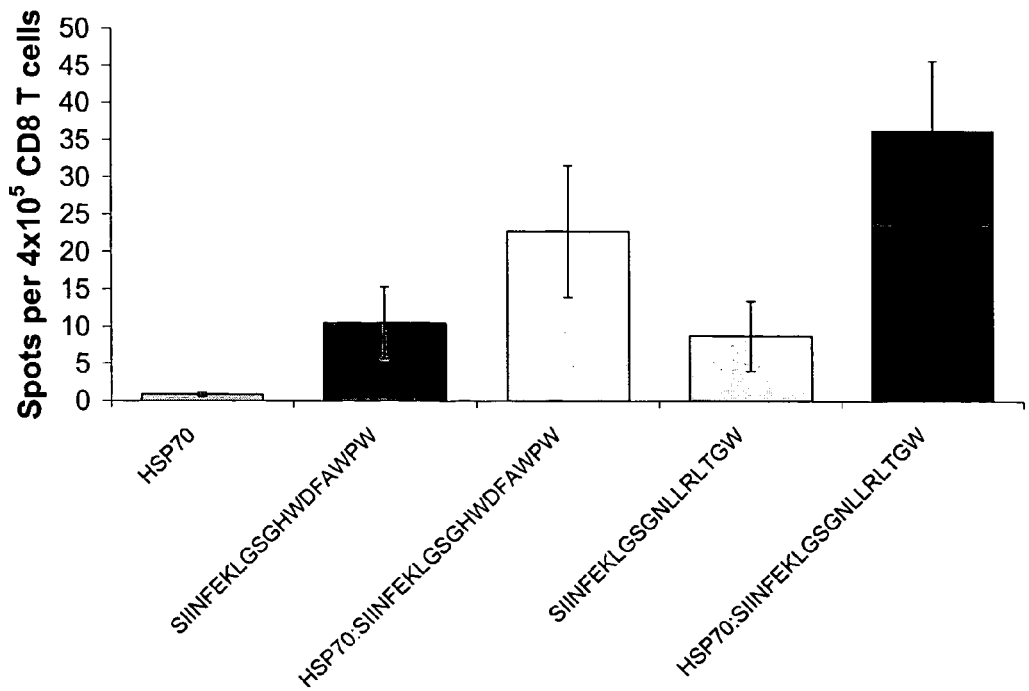
FIG. 5 shows in-vivo responses to complexes of hybrid antigens of the invention alone or in a complex with hsp70. In particular, the hybrid antigens SIINFEKLGSGHWD-FAWPW (SEQ ID NO:368) and SIINFEKLGSGNLLR-LTGW (SEQ ID NO:367) were assayed.

C57BL/6 mice were immunized s.c. at the base of the tail with 2 mg hybrid antigen complexed with HSP or the appropriate controls. 7 d later, mice were euthanized, CD8+ T cells were enriched from the spleens and put into an ex vivo ELISPOT to measure IFN-γ production. Data are shown in FIG. 5 as the mean+/− SE for ≧four experiments containing at least 3 mice per observation per experiment.

EXAMPLE 9

Figure 6:
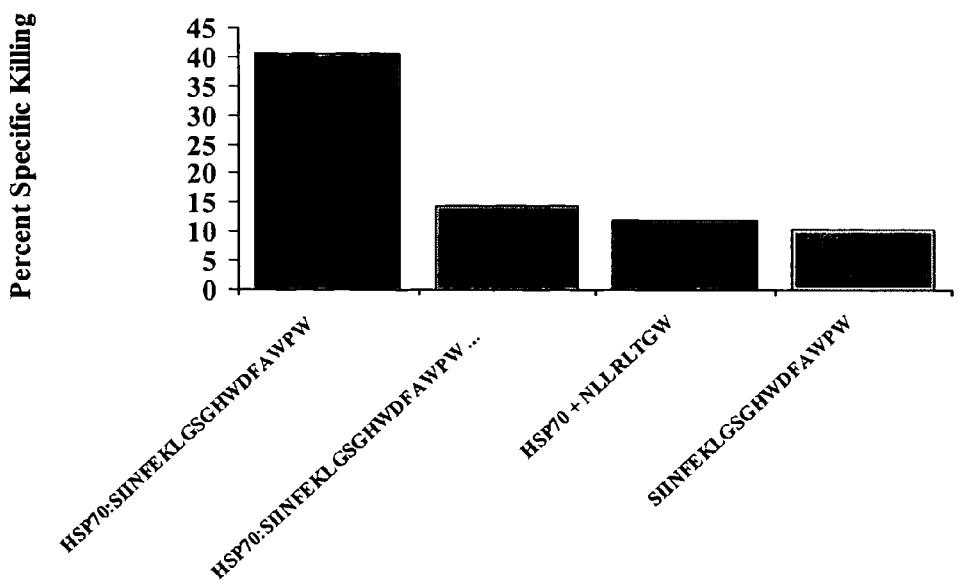
FIG. 6 shows the blocking of in-vivo responses to one hybrid antigen-hsp70 complex (the hybrid antigen SIINFEK-LGSGHWDFAWPW (SEQ ID NO:368) complexed to hsp70) with the addition of a heat shock protein binding domain peptide (NLLRLTGW (SEQ ID NO:359)) alone.

Mice were immunized s.c. at the base of the tail with the complexes listed above—NLLRLTGW (SEQ ID NO:359) alone was added at a five-fold molar excess of the SIINFEK-LGSGHWDFAWPW (SEQ ID NO:358) dose. 7 d later, spleens were harvested and stimulated in vitro with SIIN-FEKL (SEQ ID NO:357) peptide. After 5 d, peptide-specific effector responses were measured in a $^{51}$Cr release assay, results shown in FIG. 6. Values within bars represent the amount of epitope delivered. 100:1 E:T ratio shown.

EXAMPLE 10

Figure 7:
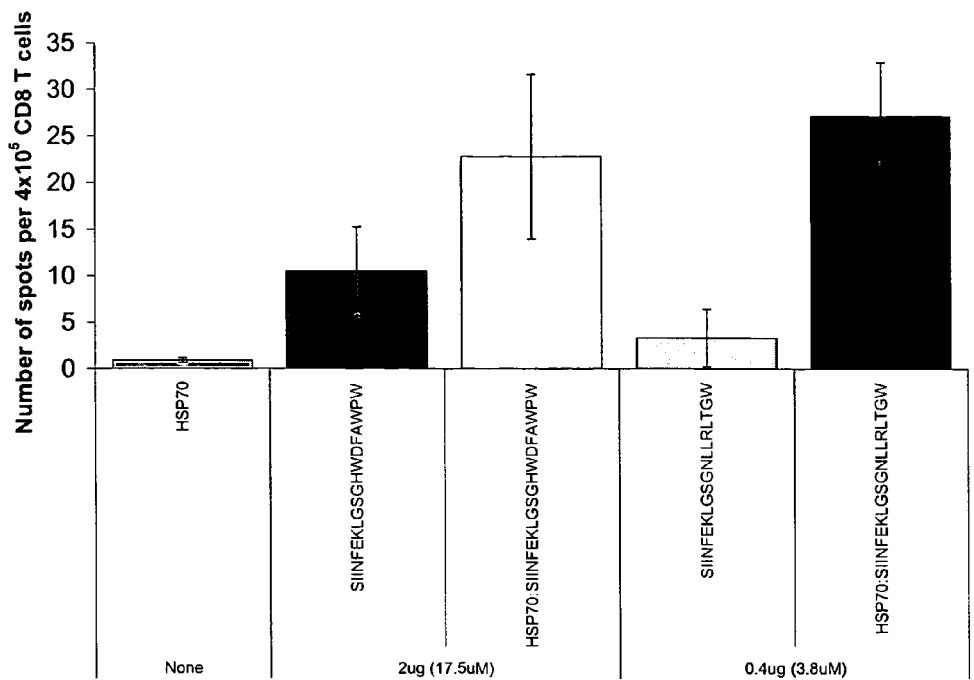
FIG. 7 shows that smaller doses of a higher affinity heat shock protein binding domain-epitope in a complex with hsp70 can elicit immune responses in vivo. In particular, the hybrid antigens SIINFEKLGSGHWDFAWPW (SEQ ID NO:368) and SIINFEKLGSGNLLRLTGW (SEQ ID NO:367) were assayed.

Mice were immunized s.c. at the base of the tail with the indicated doses of hybrid antigen with or without HSP70 or HSP70 alone. 7 d later, spleens were harvested and enriched for CD8+ T cells, which were put into an ex vivo IFN-γ ELISPOT assay. Data are shown in FIG. 7 as mean+/- standard error of ≧four experiments with at least three mice per group.

The foregoing Examples show that a higher-affinity HSP70 binding sequence (in these non-limiting examples, NLLRLTGW) (SEQ ID NO:359) can decrease the dissociation constant of a hybrid antigen containing this sequence and a known class I MHC antigenic epitope SIINFEKL (SEQ ID NO:357). The higher affinity of the heat shock protein-binding domain-epitope hybrid antigen does not adversely affect the ability of the immunogenic epitope to be processed and presented by MHC class I molecules. There is a positive correlation between the HSP70 binding affinity of the heat shock protein-binding domain-epitope hybrid antigen and CD8+ T cell immune responses elicited. Thus, smaller amounts of defined epitopes can be used with a higher-affinity heat shock protein-binding domain such as but not limited to NLLRLTGW (SEQ ID NO:359) to successfully immunize in vivo.

EXAMPLE 11

Additional hybrid antigens comprising a human melanoma cancer epitope at the N-terminus, a Gly-Ser-Gly linker and the heat shock protein-binding domain Asn Leu Leu Arg Leu Thr Gly Trp were prepared by solid-phase peptide synthesis, and their affinities for hsp70 determined as above, compared with the melanoma epitope alone. The following table sets forth the various melanoma epitopes (names of proteins abbreviated, followed by the amino acids in the epitope, followed by any change to the native sequence in parentheses) and their affinities for hsp70 expressed in μM, either alone or in a hybrid antigen as mentioned above.

| | Epitope alone | | Hybrid antigen comprising epitope | |
|---|---|---|---|---|
| Cancer Epitope: amino acids | Epitope sequence | Affinity for hsp70 (μM) | Hybrid antigen sequence | Affinity for hsp70 (μM) |
| Gp100: 209-217 (210M) | IMDQVPFSV (SEQ ID NO:363) | 2566 | IMDQVPFSVGSGNLLRLTGW (SEQ ID NO:372) | 0.9 |
| Tyrosinase: 368-376 (370D) | YMDGTMSQV (SEQ ID NO:364) | 209 | YMDGTMSQVGSGNLLRLTGW (SEQ ID NO:375) | 1.8 |
| MelA/MART1: 26-35 (27L) | ELAGIGILTV (SEQ ID NO:389) | 45 | ELAGIGILTVGSGNLLRLTGW (SEQ ID NO:395) | 0.6 |
| NY-ESO-1: 157-165 (165V) | SLLMWITQV (SEQ ID NO:390) | 114 | SLLMWITQVGSGNLLRLTGW (SEQ ID NO:396) | 2.2 |
| Trp-2: 180-188 | SVYDFFVWL (SEQ ID NO:391) | 81 | SVYDFFVWLGSGNLLRLTGW (SEQ ID NO:397) | 2.9 |
| MAGE-10: 254-262 | GLYDGMEHL (SEQ ID NO:392) | 48 | GLYDGMEHLGSGNLLRLTGW (SEQ ID NO:398) | 1.1 |
| GP100: 280-288 (288V) | YLEPGPVTV (SEQ ID NO:393) | 71 | YLEPGPVTVGSGNLLRLTGW (SEQ ID NO:399) | 2.0 |
| SSX-2: 41-49 | KASEKIFYV (SEQ ID NO:394) | 57 | KASEKIFYVGSGNLLRLTGW (SEQ ID NO:400) | 1.4 |

EXAMPLE 12

In a similar fashion to melanoma antigens in the previous example, hybrid antigens were synthesized using various HLA A2 HIV epitopes. Affinities for hsp70 of the epitopes alone and in a hybrid antigen are shown in the following table.

| | Epitope alone | | Hybrid antigen comprising epitope | |
|---|---|---|---|---|
| HIV Epitope: amino acids | Epitope sequence | Affinity for hsp70 (μM) | Hybrid antigen sequence | Affinity for hsp70 (μM) |
| Nef: 190-198 | ALKHRAYEL (SEQ ID NO:401) | 97 | ALKHRAYELGSGNLLRLTGW (SEQ ID NO:409) | 1.1 |

-continued

| HIV Epitope: amino acids | Epitope alone | | Hybrid antigen comprising epitope | |
|---|---|---|---|---|
| | Epitope sequence | Affinity for hsp70 (µM) | Hybrid antigen sequence | Affinity for hsp70 (µM) |
| Pol: 464-472 | ILKEPVHGV (SEQ ID NO:402) | 83 | ILKEPVHGVGSGNLLRLTGW (SEQ ID NO:410) | 1.2 |
| Gag/p17: 77-85 (79F) | SLFNTVATL (SEQ ID NO:403) | 35 | SLFNTVATLGSGNLLRLTGW (SEQ ID NO:411) | 1.9 |
| Pol: 263-273 | VLDVGDAYF SV (SEQ ID NO:404) | 110 | VLDVGDAYFSVGSGNLLRLTGW (SEQ ID NO:412) | 2.0 |
| Pol: 334-342 | VIYQYMDDL (SEQ ID NO:405) | 91 | VIYQYMDDLGSGNLLRLTGW (SEQ ID NO:413) | 1.7 |
| Gag: 77-85 | SLYNTVATL (SEQ ID NO:406) | 85 | SLYNTVATLGSGNLLRLTGW (SEQ ID NO:414) | 1.8 |
| Vpr: 59-67 | AIIRILQQL (SEQ ID NO:407) | 93 | AIIRILQQLGSGNLLRLTGW (SEQ ID NO:415) | 0.6 |
| Nef: 190-198 | AFHHVAREL (SEQ ID NO:408) | 84 | AFHHVARELGSGNLLRLTGW (SEQ ID NO:416) | 2.1 |

EXAMPLE 13

For immunological studies in mice, a murine MHC H2-K (b) epitope from ovalbumin, SIINFEKL (SEQ ID NO:357) (amino acids 257-264), and a H2-K(b) peptide from the nucleoprotein of vesicular stomatitis virus (VSV), RGYVYQGL (SEQ ID NO:370) (amino acids 52-59) were used for the preparation of hybrid antigens. The following table sets forth the sequences and the affinities for hsp70 of the epitopes alone and in hybrid antigens.

| Mouse Epitope | Epitope alone | | Hybrid antigen comprising epitope | |
|---|---|---|---|---|
| | Epitope sequence | Affinity for hsp70 (µM) | Hybrid antigen sequence | Affinity for hsp70 (µM) |
| Ovalbumin: amino acids 257-264 | SIINFEKL (SEQ ID NO:357) | 235 | NLLRLTGWGSGSHNFEKL (SEQ ID NO:383) | 1.6 |
| VSV nucleo-protein: amino acids 52-59 | RGYVYQGL (SEQ ID NO:370) | 82 | NLLRLTGWGSGRGYVYQGL (SEQ ID NO:386) | 1.4 |

EXAMPLE 14

Mice were immunized s.c. at the base of the tail with hsp70 alone, hsp70 complexed with SIINFEKL (SEQ ID NO:357), and hybrid SIINFEKL (SEQ ID NO:357) peptide with or without HSP70. The doses were adjusted such that each immunization contained the same amount of SIINFEKL (SEQ ID NO:357), except for hsp70 alone. Seven days later, spleens were harvested and enriched for CD8+ T cells, which were put into an ex vivo IFN-γ ELISPOT assay. Responses after pulsing with SIINFEKL (SEQ ID NO:357) ("SIINFEKL") were recorded in the following table, which includes the doses, and the number of spots (mean±standard error) per $4 \times 10^5$ CD8 T cells, of ≧four experiments with at least three mice per group. Controls included medium alone ("medium control"), unpulsed T cells ("unpulsed control"), T cells pulsed with a non-immunized peptide derived from VSV, RGYVYQGL (SEQ ID NO:370) ("VSV control"), and exposure to concanavalin A as a positive control ("Con A positive control").

In the same experiment, a $^{51}$Cr-release assay as described above was done using SIINFEKL-pulsed target cells. At an effector to target cell ratio of 200:1, the percent killing results obtained are shown in the far right column of the following table.

(200-10)

|  | Number of Spots per 400,000 cells | | | | | CTL assay: |
|---|---|---|---|---|---|---|
| Immunogen | SIINFEKL | Medium control | Unpulsed control | VSV control | Con A positive control | % killing at 200:1 E/T |
| 4.4 µg Hsp70 | 0.00 ± 0.00 | 1.50 ± 2.12 | 0.67 ± 0.58 | 0.33 ± 0.58 | 834 ± 28.3 | 0% |
| 4.4 µg Hsp70 + 0.9 µg SIINFEKL (SEQ ED NO:357) | 33.7 ± 7.09 | 0.00 ± 0.00 | 0.33 ± 0.58 | 0.00 ± 0.00 | 1000 ± 33.7 | 19% |
| 4.4 µg Hsp70 + 2.0 µg NLLRLTGWGSGSIINFEKL (SEQ ID NO:383) | 80.0 ± 17.0 | 0.00 ± 0.00 | 1.50 ± 0.71 | 1.50 ± 0.71 | 1170 ± 56.5 | 38% |

EXAMPLE 15

An experiment similar to that described above was carried out, which also included hybrid antigen without hsp70.

(200-11)

|  | Number of Spots per $4 \times 10^5$ CD8 T cells | | | | |
|---|---|---|---|---|---|
| Immunogen | SIINFEKL | Medium control | Unpulsed control | VSV control | Con A Positive control |
| 4.4 µg Hsp70 | 0.33 ± 0.58 | 1.00 ± 1.73 | 1.67 ± 1.15 | 4.00 ± 1.00 | 965 ± 62.6 |
| 4.4 µg Hsp70 + 0.9 µg SIINFEKL (SEQ ID NO:357) | 1.67 ± 0.58 | 1.00 ± 1.00 | 2.00 ± 0.00 | 2.67 ± 2.08 | 591 ± 48.1 |
| 4.4 µg Hsp70 + 2.0 µg NLLRLTGWGSGSIINFEKL (SEQ ID NO:383) | 12.0 ± 5.2 | 2.67 ± 0.58 | 1.67 ± 1.15 | 2.00 ± 2.65 | 748 ± 58.6 |

EXAMPLE 16

A further experiment was carried out similar to that described above.

(200-12)

|  | Number of spots per 300,000 CD8 T cells | | | | | CTL assay: |
|---|---|---|---|---|---|---|
| Immunogen | SIINFEKL | Medium control | Unpulsed control | VSV control | Con A positive control | % killing at 200:1 E/T |
| 4.4 µg Hsp70 | 0.67 ± 0.58 | 0.00 ± 0.00 | 0.50 ± 0.71 | 1.00 ± 1.41 | 552 ± 24.0 | 8.45 ± 41.3 |
| 4.4 µg Hsp70 + 0.9 µg SIINFEKL (SEQ ID NO:357) | 3.33 ± 2.52 | 0.00 ± 0.00 | 0.33 ± 0.58 | 0.33 ± 0.58 | 450 ± 69.0 | 43.0 ± 21.2 |
| 4.4 µg Hsp70 + 2.00 µg NLLRLTGWGSG-SIINFEKL (SEQ ID NO:383) | 134 ± 4.16 | 1.33 ± 1.53 | 0.67 ± 1.15 | 1.00 ± 1.00 | 865 ± 93.0 | 31.9 ± 5.41 |

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the contents of which are hereby incorporated by reference in their entireties.

What is claimed is:

1. A hybrid antigen comprising at least one antigenic domain of an infectious agent or tumor antigen and a binding domain that non-covalently binds to a heat shock protein, wherein the binding domain comprises Asn Leu Leu Arg Leu Thr Gly Trp (SEQ ID NO:417), Phe Tyr Gln Leu Ala Leu Thr Trp (SEQ ID NO:186), or Arg Lys Leu Phe Phe Asn Leu Arg Trp (SEQ ID NO:419).

2. The hybrid antigen of claim 1 wherein a peptide linker separates the antigenic domain and the binding domain.

3. A composition comprising at least one hybrid antigen of claim 1 and a pharmaceutically acceptable carrier.

4. A method for inducing an immune response in a subject to an infectious agent comprising administering to the subject at least one hybrid antigen of claim 1, wherein said at least one hybrid antigen comprises at least one antigenic domain of said infectious agent.

5. A method for inducing an immune response in a subject to an infectious agent comprising administering to the subject a complex of:
   (a) at least one hybrid antigen of claim 1, wherein said at least one hybrid antigen comprises at least one antigenic domain of said infectious agent; and
   (b) at least one said heat shock protein;
wherein the hybrid antigen and the at least one said heat shock protein are non-covalently bound.

6. The method of claim 5 wherein the at least one said heat shock protein is a hsp70 family member.

7. A method for treating an infectious disease comprising administering to a subject having an infectious disease at least one hybrid antigen of claim 1, which said at least one hybrid antigen comprises at least one antigenic domain of an infectious agent, and wherein said infectious agent causes said infectious disease.

8. A method for treating an infectious disease comprising administering to a subject having an infectious disease a complex of:
   (a) at least one hybrid antigen of claim 1, wherein said at least one hybrid antigen comprises at least one antigenic domain of an infectious agent, and wherein said infectious agent causes said infectious disease; and
   (b) at least one said heat shock protein;
wherein the hybrid antigen and the at least one said heat shock protein are non-covalently bound.

9. The method of claim 8 wherein the at least one said heat shock protein is a hsp70 family member.

10. A hybrid antigen consisting essentially of at least one antigenic domain of an infectious agent or tumor antigen, a binding domain that non-covalently binds to a heat shock protein, and a peptide linker separating the antigenic domain and the binding domain, and wherein the binding domain comprises Asn Leu Leu Arg Leu Thr Gly Trp (SEQ ID NO:417), Phe Tyr Gln Leu Ala Leu Thr Trp (SEQ ID NO:186), or Arg Lys Leu Phe Phe Asn Leu Arg Trp (SEQ ID NO:419).

11. A composition comprising at least one hybrid antigen of claim 10 and a pharmaceutically acceptable carrier.

12. A method for inducing an immune response in a subject to an infectious agent comprising administering to the subject at least one hybrid antigen of claim 10, wherein said at least one hybrid antigen comprises at least one antigenic domain of said infectious agent.

13. A method for inducing an immune response in a subject to an infectious agent comprising administering to the subject a complex of:
   (a) at least one hybrid antigen of claim 10, wherein said at least one hybrid antigen comprises at least one antigenic domain of said infectious agent; and
   (b) at least one said heat shock protein;
wherein the hybrid antigen and the at least one said heat shock protein are non-covalently bound.

14. The method of claim 13 wherein the at least one said heat shock protein is a hsp70 family member.

15. A method for treating an infectious disease comprising administering to a subject having an infectious disease at least one hybrid antigen of claim 10, wherein said at least one hybrid antigen comprises at least one antigenic domain of an infectious agent, and wherein said infectious agent causes said infectious disease.

16. A method for treating an infectious disease comprising administering to a subject having an infectious disease a complex of:
   (a) at least one hybrid antigen of claim 10, wherein said at least one hybrid antigen comprises at least one antigenic domain of an infectious agent, and wherein said infectious agent causes said infectious disease; and
   (b) at least one said heat shock protein;
wherein the hybrid antigen and the at least one said heat shock protein are non-covalently bound.

17. The method of claim 16 wherein the at least one said heat shock protein is a hsp70 family member.

18. A method for inducing an immune response in a subject to a tumor antigen comprising administering to the subject at least one hybrid antigen of claim 1 or 10, wherein said at least one hybrid antigen comprises at least one antigenic domain of said tumor antigen.

19. A method for inducing an immune response in a subject to a tumor antigen comprising administering to a subject a complex of:
   (a) at least one hybrid antigen of claim 1 or 10, wherein said at least hybrid antigen comprises at least one antigenic domain of said tumor antigen; and
   (b) at least one said heat shock protein;
wherein the hybrid antigen and the at least one said heat shock protein are non-covalently bound.

20. The method of claim 19 wherein the at least one said heat shock protein is a hsp70 family member.

21. A method for treating cancer comprising administering to a subject having a cancer at least one hybrid antigen of claim 1 or 10, which said at least one hybrid antigen comprises at least one antigenic domain of a tumor antigen, and wherein said tumor antigen is associated with said cancer.

22. A method for treating cancer comprising administering to a subject having a cancer a complex of:

(a) at least one hybrid antigen of claim 1 or 10, which said at least one hybrid antigen comprises at least one antigenic domain of a tumor antigen, and wherein said tumor antigen is associated with said cancer; and (b) at least one said heat shock protein;

wherein the hybrid antigen and the at least one said heat shock protein are non-covalently bound.

23. The method of claim 22 wherein the at least one said heat shock protein is a hsp70 family member.

24. The hybrid antigen of claim 1 or 10, wherein said hybrid antigen is in the range of 10-500 amino acids.

25. The hybrid antigen of claim 1 or 10, wherein said antigenic domain is of an infectious agent.

26. The hybrid antigen of claim 1 or 10, wherein said antigenic domain is of a tumor antigen associated with a cancer.

27. The hybrid antigen of claim 26, wherein the cancer is selected from the group consisting of sarcoma, lymphoma, leukemia, melanoma, carcinoma of the breast, carcinoma of the prostate, ovarian carcinoma, carcinoma of the cervix, uterine carcinoma, colon carcinoma, carcinoma of the lung, glioblastoma, and astrocytoma.

28. The hybrid antigen of claim 25, wherein the infectious agent is selected from the group consisting of a bacterium, a virus, a protozoan, a mycoplasma, a fungus, a yeast, a parasite, and a prion.

29. The hybrid antigen of claim 28, wherein the infectious agent is a bacterium.

30. The hybrid antigen of claim 29, wherein the bacterium is selected from the group consisting of *Salmonella, Staphylococcus, Streptococcus, Enterococcus, Clostridium, Escherichia, Klebsiella, Vibrio, Mycobacterium*, and *Mycoplasma pneumoniae*.

31. The hybrid antigen of claim 28, wherein the infectious agent is a virus.

32. The hybrid antigen of claim 31, wherein the virus is selected from the group consisting of a human papilloma virus, herpes virus, retrovirus, hepatitis virus, influenza virus, rhinovirus, respiratory syncytial virus, cytomegalovirus, adenovirus, herpes simplex virus, herpes zoster virus, human immunodeficiency virus 1, and human immunodeficiency virus 2.

33. The hybrid antigen of claim 28, wherein the infectious agent is a protozoan.

34. The hybrid antigen of claim 33, wherein the protozoan is selected from the group consisting of an amoeba, a malarial parasite, and *Trypanosoma cruzi*.

35. A composition comprising a non-covalent complex of at least one hybrid antigen of claim 1 or 10 and at least one said heat shock protein; and a pharmaceutically acceptable carrier.

36. The composition of claim 35, wherein the at least one said heat shock protein is a hsp70 family member.

37. The composition of claim 36, wherein the hsp70 family member is BiP, hsp70 or hsc70.

38. The composition of claim 3 or 11 further comprising one or more adjuvants.

39. The composition of claim 35 further comprising one or more adjuvants.

40. A composition comprising more than one hybrid antigen of claim 1 or 10.

41. The composition of claim 40 further comprising a plurality of heat shock proteins non-covalently complexed to the more than one hybrid antigen.

42. The method of claim 4, 5, 12 or 13 wherein the subject is a human.

43. The method of claim 18 wherein the subject is a human.

44. The method of claim 19 wherein the subject is a human.

45. The composition of claim 35, wherein the at least one said heat shock protein is gp96 or hsp90.

* * * * *

SEQUENCE LISTING

```
<160> NUMBER OF SEQ ID NOS: 419

<210> SEQ ID NO 1
<211> LENGTH: 4
<212> TYPE: PRT
<213> ORGANISM: Malaria

<400> SEQUENCE: 1

Asn Ala Asn Pro
 1

<210> SEQ ID NO 2
<211> LENGTH: 9
<212> TYPE: PRT
<213> ORGANISM: Unknown
<220> FEATURE:
<223> OTHER INFORMATION: HLA-A2 peptide binding motif
<220> FEATURE:
<221> NAME/KEY: VARIANT
<222> LOCATION: 2
<223> OTHER INFORMATION: Xaa = Leu or Met
<220> FEATURE:
<221> NAME/KEY: VARIANT
<222> LOCATION: 6
<223> OTHER INFORMATION: Xaa = Val or Ile or Leu or Thr
<220> FEATURE:
<221> NAME/KEY: VARIANT
<222> LOCATION: 9
<223> OTHER INFORMATION: Xaa = Val or Leu
<220> FEATURE:
<221> NAME/KEY: VARIANT
<222> LOCATION: 1,3 , 4, 5, 7, 8
<223> OTHER INFORMATION: Xaa = any amino acid

<400> SEQUENCE: 2

Xaa Xaa Xaa Xaa Xaa Xaa Xaa Xaa Xaa
 1               5

<210> SEQ ID NO 3
<211> LENGTH: 9
<212> TYPE: PRT
<213> ORGANISM: Unknown
<220> FEATURE:
<223> OTHER INFORMATION: HLA-A2 peptide binding motif
<220> FEATURE:
<221> NAME/KEY: VARIANT
<222> LOCATION: 2
<223> OTHER INFORMATION: Xaa = Leu or Met
<220> FEATURE:
<221> NAME/KEY: VARIANT
<222> LOCATION: 1, 3, 4, 5, 6, 7, 8
<223> OTHER INFORMATION: Xaa = any amino acid

<400> SEQUENCE: 3

Xaa Xaa Xaa Xaa Xaa Xaa Xaa Xaa Val
 1               5

<210> SEQ ID NO 4
<211> LENGTH: 8
<212> TYPE: PRT
<213> ORGANISM: Unknown
<220> FEATURE:
```

```
<223> OTHER INFORMATION: HLA-A2 peptide binding motif
<220> FEATURE:
<221> NAME/KEY: VARIANT
<222> LOCATION: 2
<223> OTHER INFORMATION: Xaa = Val or Gln
<220> FEATURE:
<221> NAME/KEY: VARIANT
<222> LOCATION: 1, 3, 4, 5, 6, 7,
<223> OTHER INFORMATION: Xaa = any amino acid

<400> SEQUENCE: 4

Xaa Xaa Xaa Xaa Xaa Xaa Xaa Leu
 1               5

<210> SEQ ID NO 5
<211> LENGTH: 5
<212> TYPE: PRT
<213> ORGANISM: Unknown
<220> FEATURE:
<223> OTHER INFORMATION: HLA-DR peptide binding motif

<400> SEQUENCE: 5

Gln Lys Arg Ala Ala
 1               5

<210> SEQ ID NO 6
<211> LENGTH: 5
<212> TYPE: PRT
<213> ORGANISM: Unknown
<220> FEATURE:
<223> OTHER INFORMATION: HLA-DR peptide binding motif

<400> SEQUENCE: 6

Arg Arg Arg Ala Ala
 1               5

<210> SEQ ID NO 7
<211> LENGTH: 7
<212> TYPE: PRT
<213> ORGANISM: Unknown
<220> FEATURE:
<223> OTHER INFORMATION: motif in heptamiric region  recognized by heat
     shock protein
<220> FEATURE:
<221> NAME/KEY: VARIANT
<222> LOCATION: 2
<223> OTHER INFORMATION: Xaa = Trp or any amino acid
<220> FEATURE:
<221> NAME/KEY: VARIANT
<222> LOCATION: 1, 3, 5, 7
<223> OTHER INFORMATION: Xaa = hydrophobic amino acid residues
<220> FEATURE:
<221> NAME/KEY: VARIANT
<222> LOCATION: 4, 6
<223> OTHER INFORMATION: Xaa = any amino acid

<400> SEQUENCE: 7

Xaa Xaa Xaa Xaa Xaa Xaa Xaa
 1               5

<210> SEQ ID NO 8
<211> LENGTH: 7
<212> TYPE: PRT
<213> ORGANISM: Unknown
<220> FEATURE:
<223> OTHER INFORMATION: motif in heptamiric region  recognized by heat
     shock protein
<220> FEATURE:
<221> NAME/KEY: VARIANT
<222> LOCATION: 2
<223> OTHER INFORMATION: Xaa = Trp or any amino acid
```

```
<220> FEATURE:
<221> NAME/KEY: VARIANT
<222> LOCATION: 1, 3, 5, 7,
<223> OTHER INFORMATION: Xaa = hydrophobic amino acid residue,
      particularly tryptophan, leucine or phenylalanine
<220> FEATURE:
<221> NAME/KEY: VARIANT
<222> LOCATION: 4, 6
<223> OTHER INFORMATION: Xaa = any amino acid

<400> SEQUENCE: 8

Xaa Xaa Xaa Xaa Xaa Xaa Xaa
 1               5

<210> SEQ ID NO 9
<211> LENGTH: 4
<212> TYPE: PRT
<213> ORGANISM: Artificial Sequence
<220> FEATURE:
<223> OTHER INFORMATION: mutated heat shock protein peptide

<400> SEQUENCE: 9

Lys Asp Glu Leu
 1

<210> SEQ ID NO 10
<211> LENGTH: 10
<212> TYPE: PRT
<213> ORGANISM: Adeno Virus

<400> SEQUENCE: 10

Ser Gly Pro Ser Asn Thr Pro Pro Glu Ile
 1               5                  10

<210> SEQ ID NO 11
<211> LENGTH: 11
<212> TYPE: PRT
<213> ORGANISM: Lymphocytic Choriomeningitis Virus (LCMV)

<400> SEQUENCE: 11

Ser Gly Val Glu Asn Pro Gly Gly Tyr Cys Leu
 1               5                  10

<210> SEQ ID NO 12
<211> LENGTH: 10
<212> TYPE: PRT
<213> ORGANISM: Lymphocytic Choriomeningitis Virus (LCMV)

<400> SEQUENCE: 12

Lys Ala Val Tyr Asn Phe Ala Thr Cys Gly
 1               5                  10

<210> SEQ ID NO 13
<211> LENGTH: 9
<212> TYPE: PRT
<213> ORGANISM: Lymphocytic Choriomeningitis Virus (LCMV)

<400> SEQUENCE: 13

Arg Pro Gln Ala Ser Gly Val Tyr Met
 1               5

<210> SEQ ID NO 14
<211> LENGTH: 9
<212> TYPE: PRT
<213> ORGANISM: Lymphocytic Choriomeningitis Virus (LCMV)

<400> SEQUENCE: 14
```

```
Phe Gln Pro Gln Asn Gly Gln Phe Ile
  1               5

<210> SEQ ID NO 15
<211> LENGTH: 9
<212> TYPE: PRT
<213> ORGANISM: Influenza Virus

<400> SEQUENCE: 15

Ile Glu Gly Gly Trp Thr Gly Met Ile
  1               5

<210> SEQ ID NO 16
<211> LENGTH: 10
<212> TYPE: PRT
<213> ORGANISM: Influenza Virus

<400> SEQUENCE: 16

Thr Tyr Val Ser Val Ser Thr Ser Thr Leu
  1               5                  10

<210> SEQ ID NO 17
<211> LENGTH: 8
<212> TYPE: PRT
<213> ORGANISM: Influenza Virus

<400> SEQUENCE: 17

Phe Glu Ala Asn Gly Asn Leu Ile
  1               5

<210> SEQ ID NO 18
<211> LENGTH: 9
<212> TYPE: PRT
<213> ORGANISM: Influenza Virus

<400> SEQUENCE: 18

Ile Tyr Ser Thr Val Ala Ser Ser Leu
  1               5

<210> SEQ ID NO 19
<211> LENGTH: 9
<212> TYPE: PRT
<213> ORGANISM: Influenza Virus

<400> SEQUENCE: 19

Thr Tyr Gln Arg Thr Arg Ala Leu Val
  1               5

<210> SEQ ID NO 20
<211> LENGTH: 9
<212> TYPE: PRT
<213> ORGANISM: Influenza Virus

<400> SEQUENCE: 20

Cys Thr Glu Leu Lys Leu Ser Asp Tyr
  1               5

<210> SEQ ID NO 21
<211> LENGTH: 8
<212> TYPE: PRT
<213> ORGANISM: Influenza Virus

<400> SEQUENCE: 21

Ser Asp Tyr Glu Gly Arg Leu Ile
```

<210> SEQ ID NO 22
<211> LENGTH: 9
<212> TYPE: PRT
<213> ORGANISM: Influenza Virus

<400> SEQUENCE: 22

Glu Glu Gly Ala Ile Val Gly Glu Ile
1               5

<210> SEQ ID NO 23
<211> LENGTH: 9
<212> TYPE: PRT
<213> ORGANISM: Influenza Virus

<400> SEQUENCE: 23

Val Ser Asp Gly Gly Pro Asn Leu Tyr
1               5

<210> SEQ ID NO 24
<211> LENGTH: 9
<212> TYPE: PRT
<213> ORGANISM: Influenza Virus

<400> SEQUENCE: 24

Ala Ser Asn Glu Asn Met Glu Thr Met
1               5

<210> SEQ ID NO 25
<211> LENGTH: 9
<212> TYPE: PRT
<213> ORGANISM: Influenza Virus

<400> SEQUENCE: 25

Ala Ser Asn Glu Asn Met Asp Ala Met
1               5

<210> SEQ ID NO 26
<211> LENGTH: 10
<212> TYPE: PRT
<213> ORGANISM: Influenza Virus

<400> SEQUENCE: 26

Lys Leu Gly Glu Phe Tyr Asn Gln Met Met
1               5                   10

<210> SEQ ID NO 27
<211> LENGTH: 9
<212> TYPE: PRT
<213> ORGANISM: Influenza Virus

<400> SEQUENCE: 27

Leu Tyr Gln Asn Val Gly Thr Tyr Val
1               5

<210> SEQ ID NO 28
<211> LENGTH: 10
<212> TYPE: PRT
<213> ORGANISM: Influenza Virus

<400> SEQUENCE: 28

Thr Tyr Val Ser Val Gly Thr Ser Thr Leu
1               5                   10

```
<210> SEQ ID NO 29
<211> LENGTH: 8
<212> TYPE: PRT
<213> ORGANISM: Influenza Virus

<400> SEQUENCE: 29

Phe Glu Ser Thr Gly Asn Leu Ile
1               5

<210> SEQ ID NO 30
<211> LENGTH: 9
<212> TYPE: PRT
<213> ORGANISM: Influenza Virus

<400> SEQUENCE: 30

Val Tyr Gln Ile Leu Ala Ile Tyr Ala
1               5

<210> SEQ ID NO 31
<211> LENGTH: 9
<212> TYPE: PRT
<213> ORGANISM: Influenza Virus

<400> SEQUENCE: 31

Ile Tyr Ala Thr Val Ala Gly Ser Leu
1               5

<210> SEQ ID NO 32
<211> LENGTH: 9
<212> TYPE: PRT
<213> ORGANISM: Influenza Virus

<400> SEQUENCE: 32

Gly Ile Leu Gly Phe Val Phe Thr Leu
1               5

<210> SEQ ID NO 33
<211> LENGTH: 10
<212> TYPE: PRT
<213> ORGANISM: Influenza Virus

<400> SEQUENCE: 33

Ile Leu Gly Phe Val Phe Thr Leu Thr Val
1               5                   10

<210> SEQ ID NO 34
<211> LENGTH: 9
<212> TYPE: PRT
<213> ORGANISM: Influenza Virus

<400> SEQUENCE: 34

Ile Leu Arg Gly Ser Val Ala His Lys
1               5

<210> SEQ ID NO 35
<211> LENGTH: 9
<212> TYPE: PRT
<213> ORGANISM: Influenza Virus

<400> SEQUENCE: 35

Glu Asp Leu Arg Val Leu Ser Phe Ile
1               5

<210> SEQ ID NO 36
```

```
<211> LENGTH: 9
<212> TYPE: PRT
<213> ORGANISM: Influenza Virus

<400> SEQUENCE: 36

Glu Leu Arg Ser Arg Tyr Trp Ala Ile
1               5

<210> SEQ ID NO 37
<211> LENGTH: 9
<212> TYPE: PRT
<213> ORGANISM: Influenza Virus

<400> SEQUENCE: 37

Ser Arg Tyr Trp Ala Ile Arg Thr Arg
1               5

<210> SEQ ID NO 38
<211> LENGTH: 9
<212> TYPE: PRT
<213> ORGANISM: Influenza Virus

<400> SEQUENCE: 38

Lys Thr Gly Gly Pro Ile Tyr Lys Arg
1               5

<210> SEQ ID NO 39
<211> LENGTH: 9
<212> TYPE: PRT
<213> ORGANISM: Sendai Virus

<400> SEQUENCE: 39

Phe Ala Pro Gly Asn Tyr Pro Ala Leu
1               5

<210> SEQ ID NO 40
<211> LENGTH: 9
<212> TYPE: PRT
<213> ORGANISM: Measles Virus

<400> SEQUENCE: 40

Arg Arg Tyr Pro Asp Ala Val Tyr Leu
1               5

<210> SEQ ID NO 41
<211> LENGTH: 9
<212> TYPE: PRT
<213> ORGANISM: Measles Virus

<400> SEQUENCE: 41

Asp Pro Val Ile Asp Arg Leu Tyr Leu
1               5

<210> SEQ ID NO 42
<211> LENGTH: 9
<212> TYPE: PRT
<213> ORGANISM: Measles Virus

<400> SEQUENCE: 42

Ser Pro Gly Arg Ser Phe Ser Tyr Phe
1               5

<210> SEQ ID NO 43
<211> LENGTH: 9
<212> TYPE: PRT
```

```
<213> ORGANISM: Measles Virus

<400> SEQUENCE: 43

Tyr Pro Ala Leu Gly Leu His Glu Phe
 1               5

<210> SEQ ID NO 44
<211> LENGTH: 8
<212> TYPE: PRT
<213> ORGANISM: Polio Virus

<400> SEQUENCE: 44

Thr Tyr Lys Asp Thr Val Gln Leu
 1               5

<210> SEQ ID NO 45
<211> LENGTH: 10
<212> TYPE: PRT
<213> ORGANISM: Polio Virus

<400> SEQUENCE: 45

Phe Tyr Asp Gly Phe Ser Lys Val Pro Leu
 1               5                  10

<210> SEQ ID NO 46
<211> LENGTH: 11
<212> TYPE: PRT
<213> ORGANISM: Human Cytomegalovirus (HCMV)

<400> SEQUENCE: 46

Phe Ile Ala Gly Asn Ser Ala Tyr Glu Tyr Val
 1               5                  10

<210> SEQ ID NO 47
<211> LENGTH: 9
<212> TYPE: PRT
<213> ORGANISM: Mouse Cytomegalovirus (MCMV)

<400> SEQUENCE: 47

Tyr Pro His Phe Met Pro Thr Asn Leu
 1               5

<210> SEQ ID NO 48
<211> LENGTH: 9
<212> TYPE: PRT
<213> ORGANISM: Coronavirus

<400> SEQUENCE: 48

Ala Pro Thr Ala Gly Ala Phe Phe Phe
 1               5

<210> SEQ ID NO 49
<211> LENGTH: 11
<212> TYPE: PRT
<213> ORGANISM: Hepatitis B Virus

<400> SEQUENCE: 49

Ser Thr Leu Pro Glu Thr Thr Val Val Arg Arg
 1               5                  10

<210> SEQ ID NO 50
<211> LENGTH: 10
<212> TYPE: PRT
<213> ORGANISM: Hepatitis B Virus
```

```
<400> SEQUENCE: 50

Phe Leu Pro Ser Asp Phe Phe Pro Ser Val
1               5                   10

<210> SEQ ID NO 51
<211> LENGTH: 9
<212> TYPE: PRT
<213> ORGANISM: Hepatitis B Virus

<400> SEQUENCE: 51

Trp Leu Ser Leu Leu Val Pro Phe Val
1               5

<210> SEQ ID NO 52
<211> LENGTH: 10
<212> TYPE: PRT
<213> ORGANISM: Hepatitis B Virus

<400> SEQUENCE: 52

Gly Leu Ser Pro Thr Val Trp Leu Ser Val
1               5                   10

<210> SEQ ID NO 53
<211> LENGTH: 9
<212> TYPE: PRT
<213> ORGANISM: Hepatitis C Virus

<400> SEQUENCE: 53

Asp Leu Met Gly Tyr Ile Pro Leu Val
1               5

<210> SEQ ID NO 54
<211> LENGTH: 10
<212> TYPE: PRT
<213> ORGANISM: Hepatitis C Virus

<400> SEQUENCE: 54

Leu Met Gly Tyr Ile Pro Leu Val Gly Ala
1               5                   10

<210> SEQ ID NO 55
<211> LENGTH: 8
<212> TYPE: PRT
<213> ORGANISM: Hepatitis C Virus

<400> SEQUENCE: 55

Ala Ser Arg Cys Trp Val Ala Met
1               5

<210> SEQ ID NO 56
<211> LENGTH: 10
<212> TYPE: PRT
<213> ORGANISM: Hepatitis C Virus

<400> SEQUENCE: 56

Lys Leu Val Ala Leu Gly Ile Asn Ala Val
1               5                   10

<210> SEQ ID NO 57
<211> LENGTH: 9
<212> TYPE: PRT
<213> ORGANISM: Epstein Barr Virus

<400> SEQUENCE: 57
```

```
Phe Leu Arg Gly Arg Ala Tyr Gly Leu
 1               5
```

<210> SEQ ID NO 58
<211> LENGTH: 9
<212> TYPE: PRT
<213> ORGANISM: Epstein Barr Virus

<400> SEQUENCE: 58

```
Arg Arg Ile Tyr Asp Leu Ile Glu Leu
 1               5
```

<210> SEQ ID NO 59
<211> LENGTH: 9
<212> TYPE: PRT
<213> ORGANISM: Epstein Barr Virus

<400> SEQUENCE: 59

```
Ile Val Thr Asp Phe Ser Val Ile Lys
 1               5
```

<210> SEQ ID NO 60
<211> LENGTH: 9
<212> TYPE: PRT
<213> ORGANISM: Epstein Barr Virus

<400> SEQUENCE: 60

```
Arg Arg Arg Trp Arg Arg Leu Thr Val
 1               5
```

<210> SEQ ID NO 61
<211> LENGTH: 10
<212> TYPE: PRT
<213> ORGANISM: Epstein Barr Virus

<400> SEQUENCE: 61

```
Glu Glu Asn Leu Leu Asp Phe Val Arg Phe
 1               5                  10
```

<210> SEQ ID NO 62
<211> LENGTH: 9
<212> TYPE: PRT
<213> ORGANISM: Epstein Barr Virus

<400> SEQUENCE: 62

```
Cys Leu Gly Gly Leu Leu Thr Met Val
 1               5
```

<210> SEQ ID NO 63
<211> LENGTH: 8
<212> TYPE: PRT
<213> ORGANISM: Herpes Simplex Virus

<400> SEQUENCE: 63

```
Ser Ser Ile Glu Phe Ala Arg Leu
 1               5
```

<210> SEQ ID NO 64
<211> LENGTH: 11
<212> TYPE: PRT
<213> ORGANISM: Herpes Simplex Virus

<400> SEQUENCE: 64

```
Leu Tyr Arg Thr Phe Ala Gly Asn Pro Arg Ala
 1               5                  10
```

```
<210> SEQ ID NO 65
<211> LENGTH: 9
<212> TYPE: PRT
<213> ORGANISM: Herpes Simplex Virus

<400> SEQUENCE: 65

Asp Tyr Ala Thr Leu Gly Val Gly Val
 1               5

<210> SEQ ID NO 66
<211> LENGTH: 9
<212> TYPE: PRT
<213> ORGANISM: Human Papilloma Virus

<400> SEQUENCE: 66

Leu Leu Leu Gly Thr Leu Asn Ile Val
 1               5

<210> SEQ ID NO 67
<211> LENGTH: 9
<212> TYPE: PRT
<213> ORGANISM: Human Papilloma Virus

<400> SEQUENCE: 67

Leu Leu Met Gly Thr Leu Gly Ile Val
 1               5

<210> SEQ ID NO 68
<211> LENGTH: 9
<212> TYPE: PRT
<213> ORGANISM: Human Papilloma Virus

<400> SEQUENCE: 68

Thr Leu Gln Asp Ile Val Leu His Leu
 1               5

<210> SEQ ID NO 69
<211> LENGTH: 9
<212> TYPE: PRT
<213> ORGANISM: Human Papilloma Virus

<400> SEQUENCE: 69

Gly Leu His Cys Tyr Glu Gln Leu Val
 1               5

<210> SEQ ID NO 70
<211> LENGTH: 9
<212> TYPE: PRT
<213> ORGANISM: Human Papilloma Virus

<400> SEQUENCE: 70

Pro Leu Lys Gln His Phe Gln Ile Val
 1               5

<210> SEQ ID NO 71
<211> LENGTH: 9
<212> TYPE: PRT
<213> ORGANISM: Human Papilloma Virus

<400> SEQUENCE: 71

Arg Leu Val Thr Leu Lys Asp Ile Val
 1               5
```

<210> SEQ ID NO 72
<211> LENGTH: 9
<212> TYPE: PRT
<213> ORGANISM: Human Papilloma Virus

<400> SEQUENCE: 72

Arg Ala His Tyr Asn Ile Val Thr Phe
1               5

<210> SEQ ID NO 73
<211> LENGTH: 9
<212> TYPE: PRT
<213> ORGANISM: Human T-cell Leukemia Virus

<400> SEQUENCE: 73

Leu Leu Phe Gly Tyr Pro Val Tyr Val
1               5

<210> SEQ ID NO 74
<211> LENGTH: 10
<212> TYPE: PRT
<213> ORGANISM: Simian Virus 40

<400> SEQUENCE: 74

Ser Ala Ile Asn Asn Tyr Ala Gln Lys Leu
1               5                   10

<210> SEQ ID NO 75
<211> LENGTH: 9
<212> TYPE: PRT
<213> ORGANISM: Human Immunodeficiency Virus

<400> SEQUENCE: 75

His Gln Ala Ile Ser Pro Arg Thr Leu
1               5

<210> SEQ ID NO 76
<211> LENGTH: 12
<212> TYPE: PRT
<213> ORGANISM: Human Immunodeficiency Virus

<400> SEQUENCE: 76

Gln Met Val His Gln Ala Ile Ser Pro Arg Thr Leu
1               5                   10

<210> SEQ ID NO 77
<211> LENGTH: 9
<212> TYPE: PRT
<213> ORGANISM: Simian Virus 40

<400> SEQUENCE: 77

Cys Lys Gly Val Asn Lys Glu Tyr Leu
1               5

<210> SEQ ID NO 78
<211> LENGTH: 9
<212> TYPE: PRT
<213> ORGANISM: Simian Virus 40

<400> SEQUENCE: 78

Gln Gly Ile Asn Asn Leu Asp Asn Leu
1               5

<210> SEQ ID NO 79
<211> LENGTH: 9

```
<212> TYPE: PRT
<213> ORGANISM: Simian Virus 40

<400> SEQUENCE: 79

Asn Asn Leu Asp Asn Leu Arg Asp Tyr
1               5

<210> SEQ ID NO 80
<211> LENGTH: 9
<212> TYPE: PRT
<213> ORGANISM: Simian Virus 40

<400> SEQUENCE: 80

Ser Glu Phe Leu Leu Glu Lys Arg Ile
1               5

<210> SEQ ID NO 81
<211> LENGTH: 9
<212> TYPE: PRT
<213> ORGANISM: Raspiratory Syncytial Virus

<400> SEQUENCE: 81

Ser Tyr Ile Gly Ser Ile Asn Asn Ile
1               5

<210> SEQ ID NO 82
<211> LENGTH: 10
<212> TYPE: PRT
<213> ORGANISM: Human Immunodeficiency Virus

<400> SEQUENCE: 82

Ile Leu Gly Asn Lys Ile Val Arg Met Tyr
1               5                   10

<210> SEQ ID NO 83
<211> LENGTH: 9
<212> TYPE: PRT
<213> ORGANISM: Human Immunodeficiency Virus

<400> SEQUENCE: 83

Arg Leu Arg Pro Gly Gly Lys Lys Lys
1               5

<210> SEQ ID NO 84
<211> LENGTH: 9
<212> TYPE: PRT
<213> ORGANISM: Human Immunodeficiency Virus

<400> SEQUENCE: 84

Glu Ile Lys Asp Thr Lys Glu Ala Leu
1               5

<210> SEQ ID NO 85
<211> LENGTH: 9
<212> TYPE: PRT
<213> ORGANISM: Human Immunodeficiency Virus

<400> SEQUENCE: 85

Gly Glu Ile Tyr Lys Arg Trp Ile Ile
1               5

<210> SEQ ID NO 86
<211> LENGTH: 9
<212> TYPE: PRT
<213> ORGANISM: Human Immunodeficiency Virus
```

<400> SEQUENCE: 86

Glu Ile Tyr Lys Arg Trp Ile Ile Leu
1               5

<210> SEQ ID NO 87
<211> LENGTH: 9
<212> TYPE: PRT
<213> ORGANISM: Human Immunodeficiency Virus

<400> SEQUENCE: 87

Arg Tyr Leu Lys Asp Gln Gln Leu Leu
1               5

<210> SEQ ID NO 88
<211> LENGTH: 10
<212> TYPE: PRT
<213> ORGANISM: Human Immunodeficiency Virus

<400> SEQUENCE: 88

Arg Gly Pro Gly Arg Ala Phe Val Thr Ile
1               5                   10

<210> SEQ ID NO 89
<211> LENGTH: 9
<212> TYPE: PRT
<213> ORGANISM: Human Immunodeficiency Virus

<400> SEQUENCE: 89

Ile Val Gly Leu Asn Lys Ile Val Arg
1               5

<210> SEQ ID NO 90
<211> LENGTH: 10
<212> TYPE: PRT
<213> ORGANISM: Human Immunodeficiency Virus

<400> SEQUENCE: 90

Thr Val Tyr Tyr Gly Val Pro Val Trp Lys
1               5                   10

<210> SEQ ID NO 91
<211> LENGTH: 11
<212> TYPE: PRT
<213> ORGANISM: Human Immunodeficiency Virus

<400> SEQUENCE: 91

Arg Leu Arg Asp Leu Leu Leu Ile Val Thr Arg
1               5                   10

<210> SEQ ID NO 92
<211> LENGTH: 10
<212> TYPE: PRT
<213> ORGANISM: Human Immunodeficiency Virus

<400> SEQUENCE: 92

Lys Arg Trp Ile Ile Leu Gly Leu Asn Lys
1               5                   10

<210> SEQ ID NO 93
<211> LENGTH: 9
<212> TYPE: PRT
<213> ORGANISM: Human Immunodeficiency Virus

<400> SEQUENCE: 93

```
Ser Phe Asn Cys Gly Gly Glu Phe Phe
1               5

<210> SEQ ID NO 94
<211> LENGTH: 9
<212> TYPE: PRT
<213> ORGANISM: Human Immunodeficiency Virus

<400> SEQUENCE: 94

Gly Arg Ala Phe Val Thr Ile Gly Lys
1               5

<210> SEQ ID NO 95
<211> LENGTH: 10
<212> TYPE: PRT
<213> ORGANISM: Human Immunodeficiency Virus

<400> SEQUENCE: 95

Thr Pro Gly Pro Gly Val Arg Tyr Pro Leu
1               5                   10

<210> SEQ ID NO 96
<211> LENGTH: 10
<212> TYPE: PRT
<213> ORGANISM: Human Immunodeficiency Virus

<400> SEQUENCE: 96

Gln Val Pro Leu Arg Pro Met Thr Tyr Lys
1               5                   10

<210> SEQ ID NO 97
<211> LENGTH: 9
<212> TYPE: PRT
<213> ORGANISM: Human Immunodeficiency Virus

<400> SEQUENCE: 97

Thr Glu Met Glu Lys Glu Gly Lys Ile
1               5

<210> SEQ ID NO 98
<211> LENGTH: 9
<212> TYPE: PRT
<213> ORGANISM: Human Immunodeficiency Virus

<400> SEQUENCE: 98

Ile Leu Lys Glu Pro Val His Gly Val
1               5

<210> SEQ ID NO 99
<211> LENGTH: 9
<212> TYPE: PRT
<213> ORGANISM: Rabies Virus

<400> SEQUENCE: 99

Val Glu Ala Glu Ile Ala His Gln Ile
1               5

<210> SEQ ID NO 100
<211> LENGTH: 8
<212> TYPE: PRT
<213> ORGANISM: Vesicular Stomatitis Virus

<400> SEQUENCE: 100

Arg Gly Tyr Val Tyr Gln Gly Leu
```

```
<210> SEQ ID NO 101
<211> LENGTH: 9
<212> TYPE: PRT
<213> ORGANISM: Rotavirus

<400> SEQUENCE: 101

Tyr Ser Gly Tyr Ile Phe Arg Asp Leu
1               5

<210> SEQ ID NO 102
<211> LENGTH: 9
<212> TYPE: PRT
<213> ORGANISM: Rotavirus

<400> SEQUENCE: 102

Val Gly Pro Val Phe Pro Pro Gly Met
1               5

<210> SEQ ID NO 103
<211> LENGTH: 8
<212> TYPE: PRT
<213> ORGANISM: Rotavirus

<400> SEQUENCE: 103

Ile Ile Tyr Arg Phe Leu Leu Ile
1               5

<210> SEQ ID NO 104
<211> LENGTH: 9
<212> TYPE: PRT
<213> ORGANISM: Listeria innocua

<400> SEQUENCE: 104

Lys Tyr Gly Val Ser Val Gln Asp Ile
1               5

<210> SEQ ID NO 105
<211> LENGTH: 9
<212> TYPE: PRT
<213> ORGANISM: Yersinia pseudotuberculosis

<400> SEQUENCE: 105

Ile Gln Val Gly Asn Thr Arg Thr Ile
1               5

<210> SEQ ID NO 106
<211> LENGTH: 9
<212> TYPE: PRT
<213> ORGANISM: E.coli

<400> SEQUENCE: 106

Thr Pro His Pro Ala Arg Ile Gly Leu
1               5

<210> SEQ ID NO 107
<211> LENGTH: 9
<212> TYPE: PRT
<213> ORGANISM: P. falciparum

<400> SEQUENCE: 107

Ser Tyr Ile Pro Ser Ala Glu Lys Ile
1               5
```

```
<210> SEQ ID NO 108
<211> LENGTH: 8
<212> TYPE: PRT
<213> ORGANISM: P. falciparum

<400> SEQUENCE: 108

Lys Pro Lys Asp Glu Leu Asp Tyr
1               5

<210> SEQ ID NO 109
<211> LENGTH: 8
<212> TYPE: PRT
<213> ORGANISM: P. falciparum

<400> SEQUENCE: 109

Lys Ser Lys Asp Glu Leu Asp Tyr
1               5

<210> SEQ ID NO 110
<211> LENGTH: 8
<212> TYPE: PRT
<213> ORGANISM: P. falciparum

<400> SEQUENCE: 110

Lys Pro Asn Asp Lys Ser Leu Tyr
1               5

<210> SEQ ID NO 111
<211> LENGTH: 10
<212> TYPE: PRT
<213> ORGANISM: P. falciparum

<400> SEQUENCE: 111

Lys Tyr Leu Lys Lys Ile Lys Asn Ser Leu
1               5                   10

<210> SEQ ID NO 112
<211> LENGTH: 9
<212> TYPE: PRT
<213> ORGANISM: P. falciparum

<400> SEQUENCE: 112

Tyr Glu Asn Asp Ile Glu Lys Lys Ile
1               5

<210> SEQ ID NO 113
<211> LENGTH: 9
<212> TYPE: PRT
<213> ORGANISM: P. falciparum

<400> SEQUENCE: 113

Asn Tyr Asp Asn Ala Gly Thr Asn Leu
1               5

<210> SEQ ID NO 114
<211> LENGTH: 9
<212> TYPE: PRT
<213> ORGANISM: P. falciparum

<400> SEQUENCE: 114

Asp Glu Leu Asp Tyr Glu Asn Asp Ile
1               5

<210> SEQ ID NO 115
```

```
<211> LENGTH: 9
<212> TYPE: PRT
<213> ORGANISM: P. yoelii

<400> SEQUENCE: 115

Ser Tyr Val Pro Ser Ala Glu Gln Ile
1               5

<210> SEQ ID NO 116
<211> LENGTH: 8
<212> TYPE: PRT
<213> ORGANISM: Homo sapiens

<400> SEQUENCE: 116

Phe Glu Gln Asn Thr Ala Gln Pro
1               5

<210> SEQ ID NO 117
<211> LENGTH: 8
<212> TYPE: PRT
<213> ORGANISM: Homo sapiens

<400> SEQUENCE: 117

Phe Glu Gln Asn Thr Ala Gln Ala
1               5

<210> SEQ ID NO 118
<211> LENGTH: 9
<212> TYPE: PRT
<213> ORGANISM: Homo sapiens

<400> SEQUENCE: 118

Glu Ala Asp Pro Thr Gly His Ser Tyr
1               5

<210> SEQ ID NO 119
<211> LENGTH: 9
<212> TYPE: PRT
<213> ORGANISM: Homo sapiens

<400> SEQUENCE: 119

Glu Val Asp Pro Ile Gly His Leu Tyr
1               5

<210> SEQ ID NO 120
<211> LENGTH: 9
<212> TYPE: PRT
<213> ORGANISM: Homo sapiens

<400> SEQUENCE: 120

Ala Ala Gly Ile Gly Ile Leu Thr Val
1               5

<210> SEQ ID NO 121
<211> LENGTH: 9
<212> TYPE: PRT
<213> ORGANISM: Homo sapiens

<400> SEQUENCE: 121

Tyr Leu Glu Pro Gly Pro Val Thr Ala
1               5

<210> SEQ ID NO 122
<211> LENGTH: 10
<212> TYPE: PRT
```

```
<213> ORGANISM: Homo sapiens

<400> SEQUENCE: 122

Ile Leu Asp Gly Thr Ala Thr Leu Arg Leu
1               5                   10

<210> SEQ ID NO 123
<211> LENGTH: 9
<212> TYPE: PRT
<213> ORGANISM: Homo sapiens

<400> SEQUENCE: 123

Met Leu Leu Ala Leu Leu Tyr Cys Leu
1               5

<210> SEQ ID NO 124
<211> LENGTH: 9
<212> TYPE: PRT
<213> ORGANISM: Homo sapiens

<400> SEQUENCE: 124

Tyr Met Asn Gly Thr Met Ser Gln Val
1               5

<210> SEQ ID NO 125
<211> LENGTH: 9
<212> TYPE: PRT
<213> ORGANISM: Homo sapiens

<400> SEQUENCE: 125

Leu Pro Tyr Leu Gly Trp Leu Val Phe
1               5

<210> SEQ ID NO 126
<211> LENGTH: 9
<212> TYPE: PRT
<213> ORGANISM: Homo sapiens

<400> SEQUENCE: 126

Phe Gly Pro Tyr Lys Leu Asn Arg Leu
1               5

<210> SEQ ID NO 127
<211> LENGTH: 8
<212> TYPE: PRT
<213> ORGANISM: Homo sapiens

<400> SEQUENCE: 127

Lys Ser Pro Trp Phe Thr Thr Leu
1               5

<210> SEQ ID NO 128
<211> LENGTH: 10
<212> TYPE: PRT
<213> ORGANISM: Homo sapiens

<400> SEQUENCE: 128

Gly Pro Pro His Ser Asn Asn Phe Gly Tyr
1               5                   10

<210> SEQ ID NO 129
<211> LENGTH: 9
<212> TYPE: PRT
<213> ORGANISM: Homo sapiens
```

```
<400> SEQUENCE: 129

Ile Ser Thr Gln Asn His Arg Ala Leu
 1               5

<210> SEQ ID NO 130
<211> LENGTH: 10
<212> TYPE: PRT
<213> ORGANISM: Infleuenza Virus

<400> SEQUENCE: 130

Tyr Gly Ile Leu Gly Lys Val Phe Thr Leu
 1               5                  10

<210> SEQ ID NO 131
<211> LENGTH: 9
<212> TYPE: PRT
<213> ORGANISM: Human Immunodeficiency Virus

<400> SEQUENCE: 131

Ser Leu Tyr Asn Thr Val Ala Thr Leu
 1               5

<210> SEQ ID NO 132
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 132

Gly Lys Trp Val Tyr Ile Gly Trp
 1               5

<210> SEQ ID NO 133
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 133

Ala Lys Arg Glu Thr Lys Gly Trp
 1               5

<210> SEQ ID NO 134
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 134

Lys Trp Val His Leu Phe Gly Trp
 1               5

<210> SEQ ID NO 135
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 135
```

```
Arg Leu Val Leu Val Leu Gly Trp
 1               5
```

<210> SEQ ID NO 136
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 136

```
Trp Lys Trp Gly Ile Tyr Gly Trp
 1               5
```

<210> SEQ ID NO 137
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 137

```
Ser Ser His Ala Ser Ala Gly Trp
 1               5
```

<210> SEQ ID NO 138
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 138

```
Trp Gly Pro Trp Ser Phe Gly Trp
 1               5
```

<210> SEQ ID NO 139
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 139

```
Ala Ile Pro Gly Lys Val Gly Trp
 1               5
```

<210> SEQ ID NO 140
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 140

```
Arg Val His Asp Pro Ala Gly Trp
 1               5
```

<210> SEQ ID NO 141
<211> LENGTH: 8
<212> TYPE: PRT
<213> ORGANISM: Artificial Sequence

```
<220> FEATURE:
<223> OTHER INFORMATION: Heat shock protein binding domain with a
      terminal Trp residue

<400> SEQUENCE: 141

Arg Ser Val Ser Ser Phe Gly Trp
1               5

<210> SEQ ID NO 142
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 142

Leu Gly Thr Arg Lys Gly Gly Trp
1               5

<210> SEQ ID NO 143
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 143

Lys Asp Pro Leu Phe Asn Gly Trp
1               5

<210> SEQ ID NO 144
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 144

Leu Ser Gln His Thr Asn Gly Trp
1               5

<210> SEQ ID NO 145
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 145

Asn Arg Leu Leu Leu Thr Gly Trp
1               5

<210> SEQ ID NO 146
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 146

Tyr Pro Leu Trp Val Ile Gly Trp
1               5
```

<210> SEQ ID NO 147
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 147

Leu Leu Ile Ile Asp Arg Gly Trp
 1               5

<210> SEQ ID NO 148
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 148

Arg Val Ile Ser Leu Gln Gly Trp
 1               5

<210> SEQ ID NO 149
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 149

Glu Val Ser Arg Glu Asp Gly Trp
 1               5

<210> SEQ ID NO 150
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 150

Ser Ile Leu Arg Ser Thr Gly Trp
 1               5

<210> SEQ ID NO 151
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 151

Pro Gly Leu Val Trp Leu Gly Trp
 1               5

<210> SEQ ID NO 152
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue -continued

```
<400> SEQUENCE: 152

Val Lys Lys Leu Tyr Ile Gly Trp
 1               5

<210> SEQ ID NO 153
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 153

Asn Asn Arg Leu Leu Asp Gly Trp
 1               5

<210> SEQ ID NO 154
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 154

Ser Lys Gly Arg Trp Gly Gly Trp
 1               5

<210> SEQ ID NO 155
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 155

Ile Arg Pro Ser Gly Ile Gly Trp
 1               5

<210> SEQ ID NO 156
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 156

Ala Ser Leu Cys Pro Thr Gly Trp
 1               5

<210> SEQ ID NO 157
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 157

Asp Val Pro Gly Leu Arg Gly Trp
 1               5

<210> SEQ ID NO 158
<211> LENGTH: 8
<212> TYPE: PRT
```

```
<213> ORGANISM: Artificial Sequence
<220> FEATURE:
<223> OTHER INFORMATION: Heat shock protein binding domain with a
      terminal Trp residue

<400> SEQUENCE: 158

Arg His Arg Glu Val Gln Gly Trp
1               5

<210> SEQ ID NO 159
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 159

Leu Ala Arg Lys Arg Ser Gly Trp
1               5

<210> SEQ ID NO 160
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 160

Ser Val Leu Asp His Val Gly Trp
1               5

<210> SEQ ID NO 161
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 161

Asn Leu Leu Arg Arg Ala Gly Trp
1               5

<210> SEQ ID NO 162
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 162

Ser Gly Ile Ser Ala Trp Gly Trp
1               5

<210> SEQ ID NO 163
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 163

Phe Tyr Phe Trp Val Arg Gly Trp
1               5
```

<210> SEQ ID NO 164
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 164

Lys Leu Phe Leu Pro Leu Gly Trp
1               5

<210> SEQ ID NO 165
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 165

Thr Pro Thr Leu Ser Asp Gly Trp
1               5

<210> SEQ ID NO 166
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 166

Thr His Ser Leu Ile Leu Gly Trp
1               5

<210> SEQ ID NO 167
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 167

Leu Leu Leu Leu Ser Arg Gly Trp
1               5

<210> SEQ ID NO 168
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 168

Leu Leu Arg Val Arg Ser Gly Trp
1               5

<210> SEQ ID NO 169
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 169

Glu Arg Arg Ser Arg Gly Gly Trp
1               5

<210> SEQ ID NO 170
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 170

Arg Met Leu Gln Leu Ala Gly Trp
1               5

<210> SEQ ID NO 171
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 171

Arg Gly Trp Ala Asn Ser Gly Trp
1               5

<210> SEQ ID NO 172
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 172

Arg Pro Phe Tyr Ser Tyr Gly Trp
1               5

<210> SEQ ID NO 173
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 173

Ser Ser Ser Trp Asn Ala Gly Trp
1               5

<210> SEQ ID NO 174
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 174

Leu Gly His Leu Glu Glu Gly Trp
1               5

<210> SEQ ID NO 175
<211> LENGTH: 8

```
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 175

Ser Ala Val Thr Asn Thr Gly Trp
 1               5

<210> SEQ ID NO 176
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 176

Leu Arg Arg Ala Ser Leu Trp
 1               5

<210> SEQ ID NO 177
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 177

Leu Arg Arg Trp Ser Leu Trp
 1               5

<210> SEQ ID NO 178
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 178

Lys Trp Val His Leu Phe Trp
 1               5

<210> SEQ ID NO 179
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 179

Asn Arg Leu Leu Leu Thr Trp
 1               5

<210> SEQ ID NO 180
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 180

Ala Arg Leu Leu Leu Thr Trp
```

```
<210> SEQ ID NO 181
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 181

Asn Ala Leu Leu Leu Thr Trp
1               5

<210> SEQ ID NO 182
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 182

Asn Arg Leu Ala Leu Thr Trp
1               5

<210> SEQ ID NO 183
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 183

Asn Leu Leu Arg Leu Thr Trp
1               5

<210> SEQ ID NO 184
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 184

Asn Arg Leu Trp Leu Thr Trp
1               5

<210> SEQ ID NO 185
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 185

Asn Arg Leu Leu Leu Ala Trp
1               5

<210> SEQ ID NO 186
<211> LENGTH: 8
<212> TYPE: PRT
<213> ORGANISM: Artificial Sequence
<220> FEATURE:
<223> OTHER INFORMATION: Heat shock protein binding domain with a
```

-continued terminal Trp residue

<400> SEQUENCE: 186

Phe Tyr Gln Leu Ala Leu Thr Trp
1               5

<210> SEQ ID NO 187
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 187

Phe Tyr Gln Leu Ala Leu Thr Trp
1               5

<210> SEQ ID NO 188
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 188

Arg Lys Leu Phe Phe Asn Leu Arg Trp
1               5

<210> SEQ ID NO 189
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 189

Arg Lys Leu Phe Phe Asn Leu Arg Trp
1               5

<210> SEQ ID NO 190
<211> LENGTH: 6
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 190

Lys Phe Glu Arg Gln Trp
1               5

<210> SEQ ID NO 191
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 191

Asn Ile Val Arg Lys Lys Lys Thr Arg
1               5

<210> SEQ ID NO 192

```
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 192

Arg Gly Tyr Val Tyr Gln Gly Leu Trp
1               5

<210> SEQ ID NO 193
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 193

Tyr Thr Leu Val Gln Pro Leu Trp
1               5

<210> SEQ ID NO 194
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 194

Thr Pro Asp Ile Thr Pro Lys Trp
1               5

<210> SEQ ID NO 195
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 195

Thr Tyr Pro Asp Leu Arg Tyr Trp
1               5

<210> SEQ ID NO 196
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 196

Asp Arg Thr His Ala Thr Ser Trp
1               5

<210> SEQ ID NO 197
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 197
```

```
Met Ser Thr Thr Phe Tyr Ser Trp
1               5

<210> SEQ ID NO 198
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 198

Tyr Gln His Ala Val Gln Thr Trp
1               5

<210> SEQ ID NO 199
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 199

Phe Pro Phe Ser Ala Ser Thr Trp
1               5

<210> SEQ ID NO 200
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 200

Ser Ser Phe Pro Pro Leu Asp Trp
1               5

<210> SEQ ID NO 201
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 201

Met Ala Pro Ser Pro Pro His Trp
1               5

<210> SEQ ID NO 202
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 202

Ser Ser Phe Pro Asp Leu Leu Trp
1               5

<210> SEQ ID NO 203
<211> LENGTH: 8
<212> TYPE: PRT
<213> ORGANISM: Artificial Sequence
<220> FEATURE:
```

<223> OTHER INFORMATION: Heat shock protein binding domain with a
      terminal Trp residue

<400> SEQUENCE: 203

His Ser Tyr Asn Arg Leu Pro Trp
1               5

<210> SEQ ID NO 204
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 204

His Leu Thr His Ser Gln Arg Trp
1               5

<210> SEQ ID NO 205
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 205

Gln Ala Ala Gln Ser Arg Ser Trp
1               5

<210> SEQ ID NO 206
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 206

Phe Ala Thr His His Ile Gly Trp
1               5

<210> SEQ ID NO 207
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 207

Ser Met Pro Glu Pro Leu Ile Trp
1               5

<210> SEQ ID NO 208
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 208

Ile Pro Arg Tyr His Leu Ile Trp
1               5

```
<210> SEQ ID NO 209
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 209

Ser Ala Pro His Met Thr Ser Trp
1               5

<210> SEQ ID NO 210
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 210

Lys Ala Pro Val Trp Ala Ser Trp
1               5

<210> SEQ ID NO 211
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 211

Leu Pro His Trp Leu Leu Ile Trp
1               5

<210> SEQ ID NO 212
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 212

Ala Ser Ala Gly Tyr Gln Ile Trp
1               5

<210> SEQ ID NO 213
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 213

Val Thr Pro Lys Thr Gly Ser Trp
1               5

<210> SEQ ID NO 214
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 214
```

```
Glu His Pro Met Pro Val Leu Trp
1               5

<210> SEQ ID NO 215
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 215

Val Ser Ser Phe Val Thr Ser Trp
1               5

<210> SEQ ID NO 216
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 216

Ser Thr His Phe Thr Trp Pro Trp
1               5

<210> SEQ ID NO 217
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 217

Gly Gln Trp Trp Ser Pro Asp Trp
1               5

<210> SEQ ID NO 218
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 218

Gly Pro Pro His Gln Asp Ser Trp
1               5

<210> SEQ ID NO 219
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 219

Asn Thr Leu Pro Ser Thr Ile Trp
1               5

<210> SEQ ID NO 220
<211> LENGTH: 8
<212> TYPE: PRT
<213> ORGANISM: Artificial Sequence
```

```
<220> FEATURE:
<223> OTHER INFORMATION: Heat shock protein binding domain with a
      terminal Trp residue

<400> SEQUENCE: 220

His Gln Pro Ser Arg Trp Val Trp
1               5

<210> SEQ ID NO 221
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 221

Tyr Gly Asn Pro Leu Gln Pro Trp
1               5

<210> SEQ ID NO 222
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 222

Phe His Trp Trp Trp Gln Pro Trp
1               5

<210> SEQ ID NO 223
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 223

Ile Thr Leu Lys Tyr Pro Leu Trp
1               5

<210> SEQ ID NO 224
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 224

Phe His Trp Pro Trp Leu Phe Trp
1               5

<210> SEQ ID NO 225
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 225

Thr Ala Gln Asp Ser Thr Gly Trp
1               5
```

```
<210> SEQ ID NO 226
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 226

Phe His Trp Trp Trp Gln Pro Trp
1               5

<210> SEQ ID NO 227
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 227

Phe His Trp Trp Asp Trp Trp Trp
1               5

<210> SEQ ID NO 228
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 228

Glu Pro Phe Phe Arg Met Gln Trp
1               5

<210> SEQ ID NO 229
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 229

Thr Trp Trp Leu Asn Tyr Arg Trp
1               5

<210> SEQ ID NO 230
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 230

Phe His Trp Trp Trp Gln Pro Trp
1               5

<210> SEQ ID NO 231
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
```

```
<400> SEQUENCE: 231

Gln Pro Ser His Leu Arg Trp Trp
1               5

<210> SEQ ID NO 232
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 232

Ser Pro Ala Ser Pro Val Tyr Trp
1               5

<210> SEQ ID NO 233
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 233

Phe His Trp Trp Trp Gln Pro Trp
1               5

<210> SEQ ID NO 234
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 234

His Pro Ser Asn Gln Ala Ser Trp
1               5

<210> SEQ ID NO 235
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 235

Asn Ser Ala Pro Arg Pro Val Trp
1               5

<210> SEQ ID NO 236
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 236

Gln Leu Trp Ser Ile Tyr Pro Trp
1               5

<210> SEQ ID NO 237
<211> LENGTH: 8
<212> TYPE: PRT
```

```
<213> ORGANISM: Artificial Sequence
<220> FEATURE:
<223> OTHER INFORMATION: Heat shock protein binding domain with a
      terminal Trp residue

<400> SEQUENCE: 237

Ser Trp Pro Phe Phe Asp Leu Trp
 1               5

<210> SEQ ID NO 238
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 238

Asp Thr Thr Leu Pro Leu His Trp
 1               5

<210> SEQ ID NO 239
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 239

Trp His Trp Gln Met Leu Trp Trp
 1               5

<210> SEQ ID NO 240
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 240

Asp Ser Phe Arg Thr Pro Val Trp
 1               5

<210> SEQ ID NO 241
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 241

Thr Ser Pro Leu Ser Leu Leu Trp
 1               5

<210> SEQ ID NO 242
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 242

Ala Tyr Asn Tyr Val Ser Asp Trp
 1               5
```

```
<210> SEQ ID NO 243
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 243

Arg Pro Leu His Asp Pro Met Trp
 1               5

<210> SEQ ID NO 244
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 244

Trp Pro Ser Thr Thr Leu Phe Trp
 1               5

<210> SEQ ID NO 245
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 245

Ala Thr Leu Glu Pro Val Arg Trp
 1               5

<210> SEQ ID NO 246
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 246

Ser Met Thr Val Leu Arg Pro Trp
 1               5

<210> SEQ ID NO 247
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 247

Gln Ile Gly Ala Pro Ser Trp Trp
 1               5

<210> SEQ ID NO 248
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
```

```
<400> SEQUENCE: 248

Ala Pro Asp Leu Tyr Val Pro Trp
1               5

<210> SEQ ID NO 249
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 249

Arg Met Pro Pro Leu Leu Pro Trp
1               5

<210> SEQ ID NO 250
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 250

Ala Lys Ala Thr Pro Glu His Trp
1               5

<210> SEQ ID NO 251
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 251

Thr Pro Pro Leu Arg Ile Asn Trp
1               5

<210> SEQ ID NO 252
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 252

Leu Pro Ile His Ala Pro His Trp
1               5

<210> SEQ ID NO 253
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 253

Asp Leu Asn Ala Tyr Thr His Trp
1               5

<210> SEQ ID NO 254
<211> LENGTH: 8
```

```
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 254

Val Thr Leu Pro Asn Phe His Trp
 1               5

<210> SEQ ID NO 255
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 255

Asn Ser Arg Leu Pro Thr Leu Trp
 1               5

<210> SEQ ID NO 256
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 256

Tyr Pro His Pro Ser Arg Ser Trp
 1               5

<210> SEQ ID NO 257
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 257

Gly Thr Ala His Phe Met Tyr Trp
 1               5

<210> SEQ ID NO 258
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 258

Tyr Ser Leu Leu Pro Thr Arg Trp
 1               5

<210> SEQ ID NO 259
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 259

Leu Pro Arg Arg Thr Leu Leu Trp
```

-continued

```
  1               5

<210> SEQ ID NO 260
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 260

Thr Ser Thr Leu Leu Trp Lys Trp
  1               5

<210> SEQ ID NO 261
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 261

Thr Ser Asp Met Lys Pro His Trp
  1               5

<210> SEQ ID NO 262
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 262

Thr Ser Ser Tyr Leu Ala Leu Trp
  1               5

<210> SEQ ID NO 263
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 263

Asn Leu Tyr Gly Pro His Asp Trp
  1               5

<210> SEQ ID NO 264
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 264

Leu Glu Thr Tyr Thr Ala Ser Trp
  1               5

<210> SEQ ID NO 265
<211> LENGTH: 8
<212> TYPE: PRT
<213> ORGANISM: Artificial Sequence
<220> FEATURE:
<223> OTHER INFORMATION: Heat shock protein binding domain with a
``` terminal Trp residue

<400> SEQUENCE: 265

Ala Tyr Lys Ser Leu Thr Gln Trp
1               5

<210> SEQ ID NO 266
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 266

Ser Thr Ser Val Tyr Ser Ser Trp
1               5

<210> SEQ ID NO 267
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 267

Glu Gly Pro Leu Arg Ser Pro Trp
1               5

<210> SEQ ID NO 268
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 268

Thr Thr Tyr His Ala Leu Gly Trp
1               5

<210> SEQ ID NO 269
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 269

Val Ser Ile Gly His Pro Ser Trp
1               5

<210> SEQ ID NO 270
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 270

Thr His Ser His Arg Pro Ser Trp
1               5

<210> SEQ ID NO 271

```
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 271

Ile Thr Asn Pro Leu Thr Thr Trp
 1               5

<210> SEQ ID NO 272
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 272

Ser Ile Gln Ala His His Ser Trp
 1               5

<210> SEQ ID NO 273
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 273

Leu Asn Trp Pro Arg Val Leu Trp
 1               5

<210> SEQ ID NO 274
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 274

Tyr Tyr Tyr Ala Pro Pro Pro Trp
 1               5

<210> SEQ ID NO 275
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 275

Ser Leu Trp Thr Arg Leu Pro Trp
 1               5

<210> SEQ ID NO 276
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 276
```

-continued

Asn Val Tyr His Ser Ser Leu Trp
 1               5

<210> SEQ ID NO 277
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 277

Asn Ser Pro His Pro Pro Thr Trp
 1               5

<210> SEQ ID NO 278
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 278

Val Pro Ala Lys Pro Arg His Trp
 1               5

<210> SEQ ID NO 279
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 279

His Asn Leu His Pro Asn Arg Trp
 1               5

<210> SEQ ID NO 280
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 280

Tyr Thr Thr His Arg Trp Leu Trp
 1               5

<210> SEQ ID NO 281
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 281

Ala Val Thr Ala Ala Ile Val Trp
 1               5

<210> SEQ ID NO 282
<211> LENGTH: 8
<212> TYPE: PRT
<213> ORGANISM: Artificial Sequence
<220> FEATURE:

```
<223> OTHER INFORMATION: Heat shock protein binding domain with a
      terminal Trp residue

<400> SEQUENCE: 282

Thr Leu Met His Asp Arg Val Trp
1               5

<210> SEQ ID NO 283
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 283

Thr Pro Leu Lys Val Pro Tyr Trp
1               5

<210> SEQ ID NO 284
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 284

Phe Thr Asn Gln Gln Tyr His Trp
1               5

<210> SEQ ID NO 285
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 285

Ser His Val Pro Ser Met Ala Trp
1               5

<210> SEQ ID NO 286
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 286

His Thr Thr Val Tyr Gly Ala Trp
1               5

<210> SEQ ID NO 287
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 287

Thr Glu Thr Pro Tyr Pro Thr Trp
1               5
```

```
<210> SEQ ID NO 288
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 288

Leu Thr Thr Pro Phe Ser Ser Trp
 1               5

<210> SEQ ID NO 289
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 289

Gly Val Pro Leu Thr Met Asp Trp
 1               5

<210> SEQ ID NO 290
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 290

Lys Leu Pro Thr Val Leu Arg Trp
 1               5

<210> SEQ ID NO 291
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 291

Cys Arg Phe His Gly Asn Arg Trp
 1               5

<210> SEQ ID NO 292
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 292

Tyr Thr Arg Asp Phe Glu Ala Trp
 1               5

<210> SEQ ID NO 293
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 293
```

Ser Ser Ala Ala Gly Pro Arg Trp
1               5

<210> SEQ ID NO 294
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 294

Ser Leu Ile Gln Tyr Ser Arg Trp
1               5

<210> SEQ ID NO 295
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
<220> FEATURE:
<221> NAME/KEY: VARIANT
<222> LOCATION: 7
<223> OTHER INFORMATION: Xaa = any amino acid

<400> SEQUENCE: 295

Asp Ala Leu Met Trp Pro Xaa Trp
1               5

<210> SEQ ID NO 296
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
<220> FEATURE:
<221> NAME/KEY: VARIANT
<222> LOCATION: 3
<223> OTHER INFORMATION: Xaa = any amino acid

<400> SEQUENCE: 296

Ser Ser Xaa Ser Leu Tyr Ile Trp
1               5

<210> SEQ ID NO 297
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 297

Phe Asn Thr Ser Thr Arg Thr Trp
1               5

<210> SEQ ID NO 298
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 298

```
Thr Val Gln His Val Ala Phe Trp
 1               5
```

<210> SEQ ID NO 299
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 299

```
Asp Tyr Ser Phe Pro Pro Leu Trp
 1               5
```

<210> SEQ ID NO 300
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 300

```
Val Gly Ser Met Glu Ser Leu Trp
 1               5
```

<210> SEQ ID NO 301
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
<220> FEATURE:
<221> NAME/KEY: VARIANT
<222> LOCATION: 2, 6
<223> OTHER INFORMATION: Xaa = any amino acid

<400> SEQUENCE: 301

```
Phe Xaa Pro Met Ile Xaa Ser Trp
 1               5
```

<210> SEQ ID NO 302
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 302

```
Ala Pro Pro Arg Val Thr Met Trp
 1               5
```

<210> SEQ ID NO 303
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 303

```
Ile Ala Thr Lys Thr Pro Lys Trp
 1               5
```

<210> SEQ ID NO 304

```
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 304

Lys Pro Pro Leu Phe Gln Ile Trp
1               5

<210> SEQ ID NO 305
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 305

Tyr His Thr Ala His Asn Met Trp
1               5

<210> SEQ ID NO 306
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 306

Ser Tyr Ile Gln Ala Thr His Trp
1               5

<210> SEQ ID NO 307
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 307

Ser Ser Phe Ala Thr Phe Leu Trp
1               5

<210> SEQ ID NO 308
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 308

Thr Thr Pro Pro Asn Phe Ala Trp
1               5

<210> SEQ ID NO 309
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 309
```

```
Ile Ser Leu Asp Pro Arg Met Trp
 1               5
```

<210> SEQ ID NO 310
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 310

```
Ser Leu Pro Leu Phe Gly Ala Trp
 1               5
```

<210> SEQ ID NO 311
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 311

```
Asn Leu Leu Lys Thr Thr Leu Trp
 1               5
```

<210> SEQ ID NO 312
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 312

```
Asp Gln Asn Leu Pro Arg Arg Trp
 1               5
```

<210> SEQ ID NO 313
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 313

```
Ser His Phe Glu Gln Leu Leu Trp
 1               5
```

<210> SEQ ID NO 314
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 314

```
Thr Pro Gln Leu His His Gly Trp
 1               5
```

<210> SEQ ID NO 315
<211> LENGTH: 8
<212> TYPE: PRT
<213> ORGANISM: Artificial Sequence
<220> FEATURE:

```
<223> OTHER INFORMATION: Heat shock protein binding domain with a
      terminal Trp residue

<400> SEQUENCE: 315

Ala Pro Leu Asp Arg Ile Thr Trp
1               5

<210> SEQ ID NO 316
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 316

Phe Ala Pro Leu Ile Ala His Trp
1               5

<210> SEQ ID NO 317
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 317

Ser Trp Ile Gln Thr Phe Met Trp
1               5

<210> SEQ ID NO 318
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 318

Asn Thr Trp Pro His Met Tyr Trp
1               5

<210> SEQ ID NO 319
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 319

Glu Pro Leu Pro Thr Thr Leu Trp
1               5

<210> SEQ ID NO 320
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 320

His Gly Pro His Leu Phe Asn Trp
1               5
```

```
<210> SEQ ID NO 321
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 321

Tyr Leu Asn Ser Thr Leu Ala Trp
1               5

<210> SEQ ID NO 322
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 322

His Leu His Ser Pro Ser Gly Trp
1               5

<210> SEQ ID NO 323
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 323

Thr Leu Pro His Arg Leu Asn Trp
1               5

<210> SEQ ID NO 324
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 324

Ser Ser Pro Arg Glu Val His Trp
1               5

<210> SEQ ID NO 325
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 325

Asn Gln Val Asp Thr Ala Arg Trp
1               5

<210> SEQ ID NO 326
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 326
```

Tyr Pro Thr Pro Leu Leu Thr Trp
1               5

<210> SEQ ID NO 327
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 327

His Pro Ala Ala Phe Pro Trp Trp
1               5

<210> SEQ ID NO 328
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 328

Leu Leu Pro His Ser Ser Ala Trp
1               5

<210> SEQ ID NO 329
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 329

Leu Glu Thr Tyr Thr Ala Ser Trp
1               5

<210> SEQ ID NO 330
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 330

Lys Tyr Val Pro Leu Pro Pro Trp
1               5

<210> SEQ ID NO 331
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 331

Ala Pro Leu Ala Leu His Ala Trp
1               5

<210> SEQ ID NO 332
<211> LENGTH: 8
<212> TYPE: PRT
<213> ORGANISM: Artificial Sequence

```
<220> FEATURE:
<223> OTHER INFORMATION: Heat shock protein binding domain with a
      terminal Trp residue

<400> SEQUENCE: 332

Tyr Glu Ser Leu Leu Thr Lys Trp
1               5

<210> SEQ ID NO 333
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 333

Ser His Ala Ala Ser Gly Thr Trp
1               5

<210> SEQ ID NO 334
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 334

Gly Leu Ala Thr Val Lys Ser Trp
1               5

<210> SEQ ID NO 335
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 335

Gly Ala Thr Ser Phe Gly Leu Trp
1               5

<210> SEQ ID NO 336
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 336

Lys Pro Pro Gly Pro Val Ser Trp
1               5

<210> SEQ ID NO 337
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 337

Thr Leu Tyr Val Ser Gly Asn Trp
1               5
```

```
<210> SEQ ID NO 338
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 338

His Ala Pro Phe Lys Ser Gln Trp
 1               5

<210> SEQ ID NO 339
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 339

Val Ala Phe Thr Arg Leu Pro Trp
 1               5

<210> SEQ ID NO 340
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 340

Leu Pro Thr Arg Thr Pro Ala Trp
 1               5

<210> SEQ ID NO 341
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 341

Ala Ser Phe Asp Leu Leu Ile Trp
 1               5

<210> SEQ ID NO 342
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 342

Arg Met Asn Thr Glu Pro Pro Trp
 1               5

<210> SEQ ID NO 343
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
```

```
<400> SEQUENCE: 343

Lys Met Thr Pro Leu Thr Thr Trp
1               5

<210> SEQ ID NO 344
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 344

Ala Asn Ala Thr Pro Leu Leu Trp
1               5

<210> SEQ ID NO 345
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 345

Thr Ile Trp Pro Pro Pro Val Trp
1               5

<210> SEQ ID NO 346
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 346

Gln Thr Lys Val Met Thr Thr Trp
1               5

<210> SEQ ID NO 347
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 347

Asn His Ala Val Phe Ala Ser Trp
1               5

<210> SEQ ID NO 348
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
<220> FEATURE:
<221> NAME/KEY: VARIANT
<222> LOCATION: 5
<223> OTHER INFORMATION: Xaa = any amino acid

<400> SEQUENCE: 348

Leu His Ala Ala Xaa Thr Ser Trp
1               5
```

```
<210> SEQ ID NO 349
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 349

Thr Trp Gln Pro Tyr Phe His Trp
 1               5

<210> SEQ ID NO 350
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 350

Ala Pro Leu Ala Leu His Ala Trp
 1               5

<210> SEQ ID NO 351
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 351

Thr Ala His Asp Leu Thr Val Trp
 1               5

<210> SEQ ID NO 352
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 352

Asn Met Thr Asn Met Leu Thr Trp
 1               5

<210> SEQ ID NO 353
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 353

Gly Ser Gly Leu Ser Gln Asp Trp
 1               5

<210> SEQ ID NO 354
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
```

```
<400> SEQUENCE: 354

Thr Pro Ile Lys Thr Ile Tyr Trp
1               5

<210> SEQ ID NO 355
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 355

Ser His Leu Tyr Arg Ser Ser Trp
1               5

<210> SEQ ID NO 356
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 356

His Gly Gln Ala Trp Gln Phe Trp
1               5

<210> SEQ ID NO 357
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 357

Ser Ile Ile Asn Phe Glu Lys Leu
1               5

<210> SEQ ID NO 358
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 358

His Trp Asp Phe Ala Trp Pro Trp
1               5

<210> SEQ ID NO 359
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 359

Asn Leu Leu Arg Leu Thr Gly Trp
1               5

<210> SEQ ID NO 360
<211> LENGTH: 8
<212> TYPE: PRT
<213> ORGANISM: Artificial Sequence
<220> FEATURE:
<223> OTHER INFORMATION: Heat shock protein binding domain
```

```
<400> SEQUENCE: 360

Phe Tyr Gln Leu Ala Leu Thr Trp
1               5

<210> SEQ ID NO 361
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 361

Arg Lys Leu Phe Phe Asn Leu Arg Trp
1               5

<210> SEQ ID NO 362
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 362

Ala Leu Phe Asp Ile Glu Ser Lys Val
1               5

<210> SEQ ID NO 363
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 363

Ile Met Asp Gln Val Pro Phe Ser Val
1               5

<210> SEQ ID NO 364
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 364

Tyr Met Asp Gly Thr Met Ser Gln Val
1               5

<210> SEQ ID NO 365
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 365

Thr Leu Gly Ile Val Cys Pro Ile
1               5

<210> SEQ ID NO 366
<211> LENGTH: 10
<212> TYPE: PRT
<213> ORGANISM: Artificial Sequence
<220> FEATURE:
<223> OTHER INFORMATION: Heat shock protein binding domain
```

-continued

```
<400> SEQUENCE: 366

Tyr Met Leu Asp Leu Gln Pro Glu Thr Thr
1               5                   10

<210> SEQ ID NO 367
<211> LENGTH: 19
<212> TYPE: PRT
<213> ORGANISM: Artificial Sequence
<220> FEATURE:
<223> OTHER INFORMATION: Hybrid antigen

<400> SEQUENCE: 367

Ser Ile Ile Asn Phe Glu Lys Leu Gly Ser Gly Asn Leu Leu Arg Leu
1               5                   10                  15

Thr Gly Trp

<210> SEQ ID NO 368
<211> LENGTH: 19
<212> TYPE: PRT
<213> ORGANISM: Artificial Sequence
<220> FEATURE:
<223> OTHER INFORMATION: Hybrid antigen

<400> SEQUENCE: 368

Ser Ile Ile Asn Phe Glu Lys Leu Gly Ser Gly His Trp Asp Phe Ala
1               5                   10                  15

Trp Pro Trp

<210> SEQ ID NO 369
<211> LENGTH: 20
<212> TYPE: PRT
<213> ORGANISM: Artificial Sequence
<220> FEATURE:
<223> OTHER INFORMATION: Hybrid antigen

<400> SEQUENCE: 369

Ala Leu Phe Asp Ile Glu Ser Lys Val Gly Ser Gly His Trp Asp Phe
1               5                   10                  15

Ala Trp Pro Trp
            20

<210> SEQ ID NO 370
<211> LENGTH: 8
<212> TYPE: PRT
<213> ORGANISM: Artificial Sequence
<220> FEATURE:
<223> OTHER INFORMATION: Hybrid antigen

<400> SEQUENCE: 370

Arg Gly Tyr Val Tyr Gln Gly Leu
1               5

<210> SEQ ID NO 371
<211> LENGTH: 20
<212> TYPE: PRT
<213> ORGANISM: Artificial Sequence
<220> FEATURE:
<223> OTHER INFORMATION: Heat shock protein binding domain

<400> SEQUENCE: 371

Ile Met Asp Gln Val Pro Phe Ser Val Gly Ser Gly His Trp Asp Phe
1               5                   10                  15

Ala Trp Pro Trp
            20
```

<210> SEQ ID NO 372
<211> LENGTH: 20
<212> TYPE: PRT
<213> ORGANISM: Artificial Sequence
<220> FEATURE:
<223> OTHER INFORMATION: Hybrid antigen

<400> SEQUENCE: 372

Ile Met Asp Gln Val Pro Phe Ser Val Gly Ser Gly Asn Leu Leu Arg
1               5                   10                  15
Leu Thr Gly Trp
            20

<210> SEQ ID NO 373
<211> LENGTH: 20
<212> TYPE: PRT
<213> ORGANISM: Artificial Sequence
<220> FEATURE:
<223> OTHER INFORMATION: Hybrid antigen

<400> SEQUENCE: 373

Tyr Met Asp Gly Thr Met Ser Gln Val Gly Ser Gly His Trp Asp Phe
1               5                   10                  15
Ala Trp Pro Trp
            20

<210> SEQ ID NO 374
<211> LENGTH: 20
<212> TYPE: PRT
<213> ORGANISM: Artificial Sequence
<220> FEATURE:
<223> OTHER INFORMATION: Hybrid antigen

<400> SEQUENCE: 374

His Trp Asp Phe Ala Trp Pro Trp Gly Ser Gly Tyr Met Asp Gly Thr
1               5                   10                  15
Met Ser Gln Val
            20

<210> SEQ ID NO 375
<211> LENGTH: 23
<212> TYPE: PRT
<213> ORGANISM: Artificial Sequence
<220> FEATURE:
<223> OTHER INFORMATION: Hybrid antigen

<400> SEQUENCE: 375

Tyr Met Asp Gly Thr Met Ser Gln Val Gly Ser Gly Gly Ser Gly Asn
1               5                   10                  15
Leu Leu Arg Leu Thr Gly Trp
            20

<210> SEQ ID NO 376
<211> LENGTH: 19
<212> TYPE: PRT
<213> ORGANISM: Artificial Sequence
<220> FEATURE:
<223> OTHER INFORMATION: Hybrid antigen

<400> SEQUENCE: 376

Thr Leu Gly Ile Val Cys Pro Ile Gly Ser Gly His Trp Asp Phe Ala
1               5                   10                  15
Trp Pro Trp

<210> SEQ ID NO 377
<211> LENGTH: 20
<212> TYPE: PRT
<213> ORGANISM: Artificial Sequence
<220> FEATURE:
<223> OTHER INFORMATION: Hybrid antigen

<400> SEQUENCE: 377

Thr Leu Gly Ile Val Cys Pro Ile Gly Ser Gly Asn Leu Leu Arg
 1               5                  10                  15

Leu Thr Gly Trp
            20

<210> SEQ ID NO 378
<211> LENGTH: 21
<212> TYPE: PRT
<213> ORGANISM: Artificial Sequence
<220> FEATURE:
<223> OTHER INFORMATION: Hybrid antigen

<400> SEQUENCE: 378

Tyr Met Leu Asp Leu Gln Pro Glu Thr Thr Gly Ser Gly His Trp Asp
 1               5                  10                  15

Phe Ala Trp Pro Trp
            20

<210> SEQ ID NO 379
<211> LENGTH: 19
<212> TYPE: PRT
<213> ORGANISM: Artificial Sequence
<220> FEATURE:
<223> OTHER INFORMATION: Hybrid antigen

<400> SEQUENCE: 379

His Trp Asp Phe Ala Trp Pro Trp Gly Ser Gly Ser Ile Ile Asn Phe
 1               5                  10                  15

Glu Lys Leu

<210> SEQ ID NO 380
<211> LENGTH: 19
<212> TYPE: PRT
<213> ORGANISM: Artificial Sequence
<220> FEATURE:
<223> OTHER INFORMATION: Hybrid antigen

<400> SEQUENCE: 380

Ser Ile Ile Asn Phe Glu Lys Leu Gly Ser Gly Asn Leu Leu Arg Leu
 1               5                  10                  15

Thr Gly Trp

<210> SEQ ID NO 381
<211> LENGTH: 19
<212> TYPE: PRT
<213> ORGANISM: Artificial Sequence
<220> FEATURE:
<223> OTHER INFORMATION: Hybrid antigen

<400> SEQUENCE: 381

Ser Ile Ile Asn Phe Glu Lys Leu Gly Ser Gly Phe Tyr Gln Leu Ala
 1               5                  10                  15

Leu Thr Trp

<210> SEQ ID NO 382
<211> LENGTH: 20
<212> TYPE: PRT
<213> ORGANISM: Artificial Sequence
<220> FEATURE:
<223> OTHER INFORMATION: Hybrid antigen

<400> SEQUENCE: 382

Ser Ile Ile Asn Phe Glu Lys Leu Gly Ser Gly Arg Lys Leu Phe Phe
1               5                   10                  15

Asn Leu Arg Trp
            20

<210> SEQ ID NO 383
<211> LENGTH: 19
<212> TYPE: PRT
<213> ORGANISM: Artificial Sequence
<220> FEATURE:
<223> OTHER INFORMATION: Heat shock protein binding domain

<400> SEQUENCE: 383

Asn Leu Leu Arg Leu Thr Gly Trp Gly Ser Gly Ser Ile Ile Asn Phe
1               5                   10                  15

Glu Lys Leu

<210> SEQ ID NO 384
<211> LENGTH: 20
<212> TYPE: PRT
<213> ORGANISM: Artificial Sequence
<220> FEATURE:
<223> OTHER INFORMATION: Heat shock protein binding domain

<400> SEQUENCE: 384

Asn Leu Leu Arg Leu Thr Gly Trp Phe Phe Arg Lys Ser Ile Ile Asn
1               5                   10                  15

Phe Glu Lys Leu
            20

<210> SEQ ID NO 385
<211> LENGTH: 18
<212> TYPE: PRT
<213> ORGANISM: Artificial Sequence
<220> FEATURE:
<223> OTHER INFORMATION: Heat shock protein binding domain

<400> SEQUENCE: 385

Asn Leu Leu Arg Leu Thr Gly Trp Arg Lys Ser Ile Ile Asn Phe Glu
1               5                   10                  15

Lys Leu

<210> SEQ ID NO 386
<211> LENGTH: 19
<212> TYPE: PRT
<213> ORGANISM: Artificial Sequence
<220> FEATURE:
<223> OTHER INFORMATION: Heat shock protein binding domain

<400> SEQUENCE: 386

Asn Leu Leu Arg Leu Thr Gly Trp Gly Ser Gly Arg Gly Tyr Val Tyr
1               5                   10                  15

Gln Gly Leu

<210> SEQ ID NO 387
<211> LENGTH: 20

-continued

```
<212> TYPE: PRT
<213> ORGANISM: Artificial Sequence
<220> FEATURE:
<223> OTHER INFORMATION: Heat shock protein binding domain

<400> SEQUENCE: 387

Asn Leu Leu Arg Leu Thr Gly Trp Phe Phe Arg Lys Arg Gly Tyr Val
1               5                   10                  15

Tyr Gln Gly Leu
            20

<210> SEQ ID NO 388
<211> LENGTH: 18
<212> TYPE: PRT
<213> ORGANISM: Artificial Sequence
<220> FEATURE:
<223> OTHER INFORMATION: Heat shock protein binding domain

<400> SEQUENCE: 388

Asn Leu Leu Arg Leu Thr Gly Trp Arg Lys Arg Gly Tyr Val Tyr Gln
1               5                   10                  15

Gly Leu

<210> SEQ ID NO 389
<211> LENGTH: 10
<212> TYPE: PRT
<213> ORGANISM: Artificial Sequence
<220> FEATURE:
<223> OTHER INFORMATION: Heat shock protein binding domain

<400> SEQUENCE: 389

Glu Leu Ala Gly Ile Gly Ile Leu Thr Val
1               5                   10

<210> SEQ ID NO 390
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 390

Ser Leu Leu Met Trp Ile Thr Gln Val
1               5

<210> SEQ ID NO 391
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 391

Ser Val Tyr Asp Phe Phe Val Trp Leu
1               5

<210> SEQ ID NO 392
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 392

Gly Leu Tyr Asp Gly Met Glu His Leu
1               5
```

```
<210> SEQ ID NO 393
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 393

Tyr Leu Glu Pro Gly Pro Val Thr Val
 1               5

<210> SEQ ID NO 394
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 394

Lys Ala Ser Glu Lys Ile Phe Tyr Val
 1               5

<210> SEQ ID NO 395
<211> LENGTH: 21
<212> TYPE: PRT
<213> ORGANISM: Artificial Sequence
<220> FEATURE:
<223> OTHER INFORMATION: Hybrid antigen

<400> SEQUENCE: 395

Glu Leu Ala Gly Ile Gly Ile Leu Thr Val Gly Ser Gly Asn Leu Leu
 1               5                  10                  15

Arg Leu Thr Gly Trp
            20

<210> SEQ ID NO 396
<211> LENGTH: 20
<212> TYPE: PRT
<213> ORGANISM: Artificial Sequence
<220> FEATURE:
<223> OTHER INFORMATION: Hybrid antigen

<400> SEQUENCE: 396

Ser Leu Leu Met Trp Ile Thr Gln Val Gly Ser Gly Asn Leu Leu Arg
 1               5                  10                  15

Leu Thr Gly Trp
            20

<210> SEQ ID NO 397
<211> LENGTH: 20
<212> TYPE: PRT
<213> ORGANISM: Artificial Sequence
<220> FEATURE:
<223> OTHER INFORMATION: Hybrid antigen

<400> SEQUENCE: 397

Ser Val Tyr Asp Phe Phe Val Trp Leu Gly Ser Gly Asn Leu Leu Arg
 1               5                  10                  15

Leu Thr Gly Trp
            20

<210> SEQ ID NO 398
<211> LENGTH: 20
<212> TYPE: PRT
```

<213> ORGANISM: Artificial Sequence
<220> FEATURE:
<223> OTHER INFORMATION: Hybrid antigen

<400> SEQUENCE: 398

Gly Leu Tyr Asp Gly Met Glu His Leu Gly Ser Gly Asn Leu Leu Arg
 1               5                  10                  15

Leu Thr Gly Trp
            20

<210> SEQ ID NO 399
<211> LENGTH: 20
<212> TYPE: PRT
<213> ORGANISM: Artificial Sequence
<220> FEATURE:
<223> OTHER INFORMATION: Hybrid antigen

<400> SEQUENCE: 399

Tyr Leu Glu Pro Gly Pro Val Thr Val Gly Ser Gly Asn Leu Leu Arg
 1               5                  10                  15

Leu Thr Gly Trp
            20

<210> SEQ ID NO 400
<211> LENGTH: 20
<212> TYPE: PRT
<213> ORGANISM: Artificial Sequence
<220> FEATURE:
<223> OTHER INFORMATION: Hybrid antigen

<400> SEQUENCE: 400

Lys Ala Ser Glu Lys Ile Phe Tyr Val Gly Ser Gly Asn Leu Leu Arg
 1               5                  10                  15

Leu Thr Gly Trp
            20

<210> SEQ ID NO 401
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 401

Ala Leu Lys His Arg Ala Tyr Glu Leu
 1               5

<210> SEQ ID NO 402
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 402

Ile Leu Lys Glu Pro Val His Gly Val
 1               5

<210> SEQ ID NO 403
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 403

```
Ser Leu Phe Asn Thr Val Ala Thr Leu
  1               5
```

<210> SEQ ID NO 404
<211> LENGTH: 11
<212> TYPE: PRT
<213> ORGANISM: Artificial Sequence
<220> FEATURE:
<223> OTHER INFORMATION: Heat shock protein binding domain

<400> SEQUENCE: 404

```
Val Leu Asp Val Gly Asp Ala Tyr Phe Ser Val
  1               5                  10
```

<210> SEQ ID NO 405
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 405

```
Val Ile Tyr Gln Tyr Met Asp Asp Leu
  1               5
```

<210> SEQ ID NO 406
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 406

```
Ser Leu Tyr Asn Thr Val Ala Thr Leu
  1               5
```

<210> SEQ ID NO 407
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 407

```
Ala Ile Ile Arg Ile Leu Gln Gln Leu
  1               5
```

<210> SEQ ID NO 408
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 408

```
Ala Phe His His Val Ala Arg Glu Leu
  1               5
```

<210> SEQ ID NO 409
<211> LENGTH: 20
<212> TYPE: PRT
<213> ORGANISM: Artificial Sequence
<220> FEATURE:
<223> OTHER INFORMATION: Hybrid antigen

<400> SEQUENCE: 409

```
Ala Leu Lys His Arg Ala Tyr Glu Leu Gly Ser Gly Asn Leu Leu Arg
1               5                   10                  15

Leu Thr Gly Trp
            20
```

<210> SEQ ID NO 410
<211> LENGTH: 20
<212> TYPE: PRT
<213> ORGANISM: Artificial Sequence
<220> FEATURE:
<223> OTHER INFORMATION: Hybrid antigen

<400> SEQUENCE: 410

```
Ile Leu Lys Glu Pro Val His Gly Val Gly Ser Gly Asn Leu Leu Arg
1               5                   10                  15

Leu Thr Gly Trp
            20
```

<210> SEQ ID NO 411
<211> LENGTH: 20
<212> TYPE: PRT
<213> ORGANISM: Artificial Sequence
<220> FEATURE:
<223> OTHER INFORMATION: Hybrid antigen

<400> SEQUENCE: 411

```
Ser Leu Phe Asn Thr Val Ala Thr Leu Gly Ser Gly Asn Leu Leu Arg
1               5                   10                  15

Leu Thr Gly Trp
            20
```

<210> SEQ ID NO 412
<211> LENGTH: 22
<212> TYPE: PRT
<213> ORGANISM: Artificial Sequence
<220> FEATURE:
<223> OTHER INFORMATION: Hybrid antigen

<400> SEQUENCE: 412

```
Val Leu Asp Val Gly Asp Ala Tyr Phe Ser Val Gly Ser Gly Asn Leu
1               5                   10                  15

Leu Arg Leu Thr Gly Trp
            20
```

<210> SEQ ID NO 413
<211> LENGTH: 20
<212> TYPE: PRT
<213> ORGANISM: Artificial Sequence
<220> FEATURE:
<223> OTHER INFORMATION: Hybrid antigen

<400> SEQUENCE: 413

```
Val Ile Tyr Gln Tyr Met Asp Asp Leu Gly Ser Gly Asn Leu Leu Arg
1               5                   10                  15

Leu Thr Gly Trp
            20
```

<210> SEQ ID NO 414
<211> LENGTH: 20
<212> TYPE: PRT
<213> ORGANISM: Artificial Sequence
<220> FEATURE:
<223> OTHER INFORMATION: Hybrid antigen

<400> SEQUENCE: 414

```
Ser Leu Tyr Asn Thr Val Ala Thr Leu Gly Ser Gly Asn Leu Leu Arg
1               5                   10                  15

Leu Thr Gly Trp
            20

<210> SEQ ID NO 415
<211> LENGTH: 20
<212> TYPE: PRT
<213> ORGANISM: Artificial Sequence
<220> FEATURE:
<223> OTHER INFORMATION: Hybrid antigen

<400> SEQUENCE: 415

Ala Ile Ile Arg Ile Leu Gln Gln Leu Gly Ser Gly Asn Leu Leu Arg
1               5                   10                  15

Leu Thr Gly Trp
            20

<210> SEQ ID NO 416
<211> LENGTH: 20
<212> TYPE: PRT
<213> ORGANISM: Artificial Sequence
<220> FEATURE:
<223> OTHER INFORMATION: Hybrid antigen

<400> SEQUENCE: 416

Ala Phe His His Val Ala Arg Glu Leu Gly Ser Gly Asn Leu Leu Arg
1               5                   10                  15

Leu Thr Gly Trp
            20

<210> SEQ ID NO 417
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 417

Asn Leu Leu Arg Leu Thr Gly Trp
1               5

<210> SEQ ID NO 418
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 418

Phe Tyr Gln Leu Ala Leu Tyr Trp
1               5

<210> SEQ ID NO 419
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue
```

-continued

```
<400> SEQUENCE: 419

Arg Lys Leu Phe Phe Asn Leu Arg Trp
1               5
```